United States Patent [19]
Betts et al.

[11] Patent Number: 5,541,178
[45] Date of Patent: *Jul. 30, 1996

[54] CARBAPENEM ANTIBIOTIC COMPOUNDS

[75] Inventors: Michael J. Betts, Wilmslow; Michael L. Swain, Stockport, both of England

[73] Assignee: Zeneca Limited, London, England

[*] Notice: The term of this patent shall not extend beyond the expiration date of Pat. No. 5,478,820.

[21] Appl. No.: 129,167

[22] PCT Filed: Apr. 2, 1992

[86] PCT No.: PCT/GB92/00588

§ 371 Date: Oct. 6, 1993

§ 102(e) Date: Oct. 6, 1993

[87] PCT Pub. No.: WO92/17481

PCT Pub. Date: Oct. 15, 1992

[30] Foreign Application Priority Data

Apr. 8, 1991 [GB] United Kingdom .................. 9107341

[51] Int. Cl.⁶ .................. C07D 477/00; C07D 207/16; C07C 229/64; C07C 229/62
[52] U.S. Cl. .................. 514/210; 540/350
[58] Field of Search .................. 514/210; 540/302

[56] References Cited

U.S. PATENT DOCUMENTS

| | | |
|---|---|---|
| 4,206,219 | 6/1980 | Christensen et al. . |
| 4,208,422 | 6/1980 | Christensen et al. . |
| 4,218,462 | 8/1980 | Christensen et al. . |
| 4,232,036 | 11/1980 | Christensen et al. . |
| 4,943,569 | 7/1990 | Sunagawa .................. 514/210 |
| 4,974,544 | 12/1990 | Ohta . |
| 5,194,624 | 3/1993 | Murata et al. . |
| 5,215,983 | 6/1993 | Murata et al. . |

FOREIGN PATENT DOCUMENTS

| | | |
|---|---|---|
| 0017992 | 10/1980 | European Pat. Off. . |
| 0126587 | 11/1984 | European Pat. Off. . |
| 0160391 | 11/1985 | European Pat. Off. . |
| 0182213 | 5/1986 | European Pat. Off. . |
| 0243686 | 11/1987 | European Pat. Off. . |
| 0443883 | 8/1991 | European Pat. Off. . |
| 0472062 | 2/1992 | European Pat. Off. . |
| 60-233076 | 11/1985 | Japan . |

*Primary Examiner*—Rebecca Cook
*Attorney, Agent, or Firm*—Cushman Darby & Cushman L.L.P.

[57] ABSTRACT

A carbapenem compound of the formula (I)

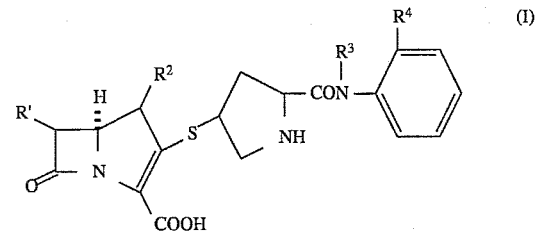

wherein:
$R^1$ is 1-hydroxyethyl, 1-fluoroethyl or hydroxymethyl;
$R^2$ is hydrogen or $C_{1-4}$alkyl;
$R^3$ is hydrogen or $C_{1-4}$alkyl;
$R^4$ is hydroxy or carboxy;
and the phenyl ring is optionally further substituted by one or two substituents selected from halo, cyano, $C_{1-4}$alkyl, nitro, hydroxy, carboxy, $C_{1-4}$alkoxy, trifluoromethyl, $C_{1-4}$alkoxycarbonyl, carbamoyl, $C_{1-4}$alkylcarbamoyl, di-$C_{1-4}$alkylcarbamoyl, amino, $C_{1-4}$alkylamino, di-$C_{1-4}$alkylamino sulphonic acid, $C_{1-4}$alkylS(O)$_n$— (wherein n is 0–2), N-$C_{1-4}$alkanesulphonamido, $C_{1-4}$alkanoylamino and $C_{1-4}$alkanoyl(N-$C_{1-4}$alkyl)amino: provided that the phenyl ring is substituted by at least one carboxy; or a pharmaceutically acceptable salt or in vivo hydrolysable ester thereof.

14 Claims, No Drawings

CARBAPENEM ANTIBIOTIC COMPOUNDS

This application is a 371 of PCT/GB92/00588 filed Apr. 2, 1992.

The present invention relates to carbapenems and in particular to such compounds containing a carboxy substituted phenyl group. This invention further relates to processes for their preparation, to intermediates in their preparation, to their use as therapeutic agents and to pharmaceutical compositions containing them. The compounds of this invention are antibiotics and can be used in the treatment of any disease that is conventionally treated with antibiotics for example in the treatment of bacterial infection in mammals including humans.

Carbapenems were first isolated from fermentation media in 1974 and were found to have broad spectrum antibacterial activity. Since this discovery substantial investigations have been made into new carbapenem derivatives and many hundreds of patents and scientific papers have been published.

The first, and so far the only, carbapenem to be commercially marketed is imipenem (N-formimidoyl thienamycin). This compound has a broad spectrum of antibacterial activity.

The present invention provides compounds with a broad spectrum of antibacterial activity including both Gram positive and negative, aerobic and anaerobic bacteria. They exhibit good stability to beta-lactamases. In addition representative compounds of this invention exhibit favourable pharmacokinetics.

The carbapenem derivatives referred to herein are named in accordance with the generally accepted semi-systematic nomenclature:

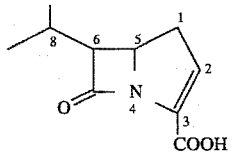

Accordingly the present invention provides a compound of the formula (I)

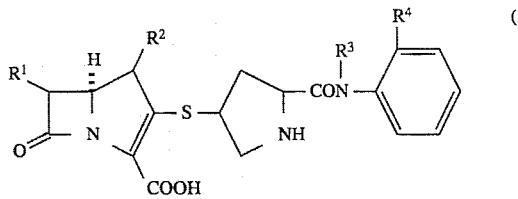

wherein:
$R^1$ is 1-hydroxyethyl, 1-fluoroethyl or hydroxymethyl;
$R^2$ is hydrogen or $C_{1-4}$alkyl;
$R^3$ is hydrogen or $C_{1-4}$alkyl;
$R^4$ is hydroxy or carboxy;
and the phenyl ring is optionally further substituted by one or two substituents selected from halo, cyano, $C_{1-4}$alkyl, nitro, hydroxy, carboxy, $C_{1-4}$alkoxy, trifluoromethyl, $C_{1-4}$alkoxycarbonyl, carbamoyl, $C_{1-4}$alkylcarbamoyl, di-$C_{1-4}$alkylcarbamoyl, amino, $C_{1-4}$alkylamino, di-$C_{1-4}$alkylamino, sulphonic acid, $C_{1-4}$alkylS(O)$_n$— (wherein n is 0–2), N-$C_{1-4}$alkanesulphonamido, $C_{1-4}$alkanoylamino and $C_{1-4}$ alkanoyl(N-$C_{1-4}$alkyl)amino: provided that the phenyl ring is substituted by at least one carboxy; or a pharmaceutically acceptable salt or in vivo hydrolysable ester thereof.

The term alkyl includes all straight and branched chain structures, for example, $C_{1-4}$alkyl includes n-butyl and 2-methylpropyl.

Preferably $R^1$ is 1-hydroxyethyl.

$R^2$ is hydrogen or $C_{1-4}$alkyl for example methyl, ethyl, n-propyl, 1-methylethyl and n-butyl.

Preferably $R^2$ is hydrogen or methyl and in particular $R^2$ is methyl.

$R^3$ is hydrogen or $C_{1-4}$alkyl for example methyl, ethyl, n-propyl, isopropyl and n-butyl.

Preferably $R^3$ is hydrogen or methyl.

$R^4$ is hydroxy or carboxy.

Suitable substituents for the phenyl ring include, for example:

for halo: fluoro, chloro, bromo and iodo;

for $C_{1-4}$alkyl: methyl, ethyl, propyl, 1-methylethyl, butyl and 2-methylpropyl;

for $C_{1-4}$alkoxy: methoxy, ethoxy, propoxy, 1-methylethoxy, butoxy and 2-methylpropoxy;

for $C_{1-4}$alkoxycarbonyl: methoxycarbonyl, ethoxycarbonyl and propoxycarbonyl;

for $C_{1-4}$alkylcarbamoyl: methylcarbamoyl, ethylcarbamoyl and propylcarbamoyl;

for $C_{1-4}$alkylamino: methylamino, ethylamino and propylamino;

for di-$C_{1-4}$alkylamino: dimethylamino, diethylamino and methylethylamino;

for $C_{1-4}$alkylS(O)$_n$—: methylthio, methylsulphinyl and methylsulphonyl;

for $C_{1-4}$alkanoylamino: acetamido and propionamido;

for N-$C_{1-4}$alkanesulphonamido: N-methanesulphonamido and N-ethanesulphonamido;

for $C_{1-4}$alkanoyl(N-$C_{1-4}$alkyl)amino: N-methylacetamido and N-ethylacetamido.

The present invention covers all epimeric, diastereoisomeric and tautomeric forms of the compounds of the formula (I) wherein the absolute stereochemistry at the 5-position is as illustrated in formula (I). When a bond is represented as a wedge, this indicates that in three dimensions the bond would be coming forward out of the paper and when a bond is represented as hatched, this indicates that in three dimensions the bond would be going back into the paper. The compounds of the formula (I) have a number of other centres of optical activity, namely: within the group $R^1$ (when $R^1$ is 1-hydroxyethyl or 1-fluoroethyl); at the 6-position; at the 1-position (when $R^2$ is $C_{1-4}$alkyl); and at the 2' and 4' positions in the pyrrolidine ring:

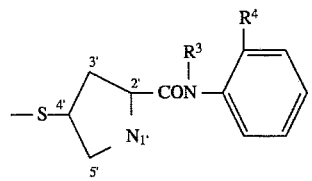

Preferred compounds are those in which the beta-lactam protons are in trans configuration with respect to one another. When $R^1$ is 1-hydroxyethyl or 1-fluoroethyl it is preferred that the 8-substituent has the R-configuration. Thus a preferred class of compounds is that of the formula (III):

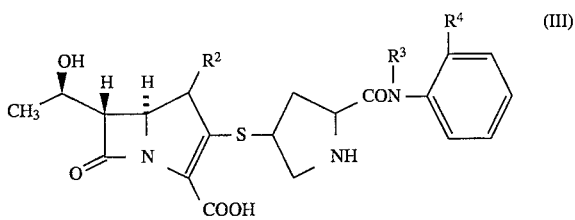

and pharmaceutically acceptable salts and in vivo hydrolysable esters thereof, wherein $R^2$, $R^3$ and $R^4$ are as hereinbefore defined.

When $R^2$ is $C_{1-4}$alkyl for example methyl it is preferred that the compound is in the form of the 1R configuration.

Preferred compounds are those in which the pyrrolidine ring has the following absolute stereochemistry at the 2'- and 4'-positions:

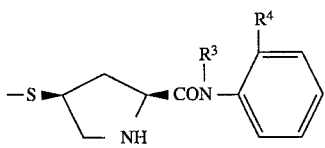

A suitable class of compounds of the present invention is that of the formula (IV):

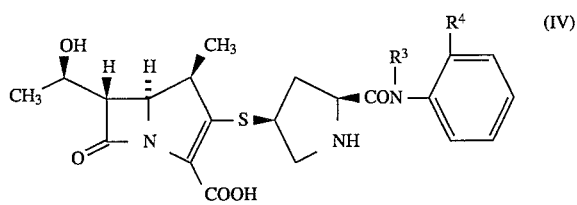

and pharmaceutically acceptable salts and in vivo hydrolysable esters thereof;
wherein $R^3$, $R^4$ and optional substituents on the phenyl ring are as defined hereinbefore in formula (I).

In another aspect a suitable class of compounds are the compounds of the formula (IV) wherein $R^3$ is hydrogen, methyl or ethyl; and $R^4$ and optional substituents on the phenyl ring are as defined hereinabove in formula (I).

In yet another aspect a suitable class of compounds is that of the compounds of the formula (IV) wherein the phenyl ring is optionally further substituted by one or two substituents selected from methyl, ethyl, hydroxy, carboxy, cyano, fluoro, chloro, bromo, trifluoromethyl, methoxycarbonyl, ethoxycarbonyl, carbamoyl, sulphonic acid, nitro, methoxy, ethoxy and propoxy, provided that the phenyl ring is substituted by at least one carboxy; and $R^3$ and $R^4$ are as defined hereinbefore in formula (I).

A suitable class of compounds of the present invention is that of the formula (IV) wherein:

$R^3$ is hydrogen or methyl;

$R^4$ is hydroxy or carboxy;
and the phenyl ring is optionally further substituted by one or two substituents selected from methyl, ethyl, hydroxy, carboxy, cyano, chloro, bromo, nitro, methoxy and ethoxy, provided that the phenyl ring is substituted by at least one carboxy.

A suitable class of compounds of the present invention is that of the formula (IV) wherein:

$R^3$ is hydrogen;

$R^4$ is hydroxy;
and the phenyl ring is optionally further substituted by one or two substituents selected from methyl, hydroxy, chloro and carboxy, provided that the phenyl ring is substituted by at least one carboxy.

A suitable class of compounds of the present invention is that of the formula (IV) wherein:

$R^3$ is hydrogen;

$R^4$ is carboxy;
and the phenyl ring is optionally further substituted by one substituent selected from methyl, hydroxy, chloro and carboxy.

Particular compounds of the present invention are, for example, the following compounds of the formula (IV):

(1R,5S,6S,8R,2'S,4'S)-2-(2-(4-carboxy-2 -hydroxyphenylcarbamoyl)pyrrolidin- 4-ylthio)-6-(1-hydroxyethyl)-1-methylcarbapenem-3-carboxylic acid;

(1R,5S,6S,8R,2'S,4'S)-2-(2-(5-carboxy-2 -hydroxyphenylcarbamoyl)pyrrolidin-4-ylthio)-6-(1-hydroxyethyl)-1-methylcarbapenem-3 -carboxylic acid;

(1R,5S,6S,8R,2'S,4'S)-2-(2-(2,5 -dicarboxyphenylcarbamoyl)pyrrolidin-4-ylthio)-6-(1-hydroxyethyl)-1-methylcarbapenem-3 -carboxylic acid;

(1R,5S,6S,8R,2'S,4'S)-2-(2-(2,3 -dicarboxyphenylcarbamoyl)pyrrolidin-4-ylthio)-6-(1-hydroxyethyl)-1-methylcarbapenem-3 -carboxylic acid;

(1R,5S,6S,8R,2'S,4'S)-2-(2-(2 -carboxyphenylcarbamoyl)pyrrolidin-4 -ylthio)-6-(1-hydroxyethyl)-1-methylcarbapenem-3-carboxylic acid;

(1R,5S,6S,8R,2'S,4'S)-2-(2-(2-carboxy-3 -methylphenylcarbamoyl)pyrrolidin-4-ylthio)-6-(1-hydroxyethyl)-1-methylcarbapenem-3 -carboxylic acid;

(1R,5S,6S,8R,2'S,4'S)-2-(2-(2-carboxy-4 -methylphenylcarbamoyl)pyrrolidin-4-ylthio)-6-(1-hydroxyethyl)-1-methylcarbapenem-3 -carboxylic acid;

(1R,5S,6S,8R,2'S,4'S)-2-(2-(2-carboxy-4 -chlorophenylcarbamoyl)pyrrolidin-4-ylthio)-6-(1-hydroxyethyl)-1-methylcarbapenem-3 -carboxylic acid;

(1R,5S,6S,8R,2'S,4'S)-2-(2-(2-carboxy-6 -hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-6 -chlorophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5 -chlorophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-6 -methylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2,4 -dicarboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2,6 -dicarboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-6 -methoxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5 -trifluoromethylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5 -methylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4 -fluorophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5 -fluorophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-hydroxy-3-chloro-6-carboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5-carbamoylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-methylthiophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-methylsulphinylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-methylsulphonylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4,5-dimethoxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-3-hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-3-methoxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-hydroxy-4-carboxy-5-chlorophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5-nitrophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5-methoxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-methoxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-nitrophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-(N-methylacetamido)phenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-sulphophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(3-carboxy-2-hydroxy-5-chlorophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(3-carboxy-2-hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(4-carboxy-2-hydroxyphenyl-N-methylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-3-methoxycarbonylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-3-nitrophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-carbamoylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-3-carbamoylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-cyanophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5-cyanophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5-hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-6-(N-methylacetamido)phenylcarbamoyl)pyrrolidin-4-ylthio)-6-(1-hydroxyethyl)-1-methylcarbapenem-3-carboxylic acid; and (1R,5S,6S,8R,2'S,4'S)-2-(2-(2,5-di-carboxy-4-aminophenylcarbamoyl)pyrrolidin-4-ylthio)-6-(1-hydroxyethyl)-1-methylcarbapenem-3-carboxylic acid;

or a pharmaceutically acceptable salt or in vivo hydrolysable ester thereof.

Preferred compounds of the present invention are, for example, the following compounds of the formula (IV):

(1R,5S,6S,8R,2'S,4'S)-2-(2-(4-carboxy-2-hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(5-carboxy-2-hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2,5-dicarboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2,3-dicarboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-3-methylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-methylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-chlorophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-6-hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-6-chlorophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5-chlorophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-6-methylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2,4-dicarboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2,6-dicarboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-6-methoxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5-trifluoromethylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5-methylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-fluorophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5-fluorophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-hydroxy-3-chloro-6-carboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5-carbamoylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-methylthiophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-methylthiophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-methoxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-nitrophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-sulphophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(3-carboxy-2-hydroxy-5-chlorophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4,5-dimethoxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5-methoxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(3-carboxy-2-hydroxyphenylcarbamoyl)pyrrolidin-4-ylthio)-6-(1-hydroxyethyl)-1-methylcarbapenem-3-carboxylic acid; and (1R,5S,6S,8R,2'S,4'S)-2-(2-(4-carboxy-2-hydroxyphenyl-N-methylcarbamoyl)pyrrolidin-4-ylthio)-6-(1-hydroxyethyl)-1-methylcarbapenem-3-carboxylic acid;

and pharmaceutically acceptable salts and in vivo hydrolysable esters thereof.

Especially preferred compounds of the present invention are, for example, the following compounds of the formula (IV):

(1R,5S,6S,8R,2'S,4'S)-2-(2-(4-carboxy-2-hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(5-carboxy-2-hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2,5-dicarboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2,3-dicarboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-3-methylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4-methylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(6-carboxy-2-hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(5-carboxy-2-hydroxy-3-chlorophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2,4-dicarboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2,6-dicarboxyphenylcarbamoyl)pyrrolidin-4-ylthio)-6-(1-hydroxyethyl)-1-methylcarbapenem-3-carboxylic acid; and (1R,5S,6S,8R,2'S,4'S)-2-(2-(2-carboxy-4-chlorophenylcarbamoyl)pyrrolidin-4-ylthio)-6-(1-hydroxyethyl)-1-methylcarbapenem-3-carboxylic acid;

and pharmaceutically acceptable salts and in vivo hydrolysable esters thereof.

Suitable pharmaceutically acceptable salts include acid addition salts such as hydrochloride, hydrobromide, citrate, maleate and salts formed with phosphoric and sulphuric acid. In another aspect suitable salts are base salts such as an alkali metal salt for example sodium or potassium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or aminoacids, for example, lysine.

For the avoidance of doubt there may be one, two or three salt-forming cations dependent on the number of carboxylic acid functions and valency of said cations.

Preferred pharmaceutically acceptable salts are sodium and potassium salts. However, to facilitate isolation of the salt during preparation, salts which are less soluble in the chosen solvent may be preferred, whether pharmaceutically acceptable or not.

In vivo hydrolysable esters are those pharmaceutically acceptable esters that hydrolyse in the human body to produce the parent hydroxy or carboxy compound. Such esters can be identified by administering, eg. intravenously to a test animal, the compound under test and subsequently examining the test animal's body fluids. Suitable in vivo hydrolysable esters for hydroxy include acetoxy, propionyloxy, pivaloyloxy, $C_{1-4}$alkoxycarbonyloxy for example ethoxycarbonyloxy, phenylacetoxy and phthalidyl. Suitable in vivo hydrolysable esters for carboxy include $C_{1-6}$alkoxymethyl esters for example methoxymethyl; $C_{1-6}$alkanoyloxymethyl esters for example pivaloyloxymethyl; $C_{3-8}$ cycloalkoxycarbonyloxy$C_{1-6}$alkyl, for example 1-cyclohexyloxycarbonyloxyethyl; 1,3-dioxolen-2-onylmethyl esters for example 5-methyl-1,3-dioxolen-2-onylmethyl; phthalidyl esters and $C_{1-6}$alkoxycarbonyloxyethyl esters for example 1-ethoxycarbonyloxyethyl and may be formed at any carboxy group in the compounds of this invention.

In order to use a compound of the formula (I) or a pharmaceutically acceptable salt or in vivo hydrolysable ester thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt or in vivo hydrolysable ester thereof and a pharmaceutically acceptable carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, emulsions, dispersible powders, suppositories and sterile injectable aqueous or oily solutions or suspensions.

In addition to the compounds of the present invention the pharmaceutical composition of this invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenecid) and inhibitors of metabolising enzymes (for example inhibitors of dehydropeptidases, for example Z-2-acylamino-3-substituted propenoates such as cilastatin) and N-acylated amino acids such as betamipron (also see EP-A-178911).

A suitable pharmaceutical composition of this invention is one suitable for oral administration in unit dosage form, for example a tablet or capsule which contains between 100 mg and 1 g of the compound of this invention.

A preferred pharmaceutical composition of the invention is one suitable for intravenous, subcutaneous or intramuscular injection, for example a sterile injectable composition containing between 1 and 50% w/w of the compound of this invention.

Specific examples of compositions, which are constituted as a 1% solution in water, freeze dried and may be made up by adding 0.9% aqueous sodium chloride solution to give the required concentration, preferably 1 mg–10 mg/ml, are as follows:

| Composition 1 | |
|---|---|
| Compound of Example 7 | 50 mg |
| Composition 2 | |
| Compound of Example 7 | 50 mg |
| Glycine | 31 mg |

Further specific examples of compositions are as above, but where the compound of example 7 is replaced by any of the following compounds of the formula (I):

(1R,5S,6S,8R,2'S,4'S)-2-(2-(4-carboxy-2 -hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(5-carboxy-2 -hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2,5 -dicarboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2,3 -dicarboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxyphenylcarbamoyl)pyrrolidin-4 -ylthio)-6-(1-hydroxyethyl)-1-methylcarbapenem-3-carboxylic acid;

(1R,5S,6S,8R,2'S,4'S)-2-(2-(2-carboxy-3 -methylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(6-carboxy-2 -hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(5-carboxy-2-hydroxy-3 -chlorophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2,4 -dicarboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2,6 -dicarboxyphenylcarbamoyl)pyrrolidin-4-ylthio)-6-(1-hydroxyethyl)-1-methylcarbapenem-3-carboxylic acid; and (1R,5S,6S,8R,2'S,4'S)-2-(2-(2-carboxy-4 -chlorophenylcarbamoyl)pyrrolidin-4-ylthio)-6-(1-hydroxyethyl)-1-methylcarbapenem-3-carboxylic acid;

and pharmaceutically acceptable salts thereof.

The pharmaceutical compositions of the invention will normally be administered to man in order to combat infections caused by bacteria, in the same general manner as that employed for imipenem due allowance being made in terms of dose levels for the pharmacokinetics of the compound of the present invention relative to the clinical use of imipenem. Thus each patient will receive a daily intravenous, subcutaneous or intramuscular dose of 0.05 to 5 g, and preferably 0.1 to 2.5 g, of the compound of this invention, the composition being administered 1 to 4 times per day, preferably 1 or 2 times a day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose. Thus a suitable daily oral dose is 0.05 to 5 g. of the compound of this invention, the composition being administered 1 to 4 times per day.

In a further aspect the present invention provides a process for preparing the compounds of the formula (I) or a pharmaceutically acceptable salt or in vivo hydrolysable ester thereof which process comprises deprotecting a compound of the formula (V) wherein the phenyl ring is optionally further substituted as in formula (I):

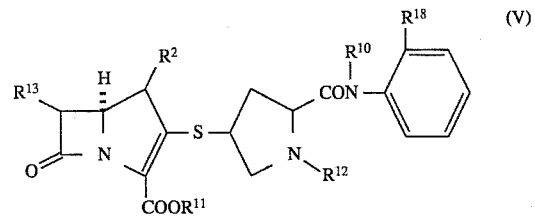

wherein $R^2$ is as hereinbefore defined; $R^{10}$ is a group $R^3$ or an amino protecting group; $R^{13}$ is a group $R^1$, protected hydroxymethyl or 1-(protected hydroxy)ethyl; $R^{11}$ is hydrogen or a carboxy protecting group; $R^{12}$ is hydrogen or an amino protecting group, $R^{18}$ is carboxy, hydroxy, a protected carboxy group or a protected hydroxy group and wherein any optional substituent on the phenyl ring is optionally protected; and wherein at least one protecting group is present; and thereinafter if necessary;

(i) forming a pharmaceutically acceptable salt,
(ii) esterifying to form an in vivo hydrolysable ester.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

The compounds of the formula (V) are novel and form another aspect of the invention.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12C)alkyl groups (eg isopropyl, t-butyl); lower alkoxy lower alkyl groups (eg methoxymethyl, ethoxymethyl, isobutoxymethyl); lower aliphatic acyloxy lower alkyl groups, (eg acetoxymethyl, propionyloxymethyl, butyryloxymethyl, pivaloyloxymethyl); lower alkoxycarbonyloxy lower alkyl groups (eg 1-methoxycarbonyloxyethyl, 1-ethoxycarbonyloxyethyl); aryl lower alkyl groups (eg p-methoxybenzyl, o-nitrobenzyl, p-nitrobenzyl, benzhydryl and phthalidyl); tri(lower alkyl)silyl groups (eg trimethylsilyl and t-butyldimethylsilyl); tri(lower alkyl)silyl lower alkyl groups (eg trimethylsilylethyl); diaryl(lower alkyl)silyl groups (eg t-butyl(diphenyl)silyl); and (2–6C)alkenyl groups (eg allyl and vinylethyl).

Methods particularly appropriate for the removal of carboxyl protecting groups include for example acid-, base-, metal- or enzymically-catalysed hydrolysis, for groups such as p-nitrobenzyloxycarbonyl, hydrogenation and for groups such as o-nitrobenzyloxycarbonyl, photolytically.

Examples of hydroxyl protecting groups include lower alkenyl groups (eg allyl); lower alkanoyl groups (eg acetyl); lower alkoxycarbonyl groups (eg t-butoxycarbonyl); lower alkenyloxycarbonyl groups (eg allyloxycarbonyl); aryl lower alkoxycarbonyl groups (eg benzoyloxycarbonyl, p-methoxybenzyloxycarbonyl, o-nitrobenzyloxycarbonyl, p-nitrobenzyloxycarbonyl); tri lower alkylsilyl (eg trimethylsilyl, t-butyldimethylsilyl) and aryl lower alkyl (eg benzyl) groups.

Examples of amino protecting groups include formyl, aralkyl groups (eg benzyl and substituted benzyl, eg p-methoxybenzyl, nitrobenzyl and 2,4-dimethoxybenzyl, and triphenylmethyl); di-p-anisylmethyl and furylmethyl groups; lower alkoxycarbonyl (eg t-butoxycarbonyl); lower alkenyloxycarbonyl (eg allyloxycarbonyl); aryl lower alkoxycarbonyl groups (eg benzyloxycarbonyl, p-methoxybenzyloxycarbonyl, o-nitrobenzyloxycarbonyl, p-nitrobenzyloxycarbonyl); trialkylsilyl (eg trimethylsilyl and t-butyldimethylsilyl); alkylidene (eg methylidene); benzylidene and substituted benzylidene groups.

Methods appropriate for removal of hydroxy and amino protecting groups include, for example, acid-, base-, metal- or enzymically-catalysed hydrolysis, for groups such as p-nitrobenzyloxycarbonyl, hydrogenation and for groups such as o-nitrobenzyloxycarbonyl, photolyrically.

A preferred protecting group for carboxy and hydroxy groups in compounds of the formula (I) is the group allyl. A preferred method for removal of the allyl group is by palladium catalysis using tetrakis(triphenylphosphine)palladium and Meldrum's acid, in a dipolar aprotic solvent tetrahydrofuran mixture, such as dimethylsulphoxide/tetrahydrofuran, dimethylformide/tetrahydrofuran or 1,3-dimethyltetrahydropyrimidine/tetrahydrofuran, or an alcohol/tetrahydrofuran mixture such as isopropanol/tetrahydrofuran or ethanol/tetrahydrofuran, preferably at ambient temperature. Alternatively, methylaniline may be used in place of Meldrum's acid, in dichloromethane. These conditions allow isolation of the product by precipitation of the sodium salt on the addition of a sodium salt such as sodium 2-ethylhexanoate.

In the following formulae (VII), (VIII), (IX), (XI), (XII) and (XIV) the phenyl ring is optionally further substituted as hereinbefore defined in formula (I).

In another aspect of the present invention the compounds of the formulae (I) and (V) may be prepared by
a) reacting compounds of the formulae (VI) and (VII):

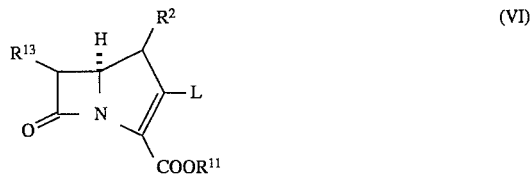

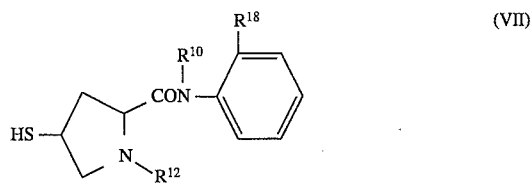

wherein $R^2$, $R^{10}$, $R^{11}$, $R^{12}$, $R^{13}$ and $R^{18}$ are as hereinbefore defined and L is a leaving group, or
b) cyclising a compound of the formula (VIII):

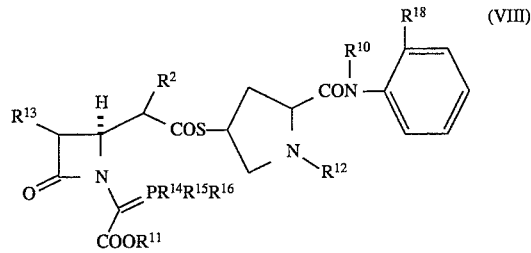

wherein $R^2$, $R^{10}$, $R^{11}$, $R^{12}$, $R^{13}$ and $R^{18}$ are as hereinbefore defined and $R^{14}$, $R^{15}$ and $R^{16}$ are independently selected from $C_{1-6}$alkoxy, aryloxy, di-$C_{1-6}$alkylamino and diarylamino or any two of $R^{14}$–$R^{16}$ represent o-phenylenedioxy; and wherein any functional group is optionally protected and thereinafter if necessary:

(i) removing any protecting groups;

(ii) forming a pharmaceutically acceptable salt;

(iii) esterifying to form an in vivo hydrolysable ester.

Suitably in the compound of the formula (VI), L is the reactive ester of a hydroxy group such as a sulphonate (for example $C_{1-6}$alkanesulphonyloxy, trifluoromethanesulphonyloxy, benzenesulphonyloxy, toluenesulphonyloxy), a phosphoric ester (for example a diarylphosphoric ester such as diphenylphosphoric ester) or L is a halide (for example chloride). In an alternative L is a sulphoxide for example —SOCH=CH—NHCOCH$_3$ which may be readily displaced. Preferably L is diphenylphosphoric ester (—OP(O)(OPh)$_2$).

Compounds of the formula (VI) and their preparation are well known in the carbapenem literature, for example see EP-A-126587, EP-A-160391, EP-A-243686 and EP-A-343499.

The reaction between the compounds of the formulae (VI) and (VII) is typically performed in the presence of a base such as an organic amine for example di-isopropylethylamine or an inorganic base for example an alkali metal carbonate such as potassium carbonate. The reaction is conveniently performed at a temperature between −25° C. and ambient, suitably at about −20° C. The reaction is generally performed in an organic solvent such as acetonitrile or dimethylformamide. The reaction is generally performed in a manner similar to that described in the literature for similar reactions.

The compounds of the formula (VII) are novel and form another aspect of the present invention.

The compounds of the formula (VII) may be prepared by the deprotection of a compound of the formula (IX):

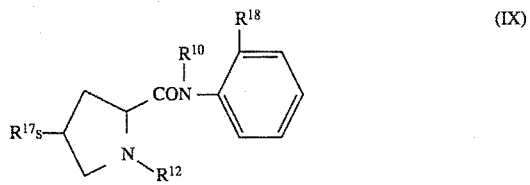

wherein $R^{10}$, $R^{12}$ and $R^{18}$ are as hereinbefore defined and $R^{17}$ is a protecting group, for example $C_{1-6}$alkanoyl or $C_{1-6}$alkoxycarbonyl. Preferred values for $R^{17}$ are acetyl and N-butoxycarbonyl. The compounds of the formula (IX) can be converted to the compounds of the formula (VII) by standard methods of deprotection, for example acetyl groups can be removed by basic hydrolysis in aqueous alkanol, alkenol for example allyl alcohol or tetrahydrofuran.

The compounds of the formula (IX) are novel and form another aspect of the present invention.

The compounds of the formula (IX) may be prepared by the reaction of an activated derivative of a compound of the formula (X), which may be formed in situ, with a compound of the formula (XI):

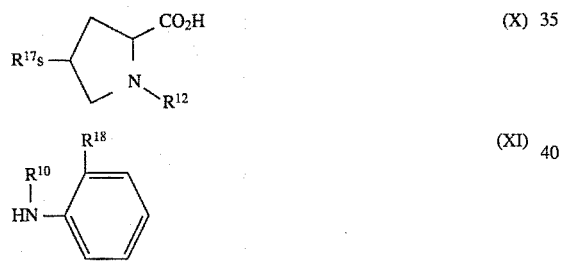

wherein $R^{10}$, $R^{12}$, $R^{17}$ and $R^{18}$ are as hereinbefore defined. Activated derivatives of the compound of the formula (X) include acid halides, anhydrides and 'activated' esters such as 1H-benzol[1,2,3]triazol-1-yl, pentafluorophenyl and 2,4,5-trichlorophenyl esters or the benzimidazol-2-yl ester of the thiocarboxylic acid corresponding to (X). The reaction of the compounds of the formulae (X) and (XI) is performed under standard methods, for example in the presence of Vilsmeier reagent (thus forming the reactive derivative of (X) in situ) at temperatures in the region −30° to +25° C., preferably in the region −20° to +5° C., or in the presence of sulphonyl chloride at ambient temperature.

The compounds of the formulae (X) and (XI) are prepared by standard methods known to the skilled chemist such as the methods of the Examples hereinafter, the methods described in EP-A-126587 or by methods analogous or similar thereto.

Suitably, in the compounds of the formula (VIII), $R^{14}$, $R^{15}$ and $R^{16}$ are independently selected from $C_{1-6}$ alkoxy such as methoxy, ethoxy, isopropoxy, n-propoxy or n-butoxy; aryloxy such as optionally phenoxy; di-$C_{1-6}$alkylamino such as dimethylamino or diethylamino; diarylamino such as diphenylamino or any two of $R^{14}$–$R^{16}$ represent o-phenylenedioxy. Preferably each of $R^{14}$–$R^{16}$ have the same value and are $C_{1-6}$alkoxy for example methoxy, ethoxy, isopropoxy or n-butoxy or are phenoxy.

The compounds of the formula (VIII) are cyclized under conventional conditions known in the art to form compounds of the formula (V). Typical conditions are heating in a substantially inert organic solvent such as toluene, xylene or ethyl acetate at temperatures in the region 60°–150° C. Typically the reaction is performed in an atmosphere of nitrogen and is carried out in the presence of a radical scavenger for example hydroquinone.

The compounds of the formula (VIII) may be formed and cyclized in situ. The compounds of the formula (VIII) may conveniently be prepared by reacting compounds of the formulae (XII) and (XIII):

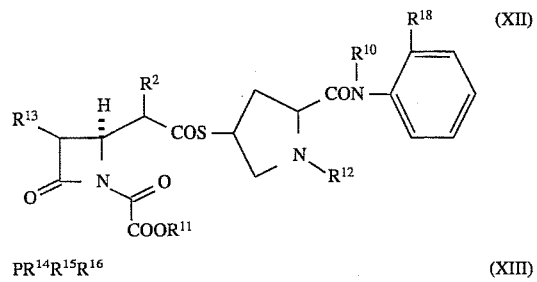

wherein $R^2$, $R^{10}$, $R^{11}$–$R^{16}$, and $R^{18}$ are as hereinbefore defined. Suitably the compound of the formula (XIII) is a phosphite or is the functional equivalent of such a compound.

The reaction between the compounds of the formulae (XII) and (XIII) is conveniently performed in an organic solvent such as toluene, xylene, ethyl acetate, chloroform, dichloromethane, acetonitrile or dimethylformamide. Typically the reaction is carried out at an elevated temperature for example 60°–150° C.

The compounds of the formula (XII) may be prepared by a number of methods known in the art. For example the compounds of the formula (XII) may be prepared by the acylation of a compound of the formula (XIV):

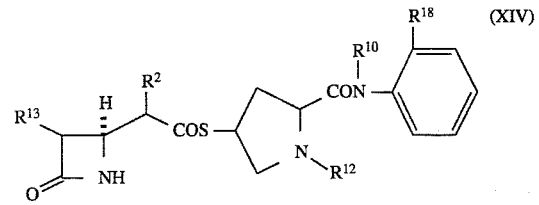

wherein $R^2$, $R^{10}$, $R^{12}$, $R^{13}$, and $R^{18}$ are as hereinbefore defined with a compound of the formula (XV):

Cl—CO—COOR$^{11}$          (XV)

wherein $R^{11}$ is as hereinbefore defined.

The compounds of the formula (XIV) may be prepared by reacting compounds of the formulae (XVI) and (VII):

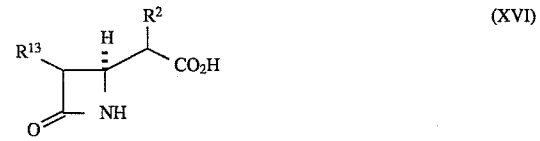

wherein $R^2$ and $R^{13}$ are as hereinbefore defined. The compounds of the formula (XVI) are known in the art and may be reacted with the compounds of the formula (VII) under conventional acylation methods known in the art.

Compounds of the formulae (VII), (XII) and (XIV) are novel and, as such, form another aspect of this invention.

The following biological test methods, data and Examples serve to illustrate the present invention.

Antibacterial Activity

The pharmaceutically acceptable carbapenem compounds of the present invention are useful antibacterial agents having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. In particular the carbapenems of the present invention show good stability to beta-lactamases and in general particularly good pharmacokinetics, especially as regards half life. In general compounds show significant improvement over imipenem.

The antibacterial properties of the compounds of the invention may also be demonstrated in vivo in conventional tests.

Carbapenem compounds have generally been found to be relatively non-toxic to warm-blooded animals, and this generalisation holds true for the compounds of the present invention. Compounds representative of the present invention were administered to mice at doses in excess of those required to afford protection against bacterial infections, and no overt toxic symptoms or side effects attributable to the administered compounds were noted.

The following results were obtained for representative compounds on a standard in vitro test system using Diagnostic Sensitivity Test. The antibacterial activity is described in terms of the minimum inhibitory concentration (MIC) determined by the agar-dilution technique with an inoculum size of $10^4$ CFU/spot.

| ORGANISM | ceftriaxone | MIC (µg/ml) EXAMPLES | | | | | |
|---|---|---|---|---|---|---|---|
| | | 1 | 2 | 4 | 5 | 13 | 31 |
| S. aureus Oxford | 2.00 | 0.13 | 0.13 | 0.25 | 0.06 | 0.25 | 0.13 |
| E. coli DCO | 0.03 | 0.01 | 0.03 | 0.02 | 0.03 | 0.02 | 0.02 |
| P. morganii I + 001 | 0.01 | 0.02 | 0.06 | 0.03 | 0.03 | 0.01 | 0.03 |
| D Morganii DR 062 | 1.00 | 0.02 | 0.06 | 0.03 | 0.03 | 0.02 | 0.06 |
| Enterobacter cloacae P99− | 0.06 | 0.01 | 0.01 | 0.01 | 0.06 | 0.03 | 0.03 |
| Enterobacter cloacae P99+ | 32.00 | 0.25 | 1.00 | 1.00 | 1.00 | 2.00 | 1.00 |
| B. fragilis AMP-S | 2.00 | 0.25 | 0.25 | 0.13 | 0.25 | 0.13 | 0.25 |
| B. fragilis AMP-R | >128.0 | 0.50 | — | 0.50 | 0.25 | 0.50 | 0.25 |

In the following examples, which are representative of the scope:

(a) NMR spectra were taken at 200 MHz or 400 MHz in DMSO-$d_6$/CD$_3$COOD unless otherwise stated;
(b) Allyloxy means the propen-1-yloxy group —OCH$_2$CH=CH$_2$;
(c) THF means tetrahydrofuran;
(d) DMF means dimethylformamide;
(e) DMSO means dimethylsulphoxide;
(f) Meldrum's acid is 2,2-dimethyl-1,3-dioxane-4,6-dione;
(g) Evaporation of solvents was carried out under reduced pressure;
(h) Relative amounts of solvents and solids given in 'parts' are in parts by weight.

EXAMPLE 1

(1R,5S,6S,8R,2'S,4'S)-2-(2-(4-Carboxy-2-hydroxyphenylcarbamoyl)pyrrolidin-4-ylthio)-6-(1-hydroxyethyl)-1-methylcarbapenem-3-carboxylic acid.

To a solution of allyl (1R,5S,6S,8R,2'S,4'S)-2-(1-allyloxycarbonyl-2-(4-allyloxycarbonyl-2-allyloxyphenylcarbamoyl)pyrrolidin-4-ylthio)-6-(1-hydroxyethyl)-1-methylcarbapenem-3-carboxylate (230 mg, 0.33 mM) and Meldrum's acid (380 mg, 2.64 mM) in a mixture of DMF (2 ml) and THF (1 ml), under an argon atmosphere, was added tetrakis(triphenylphosphine)palladium (38 mg, 0.033 mM). The solution was stirred, under argon with protection from the light, for 45 minutes. THF (10 ml) was added slowly, followed by ether (10 ml) to precipitate the product. The resultant suspension was stirred for 10 minutes, the product was collected by filtration, washed first with THF then ether, and dried to give the title product (90%).

NMR: δ 1.17 (d, 6H); 1.78 (quintet, 1H); 2.62–2.73 (m, 2H); 3.22 (dd, 1H); 3.41 (quintet, 1H); 3.50–3.68 (m, 2H); 3.99 (t, 1H); 4.08 (t, 1H); 4.19 (dd, 1H); 7.45 (dd, 1H); 7.50 (d, 1H); 8.29 (d, 1H).

Ms (+ve FAB): 492 (M+H)$^+$.

The starting materials were prepared as follows:

Preparation of Allyl 3-allyloxy-4-aminobenzoate

3-Hydroxy-4-nitrobenzoic acid (20 g, 0.11M) was dissolved in DMF (230 ml), and anhydrous potassium carbonate (45 g, 0.33M) added with stirring. Allyl bromide (23 ml, 0.27M) was run in, and the mixture stirred for 18 hours at ambient temperature. The solvent was removed by evaporation, the residue drowned into water, and product extracted into diethyl ether. The ethereal solution was washed with an aqueous 2M solution of sodium hydroxide, water, brine, and dried over MgSO$_4$. Evaporation of the solvent gave allyl 3-allyloxy-4-nitrobenzoate (25 g).

NMR (CDCl$_3$): δ 4.73–4.76 (m, 2H); 4.83–4.87 (m, 2H); 5.30–5.55 (m, 4H); 5.94–6.14 (m, 2H); 7.68–7.76 (m, 2H); 7.83 (d, 1H).

The crude ester (10 g, 38 mM) was dissolved in ethanol (20 ml) and added to a stirred suspension of SnCl$_2$.2H$_2$O (42.9 g, 0.19M) in ethanol (60 ml) under argon at ambient temperature. The mixture was heated to reflux for 30 minutes, cooled and poured onto ice. After making basic to pH 8 with an aqueous solution of sodium bicarbonate, the mixture was extracted with ethyl acetate. The combined extracts were washed with water and brine, dried over MgSO$_4$ and evaporated to give allyl 3-allyloxy-4-aminobenzoate (8.2 g).

NMR (CDCl$_3$): δ 4.22 (br, 2H); 4.57–4.63 (m, 2H); 4.75–4.79 (m, 2H); 5.22–5.47 (m, 4H); 5.93–6.15 (m, 2H); 6.67 (d, 1H); 7.48 (d, 1H); 7.58 (dd, 1H).

Preparation of the Pyrrolidin-4-ylthiol Side Chain

The cyclohexylamine salt of (2S,4S)-4-acetylthio-1-allyloxycarbonyl- 2-carboxypyrrolidine (2.5 g, 6.6 mM) was treated with a 2M aqueous solution of hydrochloric acid and extracted with ethyl acetate. The extract was washed with water and brine and dried over MgSO$_4$. Evaporation of the solvent gave the free acid.

Vilsmeier reagent was prepared by treatment of DMF (0.56 ml, 7.2 mM) in dichloromethane (35 ml) under argon with oxalyl chloride (0.58 ml, 6.6 mM) at −10° for 30 minutes. The (2S,4S)-4-acetylthio-1-allyloxycarbonyl-2-carboxypyrrolidine was added to this in one portion, followed by N-methylmorpholine (0.87 ml, 7.9 mM) and stirring continued for 30 minutes at −10°. After cooling to −20°, allyl 3-allyloxy-4-aminobenzoate (1.54 g, 6.6 mM) plus N-methyl morpholine (0.87 ml, 7.9 mM) dissolved in dichloromethane (20 ml) were added dropwise. The temperature was allowed to rise to 5° and stirring continued for 2 hours. After dilution with dichloromethane, the mixture was washed with a 2M aqueous solution of hydrochloric acid, water and a saturated aqueous solution of sodium bicarbonate. It was dried over $MgSO_4$ and the solvent evaporated. Crude material was purified by medium pressure chromatography using a gradient of diethyl ether (0 to 10%) in dichloromethane to give (2S,4S)-4-acetylthio-1-allyloxycarbonyl-2-(4-allyloxycarbonyl-2-allyloxyphenylcarbamoyl)pyrrolidine (2.7 g).

NMR ($CDCl_3$): δ 2.30 (s, 3H); 2.49 (br 1H); 2.63 (br, 1H); 3.40 (dd, 1H); 4.03 (quintet, 1H); 4.16 (dd, 1H); 4.56 (t, 1H); 4.62–4.67 (m, 4H); 4.79–4.83 (m, 2H); 5.18–5.48 (m, 6H); 5.94–6.16 (m, 3H); 7.56 (d, 1H); 7.72 (dd, 1H); 8.47 (d, 1H); 9.19 (br, 1H).

Conversion to the Pyrrolidin-4-ylthiol

The (2S,4S)-4-acetylthio-1-allyloxycarbonyl-2-(4-allyloxycarbonyl-2-allyloxyphenylcarbamoyl)pyrrolidine (1.3 g, 2.66 mM) was dissolved in allyl alcohol and the solution flushed with argon. A 1M aqueous solution of sodium hydroxide (2.66 ml, 1 mM) was added and the mixture was stirred at ambient temperature for 60 minutes. A 2M aqueous solution of hydrochloric acid (1.33 ml, 1 mM) was added and the pH adjusted to 8 with a dilute aqueous solution of sodium bicarbonate. The solvent was removed by evaporation and the residue partitioned between ethyl acetate and water. The organic layer was washed with a dilute aqueous solution of sodium bicarbonate, brine, and dried ($MgSO_4$). The solvent was evaporated to give (2S,4S)-1-allyloxycarbonyl-2-(4-allyloxycarbonyl-2-allyloxyphenylcarbamoyl)pyrrolidin-4-ylthiol as a gum. This could be used as such or optionally purified by medium pressure chromatography on silica.

NMR ($CDCl_3$): δ 1.84 (d, 1H); 2.38 (br 1H); 2.73 (br, 1H); 3.31–3.49 (m, 2H); 4.05–4.22 (br m, 1H); 4.51 (t, 1H); 4.59–4.68 (m, 4H); 4.78–4.84 (m, 2H); 5.08–5.47 (br + m, 6H); 5.77–6.17 (m, 3H); 7.58 (d, 1H); 7.72 (dd, 1H); 8.47 (d, 1H); 9.10 (br, 1H).

Preparation of Protected Carbapenems

A solution of allyl (1R,5R,6S,8R)-6-(1-hydroxyethyl)-1-methyl-2-diphenylphosphoryloxycarbapenem-3-carboxylate (930 mg, 1,9 mM) was dissolved in dry acetonitrile (6 ml) at 0°. (2S,4S)-1-Allyloxycarbonyl-2-(4-allyloxycarbonyl-2-allyloxyphenylcarbamoyl)pyrrolidin-4-ylthiol (850 mg, 1.9 mM) in acetonitrile (10 ml) was added and argon bubbled through the solution. After cooling to −20°, di-isopropylethylamine (258 mg, 2 mM) in acetonitrile (5 ml) was added dropwise. The temperature was allowed to rise to 5° over 2 hours and maintained at that temperature for 16 hours. The solvent was evaporated and the residue purified by medium pressure chromatography with gradient elution from dichloromethane to ethyl acetate to give allyl (1R,5S,6S,8R,2'S,4'S)-2-(1-allyloxycarbonyl-2-(4-allyloxycarbonyl-2-allyloxyphenylcarbamoyl)pyrrolidin-4-ylthio)-6-(1-hydroxyethyl)-1-methylcarbapenem-3-carboxylate as a gum (487 mg).

NMR ($CDCl_3$): δ 1.24 (d, 3H); 1.36 (d, 3H); 2.47 (br, 1H); 2.71 (br, 1H); 3.25,3.29 (dd overlapping m, 2H); 3.44 (dd, 1H); 3.79 (quintet, 1H); 4.13 (br m, 1H); 4.20–4.29 (m, 2H); 4.57 (t, 1H); 4.60–4.68 (m, 6H); 4.81 (m, 2H); 5.18–5.47 (m, 8H); 5.80–6.14 (m, 4H); 7.57 (d, 1H); 7.73 (dd, 1H); 8.46 (d, 1H); 9.05 (br, 1H).

Ms (+ve FAB): 696 $(M+H)^+$, 718 $(M+Na)^+$.

Allyl (1R,5R,6S,SR)-6-(1-hydroxyethyl)-1-methyl-2-diphenylphosphoryloxycarbapenem-3-carboxylate was prepared as follows:

To a solution of allyl (1R,5R,6S,8R)-6-(1-hydroxyethyl)-1-methyl-2-oxocarbapenem-3-carboxylate [prepared in situ from allyl 2-diazo-3-oxo-4-(R)-methyl-4-[(3S,4R)-3-(1-(R)-hydroxyethyl)-2-oxoazetidin-4-yl]-butanoate and rhodium octanoate: see for example EP-A-208889] and di-isopropylethylamine (1.1 equivalents) in acetonitrile, at 0° C., under an argon atmosphere, was added dropwise diphenyl chlorophosphate (1.1 equivalents). The solution was stirred at ambient temperature for 30 minutes to form the corresponding 2-diphenylphosphoryloxycarbapenem.

EXAMPLE 2

(1R,5S,6S,8R,2'S,4'S)-2-(2-(5-Carboxy-2-hydroxyphenylcarbamoyl)pyrrolidin-4-ylthio)-6-(1-hydroxyethyl)-1-methylcarbapenem-3-carboxylic acid was prepared from the corresponding allyl protected compound by the method described in example 1.

NMR δ 1.18 (d, 6H); 1.74 (m, 1H); 2.66 (m, part obscured, 2H); 3.21 (dd, 1H); 3.38–3.64 (m, 3H); 3.93–4.04 (m, 2H); 4.17 (dd, 1H); 6.96 (d, 1H); 7.58 (dd, 1H); 8.80 (d, 1H).

Ms (+ve FAB): 492 $(MH)^+$; 514 $(M+Na)^+$.

The starting material was prepared as follows:

4-Hydroxy-3-nitrobenzoic acid was allylated using the method described in example 1, except using 4-hydroxy-3-nitrobenzoic acid in place of 3-hydroxy-4-nitrobenzoic acid, to give allyl 4-allyloxy-3-nitrobenzoate.

NMR ($CDCl_3$): δ 4.74–4.86 (m, 4H); 5.28–5.57 (m, 4H); 5.93–6.13 (m, 2H); 7.12 (d, 1H); 8.21 (dd, 1H); 8.51 (d, 1H).

The above nitro compound was reduced by the method described in example 1, for the reduction of allyl 2-allyloxy-4-nitrobenzoate, except that the solvent was methanol, and using an aqueous solution of ammonia in place of sodium bicarbonate in the work-up, to give allyl 4-allyloxy-3-aminobenzoate.

NMR ($CDCl_3$): δ 3.72 (br, 2H); 4.58–4.65 (m, 2H); 4.74–4.80 (m, 2H); 5.22–5.46 (m, 4H); 5.94–6.14 (m, 2H); 6.79 (d, 1H); 7.42 (d, 1H); 7.47 (dd, 1H).

The above amine was condensed with (2S,4S)-4-acetylthio-1-allyloxycarbonyl-2-carboxypyrrolidine using the method described in example 1, except using the above amine in place of allyl 3-allyloxy-4-aminobenzoate to give (2S,4S)-1-allyloxycarbonyl-2-(2-allyloxy-5-allyloxycarbonylphenylcarbamoyl)pyrrolidin-4-ylthioacetate.

NMR ($CDCl_3$): δ 2.31 (s, 3H); 2.51 (br, 1H); 2.64 (br, 1H); 3.39 (dd, 1H); 4.03 (quintet, 1H); 4.16 (dd, 1H); 4.56 (t, 1H); 4.59–4.66 (m, 4H); 4.77–4.82 (m, 2H); 5.16–5.48 (m, 6H); 5.79–6.18 (m, 3H); 6.91 (d, 1H); 7.82 (dd, 1H); 8.98 (br, 1H); 9.05 (d, 1H).

The above thioacetate was deacetylated to the corresponding thiol, which was condensed without further purification with allyl (1R,5R,6S,8R)-6-(1-hydroxyethyl)-1-methyl-2-diphenylphosphoryloxycarbapenem-3-carboxylate, using the method described in example 1 for the preparation of protected carbapenems, to give allyl (1R,5S,6S,8R,2'S,4'S)-2-(1-allyloxycarbonyl-2-(2-allyloxy-5 -allyloxycarbonylphenylcarbamoyl)pyrrolidin-4-ylthio)-6-(1 -hydroxyethyl)-1-methylcarbapenem-3-carboxylate.

NMR (CDCl₃): δ 1.19 (d, 3H); 1.35 (d, 3H); 2.52 (br, 1H); 2.66 (br, 1H); 3.19–3.34 (dd overlapping m, 2H); 3.43 (dd, 1H); 3.84 (quintet, 1H); 4.11 (br m, 1H); 4.20–4.31 (m, 2H); 4.55 (t, 1H); 4.59–4.68 (m, 6H); 4.81 (m, 2H); 5.17–5.45 (m, 8H); 5.89–6.16 (m, 4H); 6.90 (d, 1H); 7.81 (dd, 1H); 8.90 (br, 1H); 9.06 (d, 1H).

Ms (+ve FAB): 696 (MH)⁺; 718 (M+Na)⁺.

EXAMPLE 3

(1R,5S,6S,8R,2'S,4'S)-2-(2-(2,5-Dicarboxyphenylcarbamoyl)pyrrolidin- 6-(1-hydroxyethyl)-1-methylcarbapenem-3-carboxylic acid was prepared from the corresponding allyl protected compound by the method described in example 1.

NMR δ 1.12 (d, 6H); 1.95 (m, part obscured, 1H); 2.82 (m, part obscured, 1H); 2.82 (m, part obscured, 1H); 2.99 (br m, 1H); 3.19 (dd, 1H); 3.38 (quintet, 1H); 3.64 (m, 1H); 3.82 (m, 1H); 3.94 (quintet, 1H); 4.16 (dd, 1H); 7.63 (dd, 1H); 8.05 (d, 2H); 9.04 (d, 1H).

Ms (+ve FAB): 520 (MH)⁺; 542 (M+Na)⁺.

The starting material was prepared as follows:

2-Nitrobenzene-1,4-dicarboxylic acid was allylated using the method described in example 1, except using 2-nitrobenzene-1,4-dicarboxylic acid in place of 3-hydroxy-4-nitrobenzoic acid, to give diallyl 2 -nitrobenzene-1,4-dicarboxylate.

NMR (CDCl₃): δ 4.84–4.91 (m, 4H); 5.31–5.48 (m, 4H); 5.93–6.12 (m, 2H); 7.62 (d, 1H); 8.34 (dd, 1H); 8.58 (d, 1H).

The above nitro compound was reduced by the method described in example 1, for the reduction of allyl 2-allyloxy-4-nitrobenzoate, except using an aqueous solution of ammonia in place of sodium bicarbonate in the work-up, to give diallyl 2-aminobenzene-1,4-dicarboxylate.

NMR (CDCl₃): δ 4.78–4.82 (m, 4H); 5.26–5.44 (m, 4H); 5.82 (br, 2H); 5.95–6.09 (m, 2H); 7.27 (dd, 1H); 7.36 (d, 1H); 7.95 (d, 1H).

The above amine was condensed with (2S,4S)-4-acetylthio-1 -allyloxycarbonyl-2-carboxypyrrolidine using the method described in example 1, except using the above amine in place of allyl 3-allyloxy-4-aminobenzoate to give (2S,4S)-1-allyloxycarbonyl-2-(2,5 -diallyloxycarbonylphenylcarbamoyl)pyrrolidin-4-ylthioacetate.

NMR (CDCl₃): δ 6 2.29 (s+br m, 4H); 2.81 (br, 1H); 3.54 (dd, 1H); 4.05 (quintet, 1H); 4.21 (dd, 1H); 4.49–4.68 (br m, 3H); 4.82–4.86 (m, 4H); 5.02–5.48 (br+m, 6H); 5.70–6.15 (br+m, 3H); 7.79 (dd, 1H); 8.14 (d, 1H); 9.38 (br s, 1H); 11.59 (br s, 1H).

The above thioacetate was deacetylated to the corresponding thiol, which was condensed without further purification with allyl (1R,5R,6S,8R)-6-(1-hydroxyethyl)-1-methyl-2 -diphenylphosphoryloxycarbapenem-3-carboxylate, using the method described in example 1 for the preparation of protected carbapenems, to give allyl (1R,5S,6S,8 R,2'S,4'S)-2-(1-allyloxycarbonyl-2-(2,5 -diallyloxycarbonylphenylcarbamoyl)pyrrolidin-4-ylthio)-6-(1-hydroxyethyl)-1-methylcarbapenem-3-carboxylate.

NMR (CDCl₃): δ 1.23 (d, 3H); 1.36 (d, 3H); 2.30 (m, 1H); 2.80 (br, 1H); 3.23, 3.29 (dd overlapping m, 2H); 3.59 (dd, 1H); 3.81 (br, 1H); 4.12 (br, 1H); 4.19–4.29 (m, 2H); 4.60 (m, 5H); 4.78–4.90 (m, 4H); 5.02–5.47 (br+m, 8H); 5.68–6.13 (br+m, 4H); 7.78 (d, 1H); 8.13 (d, 1H); 9.40 (s, 1H); 11.68 (s, 1H).

Ms (+ve FAB): 724 (MH)⁺; 746 (M+Na)⁺.

EXAMPLE 4

(1R,5S,6S,8R,2'S,4'S)-2-(2-(2,3-Dicarboxyphenylcarbamoyl)pyrrolidin-4 -ylthio)-6-(1-hydroxyethyl)-1-methylcarbapenem-3-carboxylic acid was prepared from the corresponding allyl protected compound by the method described in example 1.

NMR δ 1.12 (d, 6H); 1.77 (m, part obscured, 1H); 2.68–2.81 (m, part obscured, 2H); 3.19 (dd, 1H); 3.37 (m, 1H); 3.56 (t, 1H); 3.69 (t, 1H); 3.94 (quintet, 1H); 4.12–4.19 (m, 2H); 7.75 (m, part obscured, 1H); 7.88 (m, part obscured, 1H); 8.25 (dd, 1H).

Ms (+ve FAB): 520 (MH)⁺, 542 (M+Na)⁺.

The starting material was prepared as follows:

3-Nitrobenzene-1,2-dicarboxylic acid was allylated using the method described in example 1, except that 3-nitrobenzene-1,2-dicarboxylic acid was used in place of 3-hydroxy-4-nitrobenzoic acid, and the reaction was carried out at 95° for 1 hour, to give diallyl 3 -nitrobenzene-1,2-dicarboxylate.

NMR (CDCl₃): δ 4.79–4.86 (m, 2H); 4.88–4.93 (m, 2H); 5.29–5.47 (m, 4H); 5.91–6.16 (m, 2H); 7.69 (t, 1H); 8.34–8.41 (m, 2H).

The above nitro compound was reduced by the method described in example 1, for the reduction of allyl 3-allyloxy-4-nitrobenzoate, except using an aqueous solution of ammonia in place of sodium bicarbonate in the work-up, to give diallyl 3-aminobenzene-1,2-dicarboxylate.

NMR (CDCl₃): δ 4.70–4.74 (m, 4H); 5.01 (br, 2H); 5.23–5.40 (m, 4H); 5.89–6.03 (m, 2H); 6.79 (dd, 1H); 7.92 (dd, 1H); 7.24 (t, 1H).

The above amine was condensed with (2S,4S)-4-acetylthio-1 -allyloxycarbonyl-2-carboxypyrrolidine using the method described in example 1, except using the above amine in place of allyl 3-allyloxy-4-aminobenzoate to give (2S,4S)-1-allyloxycarbonyl-2-(2,3 -diallyloxycarbonylphenylcarbamoyl)pyrrolidin-4-ylthioacetate.

NMR (CDCl₃): δ 2.29 (s, 3H); 2.35 (br, 1H); 2.75 (br, 1H); 3.49 (dd, 1H); 4.04 (quintet, 1H); 4.17 (dd, 1H); 4.52 (dd, 1H); 4.65 (br d, 2H); 4.72–4.77 (m, 4H); 5.08–5.43 (br+m, 6H); 5.76–6.09 (br+m, 3H); 7.44–7.58 (m, 3H); 8.60 (dd, 1H); 10.12 (br s, 1H).

The above thioacetate was deacetylated to the corresponding thiol, which was condensed without further purification with allyl (1R,5R,6S,8R)-6-(1-hydroxyethyl)-1-methyl-2 -diphenylphosphoryloxycarbapenem-3-carboxylate, using the method described in example 1 for the preparation of protected carbapenems, to give allyl (1R,5S,6S,8 R,2'S,4'S)-2-(1-allyloxycarbonyl-2-(2,3 -diallyloxycarbonylphenylcarbamoyl)pyrrolidin-4-ylthio)-6-(1-hydroxyethyl)-1-methylcarbapenem-3-carboxylate.

NMR (CDCl₃): δ 1.21 (d, 3H); 1.35 (d, 3H); 2.33 (br, 1H); 2.75 (br, 1H); 3.23, 3.30 (dd overlapping m, 2H); 3.51 (dd, 1H); 3.79 (br m, 1H); 4.10 (br, 1H); 4.18–4.29 (m, 2H); 4.52 (t, 1H); 4.60–4.66 (m, 4H); 4.73 (m, 4H); 5.16–5.40 (m, 8H); 5.79–6.05 (m, 4H); 7.43 (dd, 1H); 7.54 (t, 1H); 8.62 (d, 1H).

MS (+ve FAB): 724 (MH)⁺; 746 (M+Na)⁺.

EXAMPLE 5

(1R,5S,6S,8R,2'S,4'S)-2-(2-(2-Carboxyphenylcarbamoyl)pyrrolidin-4 -ylthio)-6-(1-hydroxyethyl)-1-methylcarbapenem-3-carboxylic acid was prepared from the corresponding allyl protected compound by the method described in example 1.

NMR δ 1.18 (d, 6H); 1.81 (m, part obscured, 1H); 2.72–2.87 (m, part obscured, 2H); 3.23 (dd, 1H); 3.47 (quintet, 1H); 3.50 (m, 1H); 3.74 (t, 1H); 3.99 (quintet, 1H); 4.14–4.23 (m, 2H); 7.13 (td, 1H); 7.52 (td, 1H); 8.01 (dd, 1H); 8.54 (dd, 1H).

MS (+ve FAB): 476 (MH)$^+$; 498 (M+Na)$^+$.

The starting material was prepared as follows:

2-Nitrobenzoic acid was allylated using the method described in example 1, except that 2-nitrobenzoic acid was used in place of 3-hydroxy-4-nitrobenzoic acid, to give allyl 2-nitrobenzoate.

NMR (CDCl$_3$): δ 4.80–4.85 (m, 4H); 5.28–5.44 (m, 4H); 5.89–6.09 (m, 2H); 7.58–7.79 (m, 3H); 7.89–7.94 (m, 1H).

The above nitro compound was reduced by the method described in example 1, for the reduction of allyl 3-allyloxy-4-nitrobenzoate, except using an aqueous solution of ammonia in place of sodium bicarbonate in the work-up, to give allyl 2-aminobenzoate.

NMR (CDCl$_3$): δ 4.76–4.80 (m, 4H); 5.24–5.44 (m, 4H); 5.68 (br, 2H); 5.94–6.13 (m, 2H); 6.60–6.68 (m, 2H); 7.26 (td, 1H); 7.90 (dd, 1H).

The above amine was condensed with (2S,4S)-4-acetylthio-1-allyloxycarbonyl-2-carboxypyrrolidine using the method described in example 1, except using the above amine in place of allyl 3-allyloxy-4-aminobenzoate to give (2S,4S)-1-allyloxycarbonyl-2-(2-allyloxycarbonylphenylcarbamoyl)pyrrolidin-4-ylthioacetate.

NMR (CDCl$_3$): δ 2.28 (s+m, 4H); 2.85 (br, 1H); 3.53 (dd, 1H); 4.04 (quintet, 1H); 4.21 (dd, 1H); 4.46–4.68 (br m, 3H); 4.81 (d, 2H); 4.97–5.47 (br+m, 4H); 5.67–6.12 (br+m, 2H); 7.11 (t, 1H); 7.56 (td, 1H); 8.08 (dd, 1H); 8.72 (d, 1H); 11.61 (br s, 1H).

The above thioacetate was deacetylated to the corresponding thiol, which was condensed without further purification with allyl (1R,5R,6S,8R)-6-(1-hydroxyethyl)-1-methyl-2-diphenylphosphoryloxycarbapenem-3-carboxylate, using the method described in example 1 for the preparation of protected carbapenems, to give allyl (1R,5S,6S,8R,2'S,4'S)-2-(1-allyloxycarbonyl-2-(2-allyloxycarbonylphenylcarbamoyl)pyrrolidin-4-ylthio)-6-(1-hydroxyethyl)-1-methylcarbapenem-3-carboxylate.

NMR (CDCl$_3$): δ 1.24 (d, 3H); 1.35 (d, 3H); 2.29 (m, 1H); 2.83 (br, 1H); 3.24, 3.32 (dd overlapping m, 2H); 3.76 (br, 1H); 4.12 (br m, 1H); 4.18–4.31 (m, 2H); 4.60 (br m, 5H); 4.78 (br m, 2H); 5.04–5.46 (br+m, 6H); 5.65–6.02 (br+m, 3H); 7.02 (t, 1H); 7.58 (t, 1H); 8.08 (d, 1H); 8.73 (d, 1H); 11.72 (s, 1H).

Ms (+ve FAB): 640 (MH)$^+$; 662 (M+Na)$^+$.

EXAMPLE 6

(1R,5S,6S,8R,2'S,4'S)-2-(2-(2-Carboxy-3-methylphenylcarbamoyl)pyrrolidin-4-ylthio)-6-(1-hydroxyethyl)-1-methylcarbapenem-3-carboxylic acid, disodium salt To a solution of allyl (1R,5S,6S,8R,2'S,4'S)-2-(1-allyloxycarbonyl-2-(2-allyloxycarbonyl-3-methylphenylcarbamoyl)pyrrolidin-4-ylthio)-6-(1-hydroxyethyl)-1-methylcarbapenem-3-carboxylate (250 mg, 0.38 mM) and Meldrum's acid (331 mg, 2.30 mM) in a mixture of DMSO (3 ml) and THF (1 ml), under an argon atmosphere, was added tetrakis(triphenylphosphine)palladium (44 mg, 0.038 mM). The solution was stirred under argon with protection from light for 1 hour. A solution of sodium 2-ethylhexanoate (126 mg, 0.76 mM) in THF (3 ml) was added, and the mixture poured into THF (30 ml), with vigorous stirring. The resultant precipitate was centrifuged, and supernatant removed. The product was washed twice by resuspension in THF followed by centrifugation, and finally dried under high vacuum to give the title product (153 mg, 75%).

NMR δ 1.11 (d, 6H); 1.70 (m, part obscured, 1H); 2.32 (s, 3H); 2.78 (m, 1H); 2.95 (dd, 1H); 3.19 (dd, 1H); 3.35 (quintet, 1H); 3.62 (dd, 1H); 3.79 (t, 1H); 3.96 (quintet, 1H); 4.14 (dd, 1H); 4.25 (t, 1H); 6.98 (d, 1H); 7.23 (t, 1H); 7.68 (d, 1H).

Ms (+ve FAB): 512 (MH)$^+$, (Na salt)$^+$; 534 (Na$_2$ salt)$^+$.

The starting material was prepared as follows:

2-Methyl-6-nitrobenzoic acid was allylated using the method described in example 1, except using 2-methyl-6-nitrobenzoic acid in place of 3-hydroxy-4-nitrobenzoic acid to give allyl 2-methyl-6-nitrobenzoate.

NMR (CDCl$_3$): δ 2.43 (s, 3H); 4.87 (d, 2H); 5.30–5.48 (m, 2H); 5.94–6.14 (m, 1H); 7.47 (t, 2H); 7.55 (d, 1H); 8.00 (s, 1H).

Allyl 2-amino-6-methylbenzoate

Stannous chloride dihydrate (15.3 g, 67.8 mM) was suspended in methanol (25 ml), and a solution of allyl 2-methyl-6-nitrobenzoate (3.0 g, 13.6 mM) in methanol (5 ml) was added. The mixture was heated at reflux for 1 hour, cooled, and solvent removed. The residue was treated with ethyl acetate (100 ml), made basic with 880 ammonia and diluted with water (50 ml). The organic layer was decanted from the slurry of tin salts, which was extracted with two further portions of ethyl acetate. The combined organic extracts were washed with dilute ammonia, water, brine, and dried over MgSO$_4$, to give allyl 2-amino-6-methylbenzoate as an oil (1.94 g, 75%).

NMR (CDCl$_3$): δ 2.45 (s, 3H); 4.46 (br, 2H); 4.81 (dt, 2H); 5.25–5.45 (m, 2H); 5.94–6.14 (m, 1H); 6.53 (d, 2H); 7.08 (t, 1H).

Preparation of side chain pyrrolidin-4-ylthioacetate (2S,4S)-4-Acetylthio-1-allyloxycarbonyl-2-carboxypyrrolidine (2.3 g, 8.6 mM), allyl 2-amino-6-methylbenzoate (1.5 g, 7.8 mM), and 2-ethoxy-1-ethoxycarbonyl-1,2-dihydroquinoline (2.5 g, 10 mM) were dissolved in toluene (30 ml) and stirred for 18 hours at ambient temperature. The reaction mixture was diluted with ethyl acetate (150 ml) and washed with a 2M aqueous solution of HCl (3 by 30 ml), water, a saturated aqueous solution of NaHCO$_3$, and brine. Drying over MgSO$_4$ and evaporation of the solvent gave (2S,4S)-4-acetylthio-1-allyloxycarbonyl-2-(2-allyloxycarbonyl-3-methylphenylcarbamoyl)pyrrolidine as a gum (3.4 g, 97%) which was used without further purification.

NMR (CDCl$_3$): δ 2.29 (s overlapping m, 4H); 2.47 (s, 3H); 2.75 (br, 1H); 3.49 (dd, 1H); 4.04 (quintet, 1H); 4.17 (m, 1H); 4.49 (m, 1H); 4.63 (d, 2H); 4.83 (dt, 2H); 5.10–5.45 (m, 4H); 5.27–6.11 (m, 2H); 6.99 (d, 1H); 7.35 (t, 1H); 8.26 (d, 1H); 10.22 (br, 1H).

The above thioacetate was deacetylated as described in example 1 for 4-acetylthio-1-allyloxycarbonyl-2-(4-allyloxycarbonyl-2-allyoxyphenylcarbamoyl)pyrrolidine, to give the thiol.

The thiol was used without further purification and condensed with allyl (1R,5R,6S,8R)-6-(1-hydroxyethyl)-1-methyl-2-diphenylphosphoryloxycarbapenem-3-carboxylate, using the method described in example 1, for the preparation of protected carbapenems, to give allyl (1R,5S,6S,8R,2'S,4'S)-2-(1-allyloxycarbonyl-2-(2-allyloxycarbonyl-3 -methylphenylcarbamoyl)pyrrolidin-4-ylthio)-6-(1-hydroxyethyl)-1 -methylcarbapenem-3-carboxylate.

NMR (CDCl$_3$): δ 1.24 (d, 3H); 1.35 (d, 3H); 2.29 (br, 1H); 2.76 (br, 1H); 3.24 (dd, 1H); 3.29 (quintet, 1H); 3.50 (dd, 1H); 3.75 (quintet, 1H); 4.06–4.19 (overlapping m, 3H); 4.50 (t, 1H); 4.63 (d, 4H); 4.81 (d, 2H); 5.17–5.47 (m, 6H); 5.78–6.13 (m, 3H); 6.98 (d, 1H); 7.35 (t, 1H); 8.29 (d, 1H); 10.39 (br, 1H).

Ms (+ve FAB): 654 (MH)$^+$; 676 (M+Na)$^+$.

EXAMPLE 7

(1R,5S,6S,8R,2'S,4'S)-2-(2-(2-Carboxy-4 -methylphenylcarbamoyl)pyrrolidin-4-ylthio)-6-(1-hydroxyethyl)-1-methylcarbapenem-3-carboxylic acid, disodium salt was prepared from the allyl protected compound using the method described in example 6.

Partial NMR δ 1.13 (d, 3H); 1.16 (d, 3H); 3.19 (dd, 1H); 3.99 (m, 2H); 4.15 (dd, 1H); 7.28 (dd, 1H); 7.80 (d, 1H); 8.45 (d, 1H).

Ms (+ve FAB): 512 (MH)$^+$, (Na salt)$^+$; 534 (Na$_2$ salt)$^+$.

The starting material was prepared as follows:

5-Methyl-2-nitrobenzoic acid was allylated using the method described in example 1 except using 5-methyl-2-nitrobenzoic acid in place of 3-hydroxy-4-nitrobenzoic acid, to give allyl 5-methyl-2-nitrobenzoate.

NMR (CDCl$_3$): δ 2.47 (s, 3H); 4.82 (dt, 2H); 5.28–5.43 (m, 2H); 5.92–6.08 (m, 1H); 7.39 (dd, 2H); 7.49 (d, 1H); 7.86 (d, 1H).

The above nitro compound was reduced by the method described in example 6, for the reduction of allyl 2-methyl-6-nitrobenzoate to give allyl 2-amino-5-methylbenzoate.

NMR (CDCl$_3$): δ 2.23 (s, 3H); 4.78 (dt, 2H); 5.20 (br, 2H); 5.24–5.44 (m, 2H); 5.94–6.14 (m, 1H); 6.60 (d, 1H); 7.09 (dd, 1H); 7.68 (d, 1H).

The above amine was condensed with (2R,4S)-4-acetylthio-1 -allyloxycarbonyl-2-carboxypyrrolidine using the method described in example 6, except using the above amine in place of allyl 2-amino-6-methylbenzoate and purifying by chromatography using a gradient of dichloromethane/diethyl ether (100:0 to 90:10) to give (2S,4S)-1-allyloxycarbonyl-2 (2-allyloxycarbonyl-4-methylphenylcarbamoyl)pyrrolidin-4-ylthioacetate.

NMR (CDCl$_3$): δ 2.28, 2.34 (2 s overlapping m, 7H); 2.80 (br, 1H); 3.54 (dd, 1H); 4.03 (quintet, 1H); 4.19 (br m, 1H); 4.51 (br, 1H); 4.62 (br, 2H) 4.79 (d, 2H); 5.18 (br, 2H); 5.29–5.46 (m, 2H); 5.82 (br, 1H); 5.95–6.11 (m, 1H); 7.36 (dd, 1H); 7.86 (d, 1H); 8.51 (d, 1H); 11.52 (br s, 1H).

The above thioacetate was deacetylated to the corresponding thiol, which was condensed without further purification with allyl (1R,5R,6S,8R)-6-(1-hydroxyethyl)-1-methyl-2 -diphenylphosphoryloxycarbapenem-3-carboxylate, using the method described in example 1 for the preparation of protected carbapenems to give allyl (1R,5S,6S,8R,2'S,4'S)-2-(1-allyloxycarbonyl-2-(2-allyloxycarbony- 4-methylphenylcarbamoyl)pyrrolidin-4-ylthio)-6-(1-hydroxyethyl)-1 -methylcarbapenem-3-carboxylate.

NMR (CDCl$_3$): δ 1.23 (d, 3H); 1.35 (d, 3H); 1.93 (br, 1H); 2.34 (s, 3H); 2.80 (br, 1H); 3.24 (dd, 1H); 3.32 (m, 1H); 3.57 (dd, 1H); 3.75 (br, 1H); 4.15–4.29 (overlapping m, 3H); 4.61 (d+m, 4H); 4.78 (m, 2H); 5.00–5.46 (m, 6H); 5.76–6.13 (m, 3H); 7.36 (dd, 1H); 7.86 (d, 1H); 8.59 (d, 1H); 11.58 (br, 1H).

Ms (+ve FAB): 654 (MH)$^+$; 676 (M+Na)$^+$.

EXAMPLE 8

(1R,5S,6S,8R,2'S,4'S)-2-(2-(2-Carboxy-4 -chlorophenylcarbamoyl)pyrrolidin-4-ylthio)-6-(1-hydroxyethyl)-1-methylcarbapenem-3-carboxylic acid, disodium salt was prepared from the corresponding allyl protected compound using the method described in example 6, except that the product did not precipitate on dilution with THF alone, but needed further dilution with double the volume of diethyl ether.

NMR δ 1.21 (d, 6H); 2.03 (m, part obscured, 1H); 2.91 (quintet, 1H); 3.11 (dd, 1H); 3.28 (dd, 1H); 3.45 (quintet, 1H); 3.64–3.76 (m, 1H); 3.91 (t, 1H); 4.05 (t, 1H); 4.23 (dd, 1H); 4.40 (t, 1H); 7.49 (dd, 1H); 8.03 (d, 1H); 8.54 (d, 1H).

Ms (+ve FAB): 532/534 (MH)$^+$, (Na salt)$^+$; 554/556 (Na$_2$ salt)$^+$.

The starting material was prepared as follows:

5-Chloro-2-nitrobenzoic acid was allylated using the method described in example 1, except using 5-chloro-2-nitrobenzoic acid in place of 3-hydroxy-4-nitrobenzoic acid to give allyl 5-chloro-2-nitrobenzoate.

NMR (CDCl$_3$): δ 4.83 (dt, 2H); 5.30–5.45 (m, 2H); 5.89–6.08 (m, 1H); 7.59 (dd, 1H); 7.70 (d, 1H); 7.81 (d, 1H).

The above nitro compound was reduced by the method described in example 6, for the reduction of allyl 2-methyl-6-nitrobenzoate, to give allyl 2-amino-5-chlorobenzoate.

NMR (CDCl$_3$): δ 4.78 (dt, 2H); 5.27–5.44 (m, 2H); 5.60 (br, 2H); 5.93–6.13 (m, 1H); 6.60 (d, 1H); 7.21 (dd, 1H); 7.86 (d, 1H).

The above amine was condensed with (2S,4S)-4-acetylthio-1 -allyloxycarbonyl-2-carboxypyrrolidine using the method described in example 1, except using the above amine in place of allyl 3-allyloxy-4-aminobenzoate to give (2S,4S)-1-allyloxycarbonyl-2-(2 -allyloxycarbonyl-4-chlorophenylcarbamoyl)pyrrolidin-4-ylthioacetate.

NMR (CDCl$_3$): δ 2.28 (s overlapping m, 4H); 2.78 (br, 1H); 3.52 (dd, 1H); 4.03 (quintet, 1H); 4.19 (dd, 1H); 4.45–4.70 (br m, 3H); 4.81 (d, 2H); 5.21 (br, 2H); 5.29–5.46 (m, 2H); 5.83 (br, 1H); 5.91–6.11 (m, 1H); 7.50 (dd, 1H); 8.02 (d, 1H); 8.72 (d, 1H); 11.54 (br s, 1H).

Ms (+ve FAB): 467/469 (MH)$^+$.

The above thioacetate was deacetylated to the corresponding thiol, which was condensed without further purification with allyl (1R,5R,6S,8R)-6-(1-hydroxyethyl)-1-methyl-2 -diphenylphosporyloxycarbapenem-3-carboxylate, using the method described in example 1 for the preparation of protected carbapenems to give allyl (1R,5S,6S,8R,2'S,4'S)-2-(1-allyloxycarbonyl-2-(2-allyloxycarbonyl- 4-chlorophenylcarbamoyl)pyrrolidin-4-ylthio)-6-(1-hydroxyethyl)-1 -methylcarbapenem-3-carboxylate.

NMR (CDCl$_3$): δ 1.23 (d, 3H); 1.35 (d, 3H); 2.28 (quintet, 1H); 2.81 (br, 1H); 3.25 (dd, 1H); 3.30 (t, 1H); 3.58 (dd, 1H); 3.77 (br, 1H); 4.13 (br, 1H); 4.19–4.30 (overlapping m, 2H); 4.51–4.86 (m, 7H); 5.05–5.45 (m, 6H); 5.70–6.09 (m, 3H); 7.50 (dd, 1H); 8.02 (d, 1H); 8.71 (d, 1H); 11.61 (s, 1H).

Ms (+ve FAB): 674/676 (MH)$^+$; 696/698 (M+Na)$^+$.

EXAMPLE 9

(1R,5S,6S,8R,2'S,4'S)-2-(2-(2-Carboxy-6 -hydroxyphenylcarbamoyl)pyrrolidin-4-ylthio)-6-(1-hydroxyethyl)-1-methylcarbapenem-3-carboxylic acid was prepared from the corresponding allyl protected compound by the method described in example 1, except that the resulting crude acid was dissolved in water and purified by chromatography on CHP20P resin, eluting with water.

NMR δ 1.16 (d, 6H); 1.82 (m, part obscured, 1H); 2.83 (m, part obscured, 2H); 3.23 (dd, 1H); 3.42 (quintet, 1H); 3.59 (m, 1H); 3.72 (t, 1H); 4.99 (quintet, 1H); 4.20 (dd overlapping m, 2H); 7.09 (dd, 1H); 7.15 (t, 1H); 7.36 (d, 1H).

Ms (+ve FAB): 492 (MH)$^+$; 514 (Na salt)$^+$.

The starting material was prepared as follows:

3-Hydroxy-2-nitrobenzoic acid was allylated using the method described in example 1, except using 3-hydroxy-2-nitrobenzoic acid in place of 3-hydroxy-4-nitrobenzoic acid to give allyl 3-allyloxy-2-nitrobenzoate.

NMR (CDCl$_3$): δ 4.66 (dt, 2H); 4.79 (dt, 2H); 5.28–5.44 (m, 4H); 5.87–6.08 (m, 1H); 7.24 (dd, 2H); 7.51 (t, 1H); 7.62 (dd, 1H).

Ms (CI): 264 (MH)$^+$; 281 (M+NH$_4$)$^+$.

The above nitro compound was reduced by the method described in example 6, for the reduction of allyl 2-methyl-6-nitrobenzoate, except that the solvent used was ethanol, to give allyl 3-allyloxy-2-aminobenzoate.

NMR (CDCl$_3$): δ 4.57 (dt, 2H); 4.78 (dt, 2H); 5.24–5.44 (m, 4H); 5.90–6.15 (m overlapping br, 2H); 6.54 (t, 1H); 6.85 (dd, 1H); 7.52 (dd, 1H).

Ms (CI): 234 (MH)$^+$.

The above amine was condensed with (2S,4S)-4-acetylthio-1-allyloxycarbonyl-2-carboxypyrrolidine using the method described in example 1, except using the above amine in place of allyl 3-allyloxy-4-amino benzoate to give (2S,4S)-1-allyloxycarbonyl-2-(2-allyloxy-6-allyloxycarbonylphenylcarbamoyl)pyrrolidin-4-ylthioacetate.

NMR (CDCl$_3$): δ 2.31 (s overlapping br m, 4H); 2.72 (br, 1H); 3.40 (br t, 1H); 3.98 (quintet, 1H); 4.22 (br t, 1H); 4.53 (br, 1H); 4.57–4.68 (br m, 4H); 4.76 (m, 2H); 5.21 (br, 2H); 5.22–5.45 (m, 4H); 5.85 (br, 1H); 5.92–6.13 (m, 2H); 7.07 (dd, 1H); 7.17 (t, 1H); 7.46 (dd, 1H); 8.95 (br d, 1H).

Ms (+ve FAB): 489 (MH)$^+$; 511 (M+Na)$^+$.

The above thioacetate was deacetylated to the corresponding thiol, which was condensed without further purification with allyl (1R,8R,6S,8R)-6-(1-hydroxyethyl)-1-methyl-2-diphenylphosphoryloxycarbapenem-3-carboxylate, using the method described in example 1 for the preparation of protected carbapenems, to give allyl (1R,5S,6 S,8R,2'S,4'S)-2-(1-allyloxycarbonyl-2-(2-allyloxy-6-allyloxycarbonylphenylcarbamoyl)pyrrolidin-4-ylthio)-6-(1-hydroxyethyl)-1-methylcarbapenem-3-carboxylate.

NMR (CDCl$_3$): δ 1.25 (d, 3H); 1.35 (d, 3H); 2.31 (br, 1H); 2.75 (br, 1H); 3.24 (dd, 1H); 3.33 (t, 1H); 3.44 (t, 1H); 3.66 (quintet, 1H); 4.10–4.20 (m, 3H); 4.50 (t, 1H); 4.56–4.78 (m, 8H); 5.14–5.45 (m, 8H); 5.78–6.13 (m, 4H); 7.08 (dd, 1H); 7.18 (t, 1H); 7.48 (dd, 1H); 8.93 (br s, 1H).

Ms (+ve FAB): 696 (MH)$^+$; 718 (M+Na)$^+$.

EXAMPLE 10

(1R,5S,6S,8R,2'S,4'S)-2-(2-(2-Carboxy-6-chlorophenylcarbamoyl)pyrrolidin-4-ylthio)-6-(1-hydroxyethyl)-1-methylcarbapenem-3-carboxylic acid, disodium salt was prepared from the corresponding allyl protected compound using the method described in example 6.

NMR δ 1.21 (d, 6H); 2.05 (m, 1H); 2.98 (quintet, 1H); 3.17 (dd, 1H); 3.27 (dd, 1H); 3.42 (quintet, 1H); 3.75 (dd, 1H); 3.95 (t, 1H); 4.04 (quintet, 1H); 4.23 (dd, 1H); 4.48 (t, 1H); 7.39 (t, 1H); 7.69 (dd, 1H); 7.83 (dd, 1H).

Ms (+ve FAB): 510/512 (MH)$^+$; 532/534 (MH)$^+$, (Na salt)$^+$; 554/556 (Na$_2$ salt)$^+$.

The starting material was prepared as follows:

3-Chloro-2-nitrobenzoic acid was allylated using the method described in example 1, except using 3-chloro-2-nitrobenzoic acid in place of 3-hydroxy-4-nitrobenzoic acid to give allyl 3-chloro-2-nitrobenzoate.

NMR (CDCl$_3$): δ 4.81 (dt, 2H); 5.29–5.45 (m, 2H); 5.87–6.07 (m, 1H); 7.52 (t, 2H); 7.71 (dd, 1H); 8.00 (dd, 1H):

Ms (CI): 259/261 (M+NH$_4$)$^+$.

The above nitro compound was reduced by the method described in example 6, for the reduction of allyl 2-methyl-6-nitrobenzoate, except that the solvent was ethanol, to give allyl 2-amino-3-chlorobenzoate.

NMR (CDCl$_3$): δ 4.80 (dt, 2H); 5.26–5.44 (m, 2H); 5.95–6.11 (m, 1H); 6.25 (br, 2H); 6.61 (t, 1H); 7.40 (dd, 1H); 7.86 (dd, 1H).

The above amine was condensed with (2S,4S)-4-acetylthio-1-allyloxycarbonyl-2-carboxypyrrolidine using the method described in example 1, except using the above amine in place of allyl 3-allyloxy-4-aminobenzoate, to give (2S,4S)-1-allyloxycarbonyl-2-(2-allyloxycarbonyl-6-chlorophenylcarbamoyl)pyrrolidin-4-ylthioacetate.

NMR (CDCl$_3$): δ 2.32 (s, 3H); 2.38 (br, 1H); 2.72 (br, 1H); 3.43 (dd, 1H); 3.99 (quintet, 1H); 4.22 (dd, 1H); 4.56 (br t, 1H); 4.66 (m, 2H) 4.78 (dt, 2H); 5.17–5.44 (m, 4H); 5.87 (br, 1H); 5.91–6.11 (m, 1H); 7.26 (t, 1H); 7.59 (dd, 1H); 7.82 (dd, 1H); 9.25 (br, 1H).

Ms (+ve FAB): 467/469 (MH)$^+$; 489/491 (M+Na)$^+$.

The above thioacetate was deacetylated to the corresponding thiol, which was condensed without further purification with allyl (1R,5R,6 S,8R)-6-(1-hydroxyethyl)-1-methyl-2-diphenylphosphoryloxycarbapenem-3-carboxylate, using the method described in example 1 for the preparation of protected carbapenems, to give allyl (1R,5S,6S,8R,2'S,'S)-2-(1-allyloxycarbonyl-2-(2-allyloxycarbonyl-6-chlorophenylcarbamoyl)pyrrolidin-4-ylthio)-6-(1-hydroxyethyl)-1-methylcarbapenem-3-carboxylate.

NMR (CDCl$_3$): δ 1.23 (d, 3H); 1.33 (d, 3H); 2.32 (br, 1H); 2.72 (br, 1H); 3.23 (dd, 1H); 3.31 (quintet, 1H); 3.45 (t, 1H); 3.69 (dd, 1H); 4.12–4.26 (overlapping m, 3H); 4.53 (t, 1H); 4.58–4.79 (m, 6H); 5.16–5.43 (m, 6H); 5.81–6.17 (m, 3H); 7.21 (t, 1H); 7.57 (dd, 1H); 7.82 (br d, 1H); 9.17 (br, 1H).

Ms (+ve FAB): 674/676 (MH)$^+$; 696/698 (M+Na)$^+$.

EXAMPLE 11

(1R,5S,6S,8R,2'S,4'S)-2-(2-(2-Carboxy-6-methylphenylcarbamoyl)pyrrolidin-4-ylthio)-6-(1-hydroxyethyl)-1-methylcarbapenem-3-carboxylic acid, disodium salt was prepared from the corresponding allyl protected compound using the method described in example 6.

NMR δ 1.24 (d, 3H); 1.25 (d, 3H); 2.21, 2.28 (m overlapped by s, 4H); 3.10 (quintet, 1H); 3.20 (dd, 1H); 3.34–3.48 (overlapping m, 2H); 3.91 (dd, 1H); 4.03–4.17 (overlapping m, 2H); 4.27 (dd, 1H); 4.72 (t, 1H); 7.32 (t, 1H); 7.50 (br d, 1H); 7.79 (dd, 1H).

Ms (+ve FAB): 490 (MH)$^+$; 512 (MH)$^+$, (Na salt)$^+$; 534 (Na$_2$ salt)$^+$.

The starting material was prepared as follows:

3-Methyl-2-nitrobenzoic acid was allylated using the method described in example 1, except using 3-methyl-2-nitrobenzoic acid in place of 3-hydroxy-4-nitrobenzoic acid to give allyl 3-methyl-2-nitrobenzoate.

NMR (CDCl$_3$): δ 2.36 (s, 3H); 4.79 (dt, 2H); 5.27–5.45 (m, 2H); 5.88–6.07 (m, 1H); 7.45 (t, 2H); 7.51 (dd, 1H); 7.87 (dd, 1H).

The above nitro compound was reduced by the method described in example 6, for the reduction of allyl 2-methyl-6-nitrobenzoate, to give allyl 2-amino-6-methylbenzoate.

NMR (CDCl$_3$): δ 2.17 (s, 3H); 4.79 (dt, 2H); 5.22–5.45 (m, 2H); 5.88–6.13 (m, 1H); 6.59 (t, 1H); 7.19 (dd, 1H); 7.82 (dd, 1H).

The above amine was condensed with (2S,4S)-4-acetylthio-1-allyloxycarbonyl-2-carboxypyrrolidine using the method described in example 1, except using the above amine in place of allyl 3-allyloxy-4-aminobenzoate to give (2S,4S)-1-allyloxycarbonyl-2-(2-allyloxycarbonyl-6-methylphenylcarbamoyl)pyrrolidin-4-ylthioacetate.

NMR (CDCl$_3$): δ 2.29, 2.31 (2 s overlappping m, 7H); 2.78 (br, 1H); 3.51 (dd, 1H); 4.02 (quintet, 1H); 4.23 (br m, 1H); 4.54 (br t, 1H); 4.65 (br d, 2H) 4.78 (dt, 2H); 5.23 (br m, 2H); 5.26–5.45 (m, 2H); 5.88 (br, 1H); 5.92–6.12 (m, 1H); 7.20 (t, 1H); 7.43 (d, 1H); 7.82 (d, 1H); 9.66 (br s, 1H).

Ms (+ve FAB): 447 (MH)$^+$; 469 (M+Na)$^+$.

The above thioacetate was deacetylated to the corresponding thiol, which was condensed without further purification with allyl (1R,5R,6S,8R)-6-(1-hydroxyethyl)-1-methyl-2-diphenylphosphoryloxycarbapenem-3-carboxylate, using the method described in example 1 for the preparation of protected carbapenems to give allyl (1R,5S,6S,8R,2'S,4'S)-2-(1-allyloxycarbonyl-2-(2-allyloxycarbonyl-6-methylphenylcarbamoyl)pyrrolidin-4-ylthio)-6-(1-hydroxyethyl)-1-methylcarbapenem-3-carboxylate.

NMR (CDCl$_3$): δ 1.25 (d, 3H); 1.33 (d, 3H); 2.26 (s overlapping br m, 4H); 2.79 (br, 1H); 3.23 (dd, 1H); 3.32 (quintet, 1H); 3.54 (dd, 1H); 3.68 (br, 1H); 4.21 (dd overlapping m, 3H); 4.52 (t, 1H); 4.58–4.79 (m, 6H); 5.15–5.43 (m, 6H); 5.83–6.07 (m, 3H); 7.17 (t, 1H); 7.42 (d, 1H); 7.82 (d, 1H); 9.68 (br s, 1H).

Ms (+ve FAB): 654 (MH)$^+$; 676 (M+Na)$^+$.

EXAMPLE 12

(1R,5S,6S,8R,2'S,4'S)-2-(2-(2-Carboxy-5-chlorophenylcarbamoyl)pyrrolidin-4-ylthio)-6-(1-hydroxyethyl)-1-methylcarbapenem-3-carboxylic acid, disodium salt was prepared from the corresponding allyl protected compound using the method described in example 6.

NMR δ 1.06 (d, 6H); 1.87 (m, part obscured, 1H); 2.72 (dt, 1H); 2.88 (dd, 1H); 3.12 (dd, 1H); 3.30 (quintet, 1H); 3.55 (dd, 1H); 3.72 (quintet, 1H); 3.90 (quintet, 1H); 4.08 (dd, 1H); 4.19 (t, 1H); 7.02 (dd, 1H); 7.92 (d, 1H); 8.49 (d, 1H).

Ms (+ve FAB): 532/534 (MH)$^+$, (Na salt)$^+$; 554/556 (Na$_2$ salt)$^+$.

The starting material was prepared as follows:

4-Chloro-2-nitrobenzoic acid was allylated using the method described in example 1, except using 4-chloro-2-nitrobenzoic acid in place of 3-hydroxy-4-nitrobenzoic acid to give allyl 4-chloro-2-nitrobenzoate.

NMR (CDCl$_3$): δ 4.82 (dt, 2H); 5.30–5.43 (m, 2H); 5.89–6.06 (m, 1H); 7.64 (dd, 1H); 7.76 (d, 1H); 7.86 (d, 1H).

The above nitro compound was reduced by the method described in example 6, for the reduction of allyl 2-methyl-6-nitrobenzoate, to give allyl 2-amino-4-chlorobenzoate.

NMR (CDCl$_3$): δ 4.77 (dt, 2H); 5.24–5.44 (m, 2H); 5.60 (br, 2H); 5.92–6.12 (m, 1H); 6.60 (dd, 1H); 6.66 (d, 1H); 7.81 (d, 1H).

The above amine was condensed with (2S,4S)-4-acetylthio-1-allyloxycarbonyl-2-carboxypyrrolidine using the method described in example 1, except using the above amine in place of allyl 3-allyloxy-4-aminobenzoate to give (2S,4S)-1-allyloxycarbonyl-2-(2-allyloxycarbonyl-5-chlorophenylcarbamoyl)pyrrolidin-4-ylthioacetate.

NMR (CDCl$_3$): δ 2.23 (m, 1H); 2.29 (s, 3H); 2.79 (br, 1H); 3.52 (dd, 1H); 4.04 (quintet, 1H); 4.18 (br m, 1H); 4.46–4.69 (br m, 3H); 4.80 (d, 2H); 5.20 (br, 2H); 5.34–5.45 (m, 2H); 5.83 (br, 1H); 5.91–6.11 (m, 1H); 7.08 (dd, 1H); 8.00 (d, 1H); 8.83 (br s, 1H); 11.67 (s, 1H).

Ms (+ve FAB): 467/469 (MH)$^+$; 489/491 (M+Na)$^+$

The above thioacetate was deacetylated to the corresponding thiol, which was condensed without further purification with allyl (1R,5R,6S,8R)-6-(1-hydroxyethyl)-1-methyl-2-diphenylphosphoryloxycarbapenem-3-carboxylate, using the method described in example 1 for the preparation of protected carbapenems, to give allyl (1R,5S,6S,8 R,2'S,4'S)-2-(1-allyloxycarbonyl-2-(2-allyloxycarbonyl-5-chlorophenylcarbamoyl)pyrrolidin-4-ylthio)-6-(1-hydroxyethyl)-1-methylcarbapenem-3-carboxylate.

NMR (CDCl$_3$): δ 1.23 (d, 3H); 1.35 (d, 3H); 2.28 (quintet, 1H); 2.79 (br, 1H); 3.24 (dd, 1H); 3.29 (quintet, 1H); 3.59 (dd, 1H); 3.78 (br, 1H); 4.05–4.19 (br+overlapping m, 3H); 4.50–4.85 (m, 7H); 5.05–5.41 (m, 6H); 5.70–6.08 (m, 3H); 7.08 (dd, 1H); 7.99 (d, 1H); 8.82 (d, 1H); 11.73 (br s, 1H).

Ms (+ve FAB): 674/676 (MH)$^+$; 696/698 (M+Na)$^+$.

EXAMPLE 13

(1R,5S,6S,8R,2'S,4'S)-2-(2-(2,4-Dicarboxyphenylcarbamoyl)pyrrolidin-4-ylthio)-6-(1-hydroxyethyl)-1-methylcarbapenem-3-carboxylic acid was prepared from the corresponding allyl protected compound using the method described in example 1.

NMR δ 1.31 (d, 6H); 1.97 (m, part obscured, 1H); 2.91 (overlapping m, 2H); 3.36 (dd, 1H); 3.58 (quintet, 1H); 3.74 (dd, 1H); 3.86 (quintet, 1H); 4.11 (quintet, 1H); 4.32 (dd overlapping m, 2H); 8.19 (dd, 1H); 8.73 (d, 1H); 8.81 (d, 1H).

Ms (+ve FAB): 520 (MH)$^+$.

The starting material was prepared as follows:

3-Carboxy-4-nitrobenzoic acid was allylated using the method described in example 1, except using 3-carboxy-4-nitrobenzoic acid in place of 3-hydroxy-4-nitrobenzoic acid and that the reaction was carried out at 95° for 1 hour, to give allyl 3-allyloxycarbonyl-4-nitrobenzoate.

NMR (CDCl$_3$): δ 4.86 (m, 4H); 5.30–5.48 (m, 4H); 5.79–6.14 (m, 2H); 7.93 (d, 2H); 8.31 (dd, 1H); 8.46 (d, 1H).

The above nitro compound was reduced by the method described in example 6, for the reduction of allyl 2-methyl-6-nitrobenzoate, except that the solvent was ethanol, to give allyl 3-allyloxycarbonyl-4-aminobenzoate.

NMR (CDCl$_3$): δ 4.79 (m, 4H); 5.22–5.46 (m, 4H); 5.90 (br, 1H); 5.94–6.14 (m, 2H); 6.64 (d, 1H); 7.93 (dd, 1H); 8.65 (d, 1H).

The above amine was condensed with (2S,4S)-4-acetylthio-1-allyloxycarbonyl-2-carboxypyrrolidine using the method described in example 1, except using the above amine in place of allyl 3-allyloxy-4-aminobenzoate, to give (2S,4S)-1-allyloxycarbonyl-2-(2,4-diallyloxycarbonylphenylcarbamoyl)pyrrolidin-4-ylthioacetate.

NMR (CDCl₃): δ 2.20, 2.21 (s overlapping m, 4H); 2.74 (br, 1H); 3.47 (dd, 1H); 3.97 (quintet, 1H); 4.12 (dd, 1H); 4.40–4.62 (br m, 3H); 4.76 (d, 4H); 5.14 (br, 2H); 5.22–5.40 (m, 4H); 5.80 (br, 1H); 5.89–6.07 (m, 2H); 8.15 (dd, 1H); 8.71 (d, 1H); 8.76 (d, 1H); 11.77 (s, 1H).

The above thioacetate was deacetylated to the corresponding thiol, which was condensed without further purification with allyl (1R,5R,6S,8R)-6-(1-hydroxyethyl)-1-methyl-2-diphenylphosphoryloxycarbapenem-3-carboxylate, using the method described in example 1 for the preparation of protected carbapenems, to give allyl (1R,5S,6S,8 R,2'S,4'S)-2-(1-allyloxycarbonyl-2-(2,4 -diallyloxycarbonylphenylcarbamoyl)pyrrolidin-4-ylthio)-6-(1-hydroxyethyl)-1-methylcarbapenem- 3-carboxylate.

NMR (CDCl₃): δ 1.23 (d, 3H); 1.35 (d, 3H); 2.29 (quintet, 1H); 2.81 (br, 1H); 3.25 (dd, 1H); 3.30 (t, 1H); 3.59 (dd, 1H); 3.80 (br, 1H); 4.25 (dd overlapping m, 3H); 4.60 (m, 5H); 4.82 (m, 4H); 5.00–5.48 (m, 8H); 5.70–6.12 (m, 4H); 8.21 (dd, 1H); 8.78 (d, 1H); 8.82 (d, 1H); 11.92 (s, 1H).

Ms (+ve FAB): 724 (MH)⁺; 746 (M+Na)⁺.

EXAMPLE 14

(1R,5S,6S,8R,2'S,4'S)-2-(2-(2,6-Dicarboxyphenylcarbamoyl)pyrrolidin-4 -ylthio)-6-(1-hydroxyethyl)-1-methylcarbapenem-3-carboxylic acid was prepared from the corresponding allyl protected compound using the method described in example 1.

NMR δ 1.31 (d, 6H); 1.92 (m, part obscured, 1H); 2.91 (overlapping m, 2H); 3.37 (dd, 1H); 3.59 (quintet, 1H); 3.71–3.91 (overlapping m, 2H); 4.12 (quintet, 1H); 4.29, 4.33 (dd overlapping t, 2H); 7.43 (t, 1H); 8.08 (d, 2H).

Ms (+ve FAB): 520 (MH)⁺.

The starting material was prepared as follows:

3-Carboxy-2-nitrobenzoic acid was allylated using the method described in example 1, except using 3-carboxy-2-nitrobenzoic acid in place of 3-hydroxy-4-nitrobenzoic acid and that the reaction was carried out at 95° for 1.5 hours, to give allyl 3-allyloxycarbonyl-2-nitrobenzoate.

NMR (CDCl₃): δ 4.81 (m, 4H); 5.29–5.44 (m, 4H); 5.87–6.07 (m, 2H); 7.65 (t, 1H); 8.20 (d, 2H).

The above nitro compound was reduced by the method described in example 6, except that the solvent was ethanol, to give allyl 3 -allyloxycarbonyl-2-aminobenzoate.

NMR (CDCl₃): δ 4.78 (dt, 4H); 5.25–5.45 (m, 4H); 5.93–6.13 (m, 2H); 6.56 (t, 1H); 8.05 (br, 2H); 8.13 (d, 2H).

The above amine was condensed with (2S,4S)-4-acetylthio-1 -allyloxycarbonyl-2-carboxypyrrolidine using the method described in example 1, except using the above amine in place of allyl 3-allyloxy-4-aminobenzoate and purifying by medium pressure chromatography using a gradient of diethyl ether (0 to 20%) in dichloromethane, to give (2S,4S)-1-allyloxycarbonyl-2-(2,6 -diallyloxycarbonylphenylcarbamoyl)pyrrolidin-4-ylthioacetate.

NMR (CDCl₃): δ 2.18, 2.23 (s overlapping m, 4H); 2.68 (br, 1H); 3.41 (dd, 1H); 3.92 (quintet, 1H); 4.16 (dd, 1H); 4.39 (br, 1H); 4.53 (br, 2H); 4.72 (dt, 4H); 5.11 (br, 2H); 5.20–5.40 (m, 4H); 5.77 (br, 1H); 5.89–6.04 (m, 2H); 7.19 (t, 1H); 7.99 (d, 2H); 11.05 (s, 1H).

The above thioacetate was deacetylated to the corresponding thiol, which was condensed without further purification with allyl (1R,5R,6 S,8R)-6-(1-hydroxyethyl)-1-methyl-2-diphenylphosphoryloxycarbapenem-3-carboxylate, using the method described in example 1 for the preparation of protected carbapenems, to give allyl (1R,5S,6S,8R,2'S,4'S)-2-(1-allyloxycarbonyl-2-(2,6 -diallyloxycarbonylphenylcarbamoyl)pyrrolidin-4-ylthio)-6-(1-hydroxyethyl)-1-methylcarbapenem-3-carboxylate.

NMR (CDCl₃): δ 1.23 (d, 3H); 1.35 (d, 3H); 2.27 (dt, 1H); 2.74 (quintet, 1H); 3.24 (dd, 1H); 3.30 (t, 1H); 3.55 (dd, 1H); 3.70 (br quintet, 1H); 4.12–4.30 (overlapping m, 3H); 4.47 (t, 1H); 4.55–4.75 (m, 4H); 4.78 (d, 4H); 5.05–5.44 (m, 8H); 5.70–6.12 (m, 4H); 7.27 (t, 1H); 8.07 (d, 2H); 11.19 (s, 1H).

Ms (+ve FAB): 724 (MH)⁺; 746 (M+Na)⁺.

EXAMPLE 15

(1R,5S,6S,8R,2'S,4'S)-2-(2-(2-Carboxy-6 -methoxyphenylcarbamoyl)pyrrolidin-4-ylthio)-6-(1-hydroxyethyl)-1-methylcarbapenem-3-carboxylic acid, disodium salt was prepared from the corresponding allyl protected compound using the method described in example 6.

NMR δ 1.18 (d, 6H); 1.82 (m, part obscured, 1H); 2.74 (dt, 1H); 2.86 (dd, 1H); 3.22 (dd, 1H); 3.41 (quintet, 1H); 3.56–3.75 (overlapping m, 2H); 3.84 (s, 3H); 3.99 (quintet, 1H); 4.17, 4.19 (t overlapping dd, 2H); 7.23 (dd, 1H); 7.29 (t, 1H); 7.35 (dd, 1H).

Ms (+ve FAB): 528 (MH)⁺, (Na salt)⁺; 550 (Na₂ salt)⁺.

The starting material was prepared as follows:

3-Methoxy-2-nitrobenzoic acid was allylated using the method described in example 1, except using 3-methoxy-2-nitrobenzoic acid in place of 3-hydroxy-4-nitrobenzoic acid to give allyl 3-methoxy-2-nitrobenzoate.

NMR (CDCl₃): δ 3.93 (s, 3H); 4.79 (dt, 2H); 5.27–5.43 (m, 2H); 5.87–6.07 (m, 1H); 7.25 (dd, 1H); 7.49 (t, 1H); 7.62 (dd, 1H).

Ms (CI): 255 (M+NH₄)⁺.

The above nitro compound was reduced by the method described in example 6 for the reduction of allyl 2-methyl-6-nitrobenzoate, except that the solvent was ethanol, to give allyl 2-amino-3-methoxybenzoate.

NMR (CDCl₃): δ 3.86 (s, 3H); 4.78 (dt, 2H); 5.24–5.43 (m, 2H); 5.60 (br, 2H); 5.96–6.11 (m, 1H); 6.57 (t, 1H); 6.85 (dd, 1H); 7.52 (dd, 1H).

Ms (CI): 208 (MH)⁺.

The above amine was condensed with (2S,4S)-4-acetylthio-1 -allyloxycarbonyl-2-carboxypyrrolidine using the method described in example 1, except using the above amine in place of allyl 3-allyloxy-4-aminobenzoate, to give (2S,4S)-1-allyloxycarbonyl-2-(2-allyloxycarbonyl- 6-methoxyphenylcarbamoyl)pyrrolidin-4-ylthioacetate.

NMR (CDCl₃): δ 2.32, 2.37 (s overlapping m, 4H); 2.71 (br, 1H); 3.40 (dd, 1H); 3.87 (s, 3H); 3.98 (quintet, 1H); 4.22 (dd, 1H); 4.52 (br t, 1H); 4.64 (d, 2H); 4.77 (dm, 2H); 5.22 (br, 2H); 5.24–5.43 (m, 2H); 5.87 (br, 1H); 5.94–6.13 (m, 1H); 7.08 (dd, 1H); 7.20 (t, 1H); 7.46 (dd, 1H); 8.90 (br, 1H).

Ms (+ve FAB): 463 (MH)⁺; 485 (M+Na)⁺.

The above thioacetate was deacetylated to the corresponding thiol, which was condensed without further purification with allyl (1R,5R,6S,8R)-6-(1-hydroxyethyl)-1-methyl-2-diphenylphosphoryloxycarbapenem-3-carboxylate, using the method described in example 1 for the preparation of protected carbapenems, to give allyl (1R,5S,6S,8 R,2'S,4'S)-2-(1-allyloxycarbonyl-2-(2-allyloxycarbonyl-6 -methoxyphenylcarbamoyl)pyrrolidin-4-ylthio)-6-(1-hydroxyethyl)-1-methylcarbapenem- 3-carboxylate.

NMR (CDCl₃): δ 1.26 (d, 3H); 1.36 (d, 3H); 2.32 (br, 1H); 2.77 (br, 1H); 3.23 (dd, 1H); 3.34 (t, 1H); 3.45 (t, 1H); 3.65

(dd, 1H); 3.87 (s, 3H); 4.23 (dd overlapping m, 3H); 4.51 (br t, 1H); 4.60–4.80 (m, 6H); 5.17–5.46 (m, 6H); 5.80–6.09 (m, 3H); 7.09 (d, 1H); 7.21 (t, 1H); 7.47 (d, 1H); 8.85 (br, 1H).

Ms (+ve FAB): 670 (MH)$^+$; 692 (M+Na)$^+$.

EXAMPLE 16

(1R,5S,6S,8R,2'S,4'S)-2-(2-(2-Carboxy-5-trifluoromethylphenylcarbamoyl)pyrrolidin-4-ylthio)-6-(1-hydroxyethyl)-1-methylcarbapenem-3-carboxylic acid, disodium salt was prepared from the corresponding allyl protected compound using the method described in example 6.

NMR δ 1.17 (d, 6H); 1.82 (m, part obscured, 1H); 2.68–2.87 (overlapping m, 2H); 3.21 (dd, 1H); 3.32–3.65 (overlapping m, 3H); 3.88 (quintet, 1H); 4.12–4.23 (overlapping m, 2H); 7.37 (dd, 1H); 8.19 (d, 1H); 8.93 (d, 1H).

Ms (+ve FAB): 566 (MH)$^+$, (Na salt)$^+$; 588 (Na$_2$ salt)$^+$.

The starting material was prepared as follows:

2-Nitro-4-trifluoromethylbenzoic acid was allylated using the method described in example 1, except using 2-nitro-4-trifluoromethylbenzoic acid in place of 3-hydroxy-4-nitrobenzoic acid to give allyl 2-nitro- 4-trifluoromethylbenzoate.

NMR (CDCl$_3$): δ 4.86 (dt, 2H); 5.31–5.46 (m, 2H); 5.89–6.09 (m, 1H); 7.89 (d, 1H); 7.96 (dd, 1H); 8.21 (d, 1H).

Ms (EI): 275M$^+$.

The above nitro compound was reduced by the method described in example 6 for the reduction of allyl 2-methyl-6-nitrobenzoate, except that the solvent was ethanol, to give allyl 2-amino-4-trifluoromethylbenzoate.

NMR (CDCl$_3$): δ 4.80 (dt, 2H); 5.27–5.45 (m, 2H); 5.60 (br, 2H); 5.95–6.11 (m, 1H); 6.84 (dd, 1H); 6.90 (br s, 1H); 8.00 (d, 1H).

Ms (CI): 245 (MH)$^+$.

The above amine was condensed with (2S,4S)-4-acetylthio-1-allyloxycarbonyl-2-carboxypyrrolidine using the method described in example 1, except using the above amine in place of allyl 3-allyloxy-4-aminobenzoate to give (2S,4S)-1-allyloxycarbonyl-2-(2-allyloxycarbonyl- 5-trifluoromethylphenylcarbamoyl)pyrrolidine-4-ylthioacetate.

NMR (CDCl$_3$): δ 2.27, 2.29 (s overlapping m, 4H); 2.80 (br, 1H); 3.53 (dd, 1H); 4.05 (quintet, 1H); 4.21 (dd, 1H); 4.53 (br t, 1H); 4.62 (br, 2H); 4.85 (d, 2H); 5.21 (br, 2H); 5.31–5.47 (m, 2H); 5.89 (br, 1H); 5.95–6.11 (m, 1H); 7.36 (d, 1H); 8.19 (d, 1H); 9.10 (d, 1H); 11.67 (s, 1H).

Ms (+ve FAB): 501 (MH)$^+$; 523 (M+Na)$^+$.

The above thioacetate was deacetylated to the corresponding thiol, which was condensed without further purification with allyl (1R,5R,6 S,8R)-6-(1-hydroxyethyl)-1-methyl-2-diphenylphosphoryloxycarbapenem-3-carboxylate, using the method described in example 1 for the preparation of protected carbapenems, to give allyl (1R,5S,6S,8 R,2'S,4'S)-2-(1-allyloxycarbonyl-2-(2-allyloxycarbonyl-5 -trifluoromethylphenylcarbamoyl)pyrrolidin-4-ylthio)-6-(1-hydroxyethyl)-1 -methylcarbapenem-3-carboxylate.

NMR (CDCl$_3$): δ 1.23 (d, 3H); 1.36 (d, 3H); 2.30 (quintet, 1H); 2.79 (br, 1H); 3.24 (dd, 1H); 3.29 (t, 1H); 3.60 (dd, 1H); 3.79 (m, 1H); 4.18–4.31 (overlapping m, 3H); 4.60 (m, 6H); 4.82 (t, 1H); 5.08–5.48 (m, 6H); 5.76–6.10 (m, 3H); 7.36 (d, 1H); 8.18 (d 1H); 9.10 (d, 1H); 11.78 (s, 1H).

Ms (+ve FAB): 708 (MH)$^+$; 730 (M+Na)$^+$.

EXAMPLE 17

(1R,5S,6S,8R,2'S,4'S)-2-(2-(6-Carboxy-2-hydroxy-3-methylphenylcarbamoyl)pyrrolidin-4-ylthio)-6-(1-hydroxyethyl)-1-methylcarbapenem- 3-carboxylic acid, disodium salt was prepared from the corresponding allyl protected compound using the method described in example 6.

NMR δ 1.18 (d, 6H); 1.77 (m, 1H); 2.23 (s, 3H); 2.67–2.85 (overlapping m, 2H); 3.22 (dd, 1H); 3.34–3.68 (overlapping m, 3H); 3.98 (quintet, 1H); 4.15–4.22 (overlapping m, 2H); 7.07 (d, 1H); 7.41 (d, 1H).

Ms (+ve FAB): 528 (MH)$^+$, (Na salt)$^+$; 550 (Na$_2$ salt)$^+$.

The starting material was prepared as follows:

3-Hydroxy-4-methyl-2-nitrobenzoic acid was allylated using the method described in example 1, except using 3-hydroxy-4-methyl-2-nitrobenzoic acid in place of 3-hydroxy-4-nitrobenzoic acid to give allyl 3-allyloxy-4-methyl-2-nitrobenzoate.

NMR (CDCl$_3$): δ 2.40 (s, 3H); 4.46 (dt, 2H); 4.78 (dt, 2H); 5.25–5.44 (m, 4H); 5.87–6.12 (m, 2H); 7.36 (d, 1H); 7.72 (d, 1H).

Ms (EI): 277M$^+$.

The above nitro compound was reduced by the method described in example 6 for the reduction of allyl 2-methyl-6-nitrobenzoate, except that the solvent was ethanol, to give allyl 3-allyloxy-2-amino-4-methylbenzoate.

NMR (CDCl$_3$): δ 2.27 (s, 3H); 4.33 (dt, 2H); 4.77 (dt, 2H); 5.24–5.48 (m, 4H); 5.88–6.19 (m+br, 4H); 6.44 (d, 1H); 7.58 (d, 1H).

Ms (CI): 247 (MH)$^+$.

The above amine was condensed with (2S,4S)-4-acetylthio-1-allyloxycarbonyl-2-carboxypyrrolidine using the method described in example 1, except using the above amine in place of allyl 3-allyloxy-4-aminobenzoate to give (2S,4S)-1-allyloxycarbonyl-2-(2-allyloxy-6-allyloxycarbonyl-3-methylphenylcarbamoyl)pyrrolidin-4-ylthioacetate.

NMR (CDCl$_3$): δ 2.31, 2.35, 2.49 (2 s overlappping m, 7H); 2.67 (br, 1H); 3.39 (dd, 1H); 3.97 (quintet, 1H); 4.21 (br t, 1H); 4.35 (d, 2H); 4.55 (t, 1H); 4.63 (d, 2H) 4.76 (dt, 2H); 5.18–5.42 (m, 6H); 5.88 (br, 1H); 5.93–6.12 (m, 2H); 7.07 (d, 1H); 7.56 (d, 1H); 9.11 (s, 1H).

Ms (+ve FAB): 503 (MH)$^+$; 525 (M+Na)$^+$.

The above thioacetate was deacetylated to the corresponding thiol, which was condensed without further purification with allyl (1R,5R,6 S,8R)-6-(1-hydroxyethyl)-1-methyl-2-diphenylphosphoryloxycarbapenem-3-carboxylate, using the method described in example 1 for the preparation of protected carbapenems to give allyl (1R,5S,6S,8 R,2'S,4'S)-2-(1-allyloxycarbonyl-2-(2-allyloxy-6-allyloxycarbonyl-3 -methylphenylcarbamoyl)pyrrolidin-4-ylthio)-6-(1-hydroxyethyl)- 1-methylcarbapenem-3-carboxylate.

NMR (CDCl$_3$): δ 1.25 (d, 3H); 1.36 (d, 3H); 2.34 (s overlapping br m, 4H); 2.72 (br, 1H); 3.24 (dd, 1H); 3.32 (quintet, 1H); 3.46 (dd, 1H); 3.67 (quintet, 1H); 4.11–4.29 (overlapping m, 3H); 4.32 (d, 2H); 4.53 (t, 1H); 4.60–4.78 (m, 6H); 5.17–5.45 (m, 8H); 5.85–6.10 (m, 4H); 7.07 (d, 1H); 7.58 (d, 1H); 9.13 (br s, 1H).

Ms (+ve FAB): 710 (MH)$^+$; 732 (M+Na)$^+$.

EXAMPLE 18

(1R,5S,6S,8R,2'S,4'S)-2-(2-(5-Carboxy-3-chloro-2-hydroxyphenylcarbamoyl)pyrrolidin-4-ylthio)-6-(1-hydroxyethyl)-1-methylcarbapenem- 3-carboxylic acid, disodium salt was prepared from the corresponding allyl protected compound using the method described in example 6, except the DMSO/THF solution was gently warmed to dissolve the catalyst.

NMR δ 1.12 (d, 3H); 1.15 (d, 3H); 1.74 (m, 1H); 2.65 (m, 2H); 3.18 (dd, 1H); 3.32–3.66 (overlapping m, 3H); 3.95 (quintet, 1H); 4.02 (t, 1H); 4.13 (dd, 1H); 7.58 (d, 1H); 8.60 (d, 1H).

Ms (+ve FAB): 570/572 (MH)$^+$.

The starting materials were prepared as follows:

3-Chloro-4-hydroxy-5-nitrobenzoic acid

Sulphuric acid (83%, 20 ml) was cooled in an ice-bath, and 3-chloro-4-hydroxybenzoic acid (4 g, 22 mM) stirred in. After 10 minutes, nitric acid (70%, 1.43 ml, 22 mM) was run in, and the mixture stirred at 0° for 2 hours. After pouring onto ice, the solid was filtered, and recrystallised from aqueous ethanol to give title compound as yellow crystals (2.1 g, 44%).

NMR (DMSO-d$_6$): δ 8.17 (d, 1H); 8.35 (d, 1H).

Ms (–ve FAB): 217/219 (MH)$^-$.

Allyl 4-allyloxy-3-chloro-5-nitrobenzoate

3-Chloro-4-hydroxy-5-nitrobenzoic acid (2.5 g, 11.5 mM) was dissolved in DMF (30 ml) and anhydrous K$_2$CO$_3$ (6.36 g, 41.3 mM) added with stirring. Allyl bromide (2.92 ml, 33.7 mM) was run in, and the mixture stirred for 18 hours at ambient temperature. The solvent was removed by evaporation, the residue treated with water, the pH was adjusted to 5.5, and product was extracted into ethyl acetate. The combined extracts were washed with aqueous NaH$_2$PO$_4$, water, brine, and dried over MgSO$_4$. The residue after evaporation was subjected to chromatography on silica, eluting with a mixture of petrol/EtOAc (10:1), to give a mixture of allyl 3-chloro-4-hydroxy-5-nitrobenzoate, with only a little of the desired allyl 4-allyloxy-3-chloro-5-nitrobenzoate. This mixture (1.95 g, ≅7.6 mM) was dissolved in acetone (15 ml), and anyhydrous K$_2$CO$_3$ (1.57 g, 11.4 mM) and allyl bromide (1 ml, 11.6 mM) added. The mixture was refluxed for 2 days, cooled, poured into water, and extracted three times with dichloromethane. The combined extracts were washed with a saturated aqueous solution of sodium bicarbonate, water and brine, before drying over MgSO$_4$. Evaporation gave the title compound as an oil (1.88 g, 80%).

NMR (CDCl$_3$): δ 4.74 (dt, 2H); 4.85 (dt, 2H); 5.31–5.48 (m, 4H); 5.93–6.20 (m, 2H); 8.30 (d, 1H); 8.36 (d, 1H).

Ms (CI) 297/299 M$^+$.

Allyl 4-allyloxy-5-amino-3-chlorobenzoate

Stannous chloride dihydrate (7.13 g, 31.6 mM) was heated at reflux in ethanol (10 ml), under an argon blanket, to give a solution. The heat was removed, and the above nitro compound (1.88 g, 6.3 mM) in ethanol was run in. Reflux was then continued for 3 hours, the mixture cooled, and solvents removed. The residue was dissolved in ethyl acetate, and treated with 880 ammonia until basic. The organic phase was decanted from precipitated tin salts, and the slurry re-extracted similarly with more solvent. Combined organic phases were then washed with diluted ammonia, water and brine before drying over MgSO$_4$. Evaporation gave allyl 4-allyloxy-5-amino-3-chlorobenzoate as an oil (1.34 g, 80%).

NMR (CDCl$_3$): δ 4.02 (br, 2H); 4.55 (dt, 2H); 4.79 (dt, 2H); 5.25–5.47 (m, 4H); 5.92–6.23 (m, 2H); 7.33 (d, 1H); 7.46 (d, 1H).

Ms (CI): 268/270 (MH)$^+$.

Preparation of Side Chain Pyrrolidin-4-ylthioacetate

The above amine was condensed with (2S,4S)-4-acetylthio-1-allyloxycarbonyl-2-carboxypyrrolidine using the method described in example 1, except using the above amine in place of allyl 3-allyloxy-4-aminobenzoate to give (2S,4S)-1-allyloxycarbonyl-2-(2-allyloxy-5-allyloxycarbonyl-3-chlorophenylcarbamoyl)pyrrolidin-4-ylthioacetate.

NMR (CDCl$_3$); δ 2.31 (s, 3H); 2.55 (br, 1H); 2.63 (br, 1H); 3.39 (dd, 1H); 4.02 (quintet, 1H); 4.15 (dd, 1H); 4.55 (m, part obscured, 1H); 4.59–4,65 (m, 4H); 4.81 (dt, 2H); 5.21–5.47 (m, 6H); 5.83–6.18 (m, 3H); 7.83 (d, 1H); 8.97 (d, 1H); 9.10 (br, 1H).

Ms (+ve FAB): 523/525 (MH)$^+$; 545/547 (M+Na)$^+$.

The above thioacetate was deacetylated to the corresponding thiol, which was condensed without further purification with allyl (1R,5R,6S,SR)-6-(1-hydroxyethyl)-1-methyl-2-diphenylphosphoryloxycarbapenem-3-carboxylate, using the method described in example 1, for the preparation of protected carbapenems, to give allyl (1R,5S,6S,8R,2'S,4'S)-2-(1-allyloxycarbonyl-2-(2-allyloxy-5-allyloxycarbonyl-3-chlorophenylcarbamoyl)pyrrolidin-4-ylthio)-6-(1-hydroxyethyl)-1-methylcarbapenem-3-carboxylate.

NMR (CDCl$_3$): δ 1.27 (d, 3H); 1.36 (d, 3H); 2.62 (br, 2H); 3.23 (dd overlapping m, 2H); 3.43 (dd, 1H); 3.87 (t, 1H); 4.07 (m, 1H); 4.20–4.29 (dd overlapping quintet, 2H); 4.51–4.72 (m, 7H); 4.80 (dt, 2H); 5.18–5.45 (m, 8H); 5.82–6.10 (m, 4H); 7.83 (d, 1H); 8.99 (d, 1H); 9.10 (br, 1H).

Ms (+ve FAB): 730/732 (MH)$^+$; 752/754 (M+Na)$^+$.

EXAMPLE 19

(1R,5S,6S,8R,2'S,4'S)-2-(2-(2-Carboxy-5-methoxyphenylcarbamoyl)pyrrolidin-4-ylthio)-6-(1-hydroxyethyl)-1-methylcarbapenem-3-carboxylic acid, disodium salt was prepared from the corresponding allyl protected compound using the method described in example 6.

NMR δ 1.16 (d, 6H); 1.79 (m, 1H); 2.70 (m, 1H); 3.21 (dd, 1H); 3.43 (quintet, 1H); 3.50–3.68 (overlapping m, 3H); 3.81 (s, 3H); 3.95–4.08 (m, 2H); 4.19 (dd, 1H); 6.69 (dd, 1H); 7.96 (d, 1H); 8.29 (d, 1H).

Ms (+ve FAB): 528 (MH)$^+$, (Na salt)$^+$; 550 (MH)$^+$, (Na$_2$ salt)$^+$.

The starting materials were prepared as follows:

4-Methoxy-2-nitrobenzoic acid was allylated using the method described in example 1 except using 4-methoxy-2-nitrobenzoic acid in place of 3-hydroxy-4-nitrobenzoic acid, to give allyl 4-methoxy-2-nitrobenzoate.

NMR (DMSO-d$_6$): δ 3.91 (s, 3H); 4.75 (dt, 2H); 5.24–5.42 (m, 2H); 5.87–6.07 (m, 1H); 7.32 (dd, 1H); 7.56 (d, 1H) 7.90 (d, 1H).

Ms (CI): 238 (MH)$^+$; 255 (M+NH$_4$)$^+$.

The above nitro compound was reduced by the method described in example 6 for the reduction of allyl 2-methyl-6-nitrobenzoate to give allyl 2-amino-4-methoxybenzoate.

NMR (DMSO-d$_6$): δ 3.72 (s, 3H); 4.70 (dt, 2H); 5.21–5.39 (m, 2H); 5.91–6.10 (m, 1H); 6.14 (dd, 1H); 6.28 (d, 1H); 7.66 (d, 1H).

Ms (CI): 208 (MH)$^+$.

The above amine was condensed with (2S,4S)-4-acetylthio-1-allyloxycarbonyl-2-carboxypyrrolidine using the method described in example 1 except using the above amine in place of allyl 3-allyloxy-4-aminobenzoate, and purifying by chromatography using a gradient of dichloromethane/diethyl ether (100:0 to 80:20) to give (2S,4S)-1-allyloxycarbonyl-2-(2-allyloxycarbonyl-5-methoxyphenylcarbamoyl)pyrrolidin-4-ylthioacetate.

NMR δ 2.11 (m, 1H); 2.27 (s, 3H); 2.83 (quintet, 1H); 3.45 (br, 1H); 3.85 (s, 3H); 4.03 (t, 1H); 4.13 (dd, 1H);

4.42–4.63 (br m, 3H); 4.79 (d, 2H); 4.95–5.44 (br+m, 4H); 5.70–6.13 (br+m, 2H); 6.75 (dd, 1H); 8.02 (d, 1H); 8.27 (br s, 1H).

Ms (+ve FAB): 463 (MH)⁺; 485 (M+Na)⁺.

The above thioacetate was deacetylated to the corresponding thiol, which was condensed without further purification with allyl (1R,5R,6S,8R)-6-(1-hydroxyethyl)-1-methyl-2-diphenylphosphoryloxycarbapenem-3-carboxylate, using the method described in example 1 for the preparation of protected carbapenems to give allyl (1R,5S,6S,8R,2'S,4'S)-2-(1-allyloxycarbonyl-2-(2-allyloxycarbonyl-5-methoxyphenylcarbamoyl)pyrrolidin-4-ylthio)-6-(1-hydroxyethyl)-1-methylcarbapenem-3-carboxylate.

NMR δ 1.17 (d, 6H); 2.08 (br m, 1H); 2.36 (br m, 1H); 3.26 (dd, 1H); 3.39–3.57 (m, 2H); 3.85 (s, 3H); 3.96–4.06 (m, 2H); 4.13 (dd, 1H); 4.27 (dd, 1H); 4.38–4.81 (overlapping m, 7H); 4.95–5.42 (overlapping m, 6H); 5.68–6.09 (m, 3H); 6.76 (dd, 1H); 7.99 (d, 1H); 8.27 (br s, 1H).

Ms (+ve FAB): 670 (MH)⁺; 692 (M+Na)⁺.

EXAMPLE 20

(1R,5S,6S,8R,2'S,4'S)-2-(2-(2-Carboxy-4-hydroxyphenylcarbamoyl)pyrrolidin-4-ylthio)-6-(1-hydroxyethyl)-1-methylcarbapenem-3-carboxylic acid, disodium salt was prepared from the corresponding allyl protected compound using the method described in example 6.

NMR δ 1.17 (d, 6H); 1.81 (m, 1H); 2.56–2.83 (overlapping m, 2H); 3.21 (dd, 1H); 3.41 (quintet, 1H); 3.56 (dd, 1H); 3.70 (t, 1H); 3.98 (quintet, 1H); 4.10 (t, 1H); 4.17 (dd, 1H); 6.92 (dd, 1H); 7.43 (d, 1H); 8.37 (d, 1H).

The starting materials were prepared as follows:

5-Hydroxy-2-nitrobenzoic acid was allylated using the method described in example 1 except using 5-hydroxy-2-nitrobenzoic acid in place of 3-hydroxy-4-nitrobenzoic acid, to give allyl 5-allyloxy-2-nitrobenzoate.

NMR (DMSO-d₆): δ 4.78 (t, 4H); 5.27–5.48 (m, 4H); 5.91–6.13 (m, 2H); 7.29 (m, 2H); 8.13 (d, 1H).

Ms (CI): 264 (MH)⁺; 281 (M+NH₄)⁺.

The above nitro compound was reduced by the method described in example 6 for the reduction of allyl 2-methyl-6-nitrobenzoate to give allyl 5-allyloxy-2-aminobenzoate.

NMR (DMSO-d₆): δ 4.45 (dt, 2H); (4.76 (dt, 2H); 5.18–5.43 (m, 4H); 5.92–6.12 (m, 2H); 6.31 (br s, 2H); 6.77 (d, 1H); 7.03 (dd, 1H); 7.24 (d, 1H).

Ms (CI): 233 (MH)⁺.

The above amine was condensed with (2S,4S)-4-acetylthio-1-allyloxycarbonyl-2-carboxypyrrolidine using the method described in example 1 except using the above amine in place of allyl 3-allyloxy-4-aminobenzoate, and purifying by chromatography using a gradient of dichloromethane/diethyl ether (100:0 to 90:10) to give (2S,4S)-1-allyloxycarbonyl-2-(4-allyloxy-2-allyloxycarbonylphenylcarbamoyl)pyrrolidin-4-ylthioacetate.

NMR (DMSO-d₆): δ 2.02 (m, 1H); 2.29 (s, 3H); 2.79 (quintet, 1H); 3.97–4.12 (overlapping m, 2H); 4.35–4.65 (overlapping m, 5H); 4.81 (dt, 2H); 4.95–5.47 (m, 6H); 5.65–5.90 (br, 1H); 5.94–6.15 (m, 2H); 7.28 (dd, 1H); 7.48 (d, 1H); 8.26 (br, 1H); 10.85 (br d, 1H).

Ms (+we FAB): 489 (MH)⁺; 511 (M+Na)⁺.

The above thioacetate was deacetylated to the corresponding thiol, which was condensed without further purification with allyl (1R,5R,6S,8R)-6-(1-hydroxyethyl)-1-methyl-2-diphenylphosphoryloxycarbapenem-3-carboxylate, using the method described in example 1 for the preparation of protected carbapenems to give allyl (1R,5S,6S,8R,2'S,4'S)-2-(1-allyloxycarbonyl-2-(4-allyloxy-2-allyloxycarbonylphenylcarbamoyl)pyrrolidin-4-ylthio)-6-(1-hydroxyethyl)-1-methylcarbapenem-3-carboxylate.

NMR δ 1.17 (2×d, 6H); 2.07 (m, 1H); 2.84 (m, 1H); 3.24 (dd, 1H); 3.48 (overlapping m, 2H); 4.01 (overlapping m, 2H); 4.13 (dd, 1H); 4.27 (dd, 1H); 4.42–4.82 (m, 9H); 4.98–5.46 (m, 8H); 5.70–5.85 (m, 1H); 5.95–6.12 (m, 3H); 7.26 (dd, 1H); 7.50 (d, 1H); 8.46 (br, 1H).

Ms (+ve FAB): 696 (MH)⁺; 718 (M+Na)⁺.

EXAMPLE 21

(1R,5S,6S,8R,2'S,4'S)-2-(2-(2-Carboxy-4,5-dimethoxyphenylcarbamoyl)pyrrolidin-4-ylthio)-6-(1-hydroxyethyl)-1-methylcarbapenem-3-carboxylic acid, disodium salt was prepared from the corresponding allyl protected compound using the method described in example 6.

NMR δ 1.15 (d, 3H); 1.18 (d, 3H); 1.78 (m, 1H); 2.69 (m, 1H); 3.19 (dd, 1H); 3.40 (quintet, 1H); 3.45–3.63 (overlapping m, 3H); 3.76 (s, 3H); 3.81 (s, 3H); 3.97 (quintet overlapping m, 2H); 4.05 (dd, 1H); 7.50 (s, 1H); 8.38 (s, 1H).

Ms (−ve FAB): 534 (M−H)⁻.

The starting materials were prepared as follows:

4,5-Dimethoxy-2-nitrobenzoic acid was allylated using the method described in example 1 except using 4,5-dimethoxy-2-nitrobenzoic acid in place of 3-hydroxy-4-nitrobenzoic acid, to give allyl 4,5-dimethoxy-2-nitrobenzoate.

NMR (DMSO-d₆): δ 3.91 (s, 3H); 3.92 (s, 3H); 4.77 (dt, 2H); 5.25–5.43 (m, 2H); 5.88–6.07 (m, 1H); 7.31 (s, 1H); 7.63 (s, 1H).

Ms (CI): 268 (MH)⁺; 285 (M+NH₄)⁺.

The above nitro compound was reduced by the method described in example 6 for the reduction of allyl 2-methyl-6-nitrobenzoate to give allyl 2-amino-4,5-dimethoxybenzoate.

NMR (DMSO-d₆): δ 3.83 (s, 3H); 3.87 (s, 3H); 4.78 (dt, 2H); 5.24–5.43 (m, 2H); 5.50 (br, 1H); 5.95–6.14 (m, 1H); 6.21 (s, 1H); 7.35 (s, 1H).

Ms (CI): 238 (MH)⁺.

The above amine was condensed with (2S,4S)-4-acetylthio-1-allyloxycarbonyl-2-carboxypyrrolidine using the method described in example 1 except using the above amine in place of allyl 3-allyloxy-4-aminobenzoate, and purifying by chromatography using a gradient of hexane:ethyl acetate 2:1 to 2:3, to give (2S,4S)-1-allyloxycarbonyl-2-(2-allyloxycarbonyl-4,5-dimethoxyphenylcarbamoyl)pyrrolidin-4-ylthioacetate.

NMR δ 2.24 (m, 1H); 2.29 (s, 3H); 2.81 (br, 1H); 3.52 (dd, 1H); 3.89 (s, 3H); 3.97 (s, 3H); 4.06 (quintet, 1H); 4.21 (m, 1H); 4.45–4.70 (br m, 3H); 4.80 (d, 2H); 5.05–5.46 (br+m, 4H); 5.70–6.14 (br+m, 2H); 7.50 (s, 1H); 8.48 (s, 1H); 11.69 (s, 1H).

Ms (+ve FAB): 493 (MH)⁺; 515 (M+Na)⁺.

The above thioacetate was deacetylated to the corresponding thiol, which was condensed without further purification with allyl (1R,5R,6S,8R)-6-(1-hydroxyethyl)-1-methyl-2-diphenylphosphoryloxycarbapenem-3-carboxylate, using the method described in example 1 for the preparation of protected carbapenems to give allyl (1R,5S,6S,8R,2'S,4'S)-2-(1-allyloxycarbonyl-2-(2-allyloxycarbonyl-4,5

-dimethoxyphenylcarbamoyl)pyrrolidin-4-ylthio)-6-(1-hydroxyethyl) 1-methylcarbapenem-3-carboxylate.

NMR (CDCl$_3$): δ 1.25 (d, 3H); 1.36 (d, 3H); 2.26 (m, 1H); 2.81 (br, 1H); 3.25 (dd, 1H); 3.32 (m, 1H); 3.57 (dd, 1H); 3.75 (br, 1H); 3.89 (s, 3H); 3.97 (s, 3H); 4.23 (dd overlapping m, 3H); 4.54 (t, 1H); 4.56–4.69 (m, 4H); 4.78 (m, 2H); 5.17–5.45 (m overlapping br, 6H); 5.70–6.13 (m, 3H); 7.48 (s, 1H); 8.46 (s, 1H); 11.74 (s, 1H).

Ms (+ve FAB): 700 (MH)$^+$; 722 (M+Na)$^+$.

EXAMPLE 22

(1R,5S,6S,8R,2'S,4'S)-2-(2-(2-Carboxy-4-fluorophenylcarbamoyl)pyrrolidin-4-ylthio)-6-(1-hydroxyethyl)-1-methylcarbapenem-3-carboxylic acid, disodium salt was prepared from the corresponding allyl protected compound using the method described in example 6, except that diethyl ether was required to precipitate the product.

NMR δ 1.17 (d, 3H); 1.19 (d, 3H); 1.84 (m, part obscured, 1H); 2.78 (m, 1H); 2.90 (dd, 1H); 3.21 (dd, 1H); 3.42 (quintet, 1H); 3.58 (dd, 1H); 3.75 (quintet, 1H); 4.00 (quintet, 1H); 4.17 (m, 2H); 7.22 (sextet, 1H); 7.71 (dd, 1H); 8.55 (dd, 1H).

Ms (+ve FAB): 516 (MH)$^+$, (Na salt)$^+$; 538 (Na$_2$ salt)$^+$.

The starting materials were prepared as follows:

5-Fluoro-2-nitrobenzoic acid was allylated using the method described in example 1, except using 5-fluoro-2-nitrobenzoic acid in place of 3-hydroxy-4-nitrobenzoic acid and that the crude product was purified by chromatography on silica, using a gradient of hexane/ethyl acetate (100:0 to 20:80), to give allyl 5-fluoro-2-nitrobenzoate.

NMR (DMSO-d$_6$): δ 4.82 (dt, 2H); 5.28–5.45 (m, 2H); 5.92–6.08 (m, 1H); 7.69 (m, 1H); 7.79 (dd, 1H); 8.23 (dd, 1H).

Ms (CI): 243 (M+NH$_4$)$^+$.

The above nitro compound was reduced by the method described in example 6, for the reduction at allyl 2-methyl-6-nitrobenzoate, to give allyl 2-amino-5-fluorobenzoate.

NMR (DMSO-d$_6$): δ 4.75 (dt, 2H); 5.23–5.42 (m, 2H); 5.95–6.11 (m, 1H); 6.81 (dd, 1H); 7.19 (m, 1H); 7.41 (dd, 1H).

Ms (CI): 196 (MH)$^+$.

The above amine was condensed with (2S,4S)-4-acetylthio-1-allyloxycarbonyl-2-carboxypyrrolidine using the method described in example 1, except using the above amine in place of allyl 3-allyloxy-4-aminobenzoate and purifying by chromatography using a gradient of dichloromethane/diethyl ether (100:0 to 90:10) to give (2S,4S)-1-allyloxycarbonyl-2-(2-allyloxycarbonyl-4-fluorophenylcarbamoyl)pyrrolidin-4-ylthioacetate.

NMR (DMSO-d$_6$): δ 2.03 (m, 1H); 2.29 (s, 3H); 2.79 (m, 1H); 3.39 (br, 1H); 3.95–4.12 (overlapping m, 2H); 4.47 (br, 1H); 4.58 (br, 2H); 4.81 (dt, 2H); 5.00–5.25 (br m, 2H); 5.19–5.46 (m, 2H); 5.88 (br, 1H); 5.95–6.14 (m, 1H); 7.54 (m, 1H); 7.71 (dd, 1H); 8.39 (br, 1H); 11.00 (br, 1H).

Ms (+ve FAB): 451 (MH)$^+$; 473 (M+Na)$^+$.

The above thioacetate was deacetylated to the corresponding thiol, which was condensed without further purification with allyl (1R,5R,6S,8R)-6-(1-hydroxyethyl)-1-methyl-2-diphenylphosphoryloxycarbapenem-3-carboxylate, using the method described in example 1, for the preparation of protected carbapenems, to give allyl (1R,5S,6S,8R,2'S,4'S)-2-(1-allyloxycarbonyl-2-(2-allyloxycarbonyl-4-fluorophenylcarbamoyl)pyrrolidin-4-ylthio)-6-(1-hydroxyethyl)-1-methylcarbapenem-3-carboxylate.

NMR δ 1.18 (d, 3H); 1.21 (d, 3H); 2.15 (dt, 1H); 2.88 (m, 1H); 3.28 (dd, 1H); 3.42–3.58 (m, 2H); 3.95–4.16 (overlapping m, 3H); 4.28 (dd, 1H); 4.40–4.85 (overlapping m, 7H); 5.00–5.45 (m, 6H); 5.70–5.86 (m, 1H); 5.95–6.11 (m, 2H); 7.47 (m, 1H); 7.75 (dd, 1H); 8.65 (br, 1H).

Ms (+ve FAB): 658 (MH)$^+$; 680 (M+Na)$^+$.

EXAMPLE 23

(1R,5S,6S,8R,2'S,4'S)-2-(2-(2-Carboxy-5-fluorophenylcarbamoyl)pyrrolidin-4-ylthio)-6-(1-hydroxyethyl)-1-methylcarbapenem-3-carboxylic acid, disodium salt from the corresponding allyl protected compound using the method described in example 6.

NMR δ 1.12 (d, 6H); 1.82 (m, part obscured, 1H); 2.62–2.81 (overlapping m, 2H); 3.18 (dd, 1H); 3.37 (quintet, 1H); 3.50 (dd, 1H); 3.64 (quintet, 1H); 3.95 (quintet, 1H); 4.08 (t, 1H); 4.13 (dd, 1H); 6.85 (sextet, 1H); 8.04 (t, 1H); 8.36 (t, 1H).

Ms (+ve FAB): 516 (MH)$^+$, (Na salt)$^+$; 538 (Na$_2$ salt)$^+$.

The starting materials were prepared as follows:

4-Fluoro-2-nitrobenzoic acid was allylated using the method described in example 1, except using 4-fluoro-2-nitrobenzoic acid in place of 3-hydroxy-4-nitrobenzoic acid to give allyl 4-fluoro-2-nitrobenzoate.

NMR (DMSO-d$_6$): δ 4.78 (m, 2H); 5.26–5.44 (m, 2H); 5.87–6.09 (m, 1H); 7.72 (m, 1H); 7.98–8.12 (m, 2H).

Ms (CI): 225 M$^+$; 243 (M+NH$_4$)$^+$.

The above nitro compound was reduced by the method described in example 6, for the reduction of allyl 2-methyl-6-nitrobenzoate, to give allyl 2-amino-4-fluorobenzoate.

NMR (DMSO-d$_6$): δ 4.74 (dt, 2H); 5.22–5.43 (m, 2H); 5.95–6.14 (m, 1H); 6.37 (sextet, 1H); 6.53 (dd, 1H); 6.85 (br, 1H); 7.80 (dd, 1H).

Ms (CI): 196 (MH)$^+$.

The above amine was condensed with (2S,4S)-4-acetylthio-1-allyloxycarbonyl-2-carboxypyrrolidine using the method described in example 1, except using the above amine in place of 3-allyloxy-4-aminobenzoate and purifying by chromatography using a gradient of dichloromethane/diethyl ether (100:0 to 90:10) to give (2S,4S)-1-allyloxycarbonyl-2-(2-allyloxycarbonyl-5-fluorophenylcarbamoyl)pyrrolidin-4-ylthioacetate.

NMR (DMSO-d$_6$): δ 2.05 (m, 1H); 2.29 (s, 3H); 2.82 (m, 1H); 3.35 (br, part obscured, 1H); 3.96–4.15 (overlapping m, 2H); 4.52 (br, 3H); 4.82 (dt, 2H); 4.95–5.25 (br m, 2H); 5.27–5.46 (m, 2H); 5.85 (br, 1H); 5.95–6.16 (m, 1H); 7.08 (sextet, 1H); 8.12 (dd, 1H); 8.36 (br d, 1H); 11.45 (br d, 1H).

Ms (+ve FAB): 451 (MH)$^+$; 473 (M+Na)$^+$.

The above thioacetate was deacetylated to the corresponding thiol, which was condensed without further purification with allyl (1R,5R,6S,8R)-6-(1-hydroxyethyl)-1-methyl-2-diphenylphosphoryloxycarbapenem-3-carboxylate, using the method described in example 1 for the preparation of protected carbapenems, to give allyl (1R,5S,6S,8R,2'S,4'S)-2-(1-allyloxycarbonyl-2-(2-allyloxycarbonyl-5-fluorophenylcarbamoyl)pyrrolidin-4-ylthio)-6-(1-hydroxyethyl)-1-methylcarbapenem-3-carboxylate.

NMR δ 1.17 (d, 3H); 1.18 (d, 3H); 2.11 (dt, 1H); 2.87 (m, 1H); 3.27 (dd, 1H); 3.41–3.58 (m, 2H); 4.01 (quintet, 2H); 4.13 (dd, 1H); 4.28 (dd, 1H); 4.35–4.85 (overlapping m, 7H); 4.95–5.45 (m, 6H); 5.60–5.83 (m, 1H); 5.94–6.11 (m, 2H); 7.02 (sextet, 1H); 8.13 (dd, 1H); 8.45 (br d, 1H).

Ms (+ve FAB): 658 (MH)$^+$; 680 (M+Na)$^+$.

EXAMPLE 24

(1R,5S,6S,8R,2'S,4'S)-2-(2-(4-Carboxy-2 -hydroxy-N-methylphenylcarbamoyl)pyrrolidin-4-ylthio)-6-(1-hydroxyethyl)-1-methylcarbapenem-3-carboxylic acid, disodium salt, was prepared from the corresponding allyl protected compound using the method described in example 1, except that the precipitated crude acid was converted to the sodium salt by solution in aqueous sodium bicarbonate and purified by chromatography on CHP20P resin.

NMR (mixture of rotamers): δ 1.06 (d, 3H); 1.15 (d, 3H); 1.52–1.69 (m, 1H); 2.05 (m, 0.5H); 2.19 (m, 0.5H); 3.04 (m, 1H); 3.15, 3.16 (2×s, overlapping m, 5H); 3.38 (m, 1H); 3.67 (m, 1H); 3.84 (t, 0.5H); 3.97 (quintet, 1H); 4.01 (t, 0.5H); 4.12 (dd, 1H); 7.37 (t, 1H); 7.48 (m, 1H); 7.62 (d, 1H).

Ms (+ve FAB): 528 (MH)$^+$, (Na salt)$^+$; 550 (Na$_2$ salt)$^+$.

The starting material was prepared as follows:

Allyl 3-allyloxy-4-aminobenzoate (7 g, 30 mM) was dissolved in triethylorthoformate (70 ml), treated with trifluoroacetic acid (10 drops), and heated under reflux for 5 hours. Solvent was removed by evaporation, and the residual oil was dissolved in ethanol (70 ml), then treated with glacial acetic acid (8.59 ml, 150 mM) followed by sodium cyanoborohydride (9.43 g, 150 mM) in several portions. The mixture was then left to stir at ambient temperature under a blanket of argon for 18 hours. Solvent was removed, and the residue treated with water (50 ml) and extracted into diethyl ether. The combined extracts were washed with water and brine before being dried over MgSO$_4$. After removal of the solvent, the residue was purified by chromatography over silica, eluting with a gradient of dichloromethane/ethyl acetate (100:0 to 95:5), to give allyl 3-allyloxy-4-methylaminobenzoate (3.08 g, 41%).

NMR (CDCl$_3$): δ 2.92 (s, 3H); 4.60 (dt, 2H); 4.77 (dt, 2H); 4.82 (br, 1H); 5.21–5.47 (m, 4H); 5.94–6.18 (m, 2H); 6.53 (d, 1H); 7.42 (d, 1H); 7.68 (dd, 1H).

Ms (CI): 247 (MH)$^+$.

The above amine was condensed with (2S,4S)-4-acetylthio-1 -allyloxycarbonyl-2-carboxypyrrolidine using the method described in example 1, except using the above amine in place of allyl 3-allyoxy-4-amino benzoate, to give (2S,4S)-1-allyloxycarbonyl-2-(2-allyloxy-4 -allyloxycarbonyl-N-methylphenylcarbamoyl)pyrrolidin-4-ylthioacetate.

NMR (mixture of rotamers, CDCl$_3$): δ 1.88 (br m, 1H); 2.21 (m, 1H); 2.29 (s, 3H); 3.20, 3.22 (2×s, 3H); 3.39 (t, 1H); 3.74 (br m, 1H); 3.99 (dd, 1H); 4.28 (t, 1H); 4.60 (m, 4H); 4.85 (d, 2H); 5.17–5.47 (m, 6H); 5.82–6.15 (m, 3H); 7.59–7.77 (m, 3H).

Ms (+re FAB): 503 (MH)$^+$.

The above thioacetate was deacetylated to the corresponding thiol, which was condensed without further purification with allyl (1R,5R,6 S,8R)-6-(1-hydroxyethyl)-1-methyl-2-diphenylphosphoryloxycarbapenem-3-carboxylate, using the method described in example 1 for the preparation of protected carbapenems, to give allyl (1R,5S,6S,8R,2'S,4'S)-2-(1-allyloxycarbonyl-2-(2-allyloxy-4 -allyloxycarbonyl-N-methylphenylcarbamoyl)pyrrolidin-4-ylthio)-6-(1 -hydroxyethyl)-1-methylcarbapenem-3-carboxylate.

NMR (mixture of rotamers, CDCl$_3$): δ 1.18 (m, 3H); 1.32 (d, 3H); 1.96 (m, 1H); 2.11 (m, 1H); 3.20, 3.22 (2×s, 3H); 3.27–3.49 (m, 3H); 3.93 (m, 1H); 4.16–4.30 (m, 4H); 4.57–4.86 (m, 8H); 5.19–5.49 (m, 8H); 5.84–6.14 (m, 4H); 7.61 (d, 1H); 7.67 (d, 1H); 7.74 (dd, 1H).

Ms (+re FAB): 710 (MH)$^+$; 732 (M+Na)$^+$.

EXAMPLE 25

(1R,5S,6S,8R,2'S,4'S)-2-(2-(3-Carboxy-5-chloro-2 -hydroxyphenylcarbamoyl)pyrrolidin-4-ylthio)-6-(1-hydroxyethyl)-1-methylcarbapenem-3-carboxylic acid, disodium salt was prepared from the corresponding allyl protected compound using the method described in example 6.

NMR δ 1.11 (d, 3H); 1.13 (d, 3H); 1.72 (m, part obscured, 1H); 2.50–2.72 (m, 2H); 3.18 (dd, 1H); 3.38 (m, 1H); 3.50 (m, 1H); 3.60 (m, part obscured, 1H); 3.95 (quintet, 1H); 4.04 (t, 1H); 4.14 (dd, 1H); 7.37 (d, 1H); 8.20 (d, 1H).

Ms (+ve FAB): 570/572 (MH)$^+$; 592/594 (M+Na)$^+$.

The starting materials were prepared as follows:

5-Chloro-2-hydroxy-3-nitrobenzoic acid was allylated using the method described in example 1, except using 5-chloro-2-hydroxy-3-nitrobenzoic acid in place of 3-hydroxy-4-nitrobenzoic acid to give allyl 2 -allyloxy-5-chloro-3-nitrobenzoate.

NMR (CDCl$_3$): δ 4.64 (dt, 2H); 4.85 (dt, 2H); 5.26–5.48 (m, 4H); 5.92–6.17 (m, 2H); 7.89 (d, 1H); 7.99 (d, 1H).

Ms (CI): 298/300 (MH)$^+$.

The above nitro compound was reduced by the method described in example 6 for the reduction of allyl 2-methyl-6-nitrobenzoate, except that the solvent was ethanol to give allyl 2-allyloxy-3-amino-5-chlorobenzoate.

NMR (CDCl$_3$): δ 3.95 (br, 2H); 4.45 (dt, 2H); 4.80 (dt, 2H); 5.24–5.47 (m, 4H); 5.93–6.20 (m, 2H); 6.88 (d, 1H); 7.17 (d, 1H).

Ms (CI): 268/270 (MH)$^+$.

The above amine was condensed with (2S,4S)-4-acetylthio-1 -allyloxycarbonyl-2-carboxypyrrolidine using the method described in example 1, except using the above amine in place of allyl 3-allyloxy-4-aminobenzoate and purifying by chromatography using a gradient of dichloromethane/diethyl ether (100:0 to 95:5) to give (2S,4S)-1 -allyloxycarbonyl-2-(2-allyloxy-3-allyloxycarbonyl-5 -chlorophenylcarbamoyl)pyrrolidin-4-ylthioacetate.

NMR (CDCl$_3$): δ 2.31 (s, 3H); 2.48 (br, 1H); 2.66 (br, 1H); 3.39 (dd, 1H); 4.04 (quintet, 1H); 4.13 (dd, 1H); 4.49 (d, 2H); 4.56 '(m, 1H); 4.63 (d, 2H); 4.82 (d, 2H); 5.21–5.49 (m, 6H); 5.82–6.18 (m, 3H); 7.58 (d, 1H); 8.68 (d, 1H); 9.07 (br, 1H).

Ms (+ve FAB): 523/525 (MH)$^+$; 545/547 (M+Na)$^+$.

The above thioacetate was deacetylated to the corresponding thiol, which was condensed without further purification with allyl (1R,5R,6 S,8R)-6-(1-hydroxyethyl)-1-methyl-2-diphenylphosphoryloxycarbapenem-3-carboxylate, using the method described in example 1, for the preparation of protected carbapenems, to give allyl (1R,5S,6S,8R,2'S,4'S)-2-(1-allyloxycarbonyl-2-(2-allyloxy-3-allyloxycarbonyl-5 -chlorophenylcarbamoyl)pyrrolidin-4-ylthio)-6-(1-hydroxyethyl)-1 -methylcarbapenem-3-carboxylate.

NMR (CDCl$_3$): δ 1.15 (d, 3H); 1.37 (d, 3H); 2.48 (br, 1H); 2.69 (br, 1H); 3.26 (dd overlapping m, 2H); 3.41 (dd, 1H); 3.80 (quintet, 1H); 4.10 (br, 1H); 4.24 (dd overlapping m, 2H); 4.45 (t, 1H); 4.52–4.69 (m, 6H); 4.82 (dt, 2H); 5.18–5.46 (m, 8H); 5.82–6.10 (m, 4H); 7.57 (d, 1H); 8.68 (d, 1H); 8.95 (br, 1H).

Ms (+ve FAB): 730/732 (MH)$^+$; 752/754 (M+Na)$^+$.

EXAMPLE 26

(1R,5S,6S,8R,2'S,4'S)-2-(2-(3-Carboxy-2 -hydroxyphenylcarbamoyl)pyrrolidin-4-ylthio)-6-(1-hydroxyethyl)-1-methylcarbapenem-3-carboxylic acid, disodium salt was prepared from the corresponding allyl protected compound using the method described in example 1, except that crude acid was converted to the sodium salt by solution in aqueous sodium bicarbonate, and purified by chromatography on CHP20P resin.

NMR δ 1.20 (d, 6H); 1.99 (m, part obscured, 1H); 2.94 (m, part obscured, 1H); 3.17 (dd, 1H); 3.27 (dd, 1H); 3.42 (quintet, 1H); 3.77 (dd, 1H); 3.92 (quintet, 1H); 4.05 (quintet, 1H); 4.23 (dd, 1H); 4.52 (t, 1H); 6.76 (t, 1H); 7.61 (dd, 1H); 8.11 (dd, 1H).

Ms (+ve FAB): 514 (MH)$^+$; 536 (M+Na)$^+$.

The starting materials were prepared as follows:

2-Hydroxy-3-nitrobenzoic acid was allylated using the method described in example 1, except using 2-hydroxy-3-nitrobenzoic acid in place of 3-hydroxy-4-nitrobenzoic acid to give allyl 2-allyloxy-3-nitrobenzoate.

NMR (CDCl$_3$): δ 4.64 (dt, 2H); 4.84 (dt, 2H); 5.25–5.47 (m, 4H); 5.98–6.17 (m, 2H); 7.27 (t, 1H); 7.90 (dd, 1H) 8.03 (dd, 1H).

Ms (CI): 264 (MH)$^+$.

The above nitro compound was reduced by the method described in example 6, for the reduction of allyl 2-methyl-6-nitrobenzoate, except that the solvent was ethyl acetate, and the crude product was purified by chromatography over silica, eluting with hexane:ethyl acetate 6:1 to give allyl 2-allyloxy-3-aminobenzoate.

NMR (CDCl$_3$): δ 3.84 (br, 2H); 4.47 (dt, 2H); 4.80 (dt, 2H); 5.23–5.45 (m, 4H); 5.96–6.21 (m, 2H); 6.89 (dd, 1H); 6.91 (t, 1H); 7.21 (dd, 1H).

Ms (CI): 234 (MH)$^+$.

The above amine was condensed with (2S,4S)-4-acetylthio-1-allyloxycarbonyl-2-carboxypyrrolidine using the method described in example 1, except using the above amine in place of allyl 3-allyloxy-4-aminobenzoate, purifying by chromatography using a gradient of hexane:ethyl acetate (3:1 to 2:1) to give (2S,4S)-1-allyloxycarbonyl-2-(2-allyloxy-3-allyloxycarbonylphenylcarbamoyl)pyrrolidin-4-ylthioacetate.

NMR (CDCl$_3$): δ 2.30 (s, 3H); 2.44 (br, 1H); 2.68 (br, 1H); 3.40 (dd, 1H); 4.03 (quintet, 1H); 4.16 (dd, 1H); 4.48–4.66 (overlapping m, 5H); 4.82 (dt, 2H); 5.19–5.48 (m, 6H); 5.81–6.20 (m, 3H); 7.17 (t, 1H); 7.61 (dd, 1H); 8.60 (dd, 1H); 8.93 (br, 1H).

Ms (+ve FAB): 489 (MH)$^+$; 511 (M+Na)$^+$.

The above thioacetate was deacetylated to the corresponding thiol, which was condensed without further purification with allyl (1R,5R,6 S,8R)-6-(1-hydroxyethyl)-1-methyl-2-diphenylphosphoryloxycarbapenem-3-carboxylate, using the method described in example 1, to give allyl (1R,5S,6S,8R,2'S,4'S)-2-(1-allyloxycarbonyl-2-(2-allyloxy-3-allyloxycarbonylphenylcarbamoyl)pyrrolidin-4-ylthio)-6-(1-hydroxyethyl)-1-methylcarbapenem-3-carboxylate.

NMR (CDCl$_3$): δ 1.24 (d, 3H); 1.35 (d, 3H); 2.44 (br, 1H); 2.72 (br, 1H); 3.24 (dd overlapping m, 2H); 3.42 (dd, 1H); 3.78 (quintet, 1H); 4.08–4.31 (overlapping m, 3H); 4.43–4.68 (overlapping m, 7H); 4.81 (dt, 2H); 5.17–5.46 (m, 8H); 5.80–6.17 (m, 4H); 7.17 (t, 1H); 7.61 (dd, 1H); 8.60 (dd, 1H); 8.84 (br, 1H).

Ms (+ve FAB): 696 (MH)$^+$; 718 (M+Na)$^+$.

EXAMPLE 27

(1R,5S,6S,8R,2'S,4'S)-2-(2-(4-Carboxy-2-hydroxyphenylcarbamoyl)pyrrolidin-4-ylthio)-6-(1-hydroxyethyl)-1-methylcarbapenem-3-carboxylic acid, disodium salt A solution of allyl (1R,5S,6S,8R,2'S,4'S)-2-(1-allyloxycarbonyl-2-(2 allyloxy-4-allyloxycarbonylphenylcarbamoyl)pyrrolidin-4-ylthio)-6-(1 -hydroxyethyl)-1-methylcarbapenem-3-carboxylate (20 parts) in DMF (128 parts, dried over 4 Å sieves) was added to 2,2-dimethyl-1,3-dioxane-4,6-dione (33.2 parts) which was cooled in a water bath, and the solution purged with argon for 10 minutes. Tetrakis(triphenylphosphine)palladium (3.3 parts) dissolved in distilled THF (60 parts) was then added rapidly, giving a slight exotherm. The reaction was protected from light, and stirred at ambient temperature for 1.5 hours, monitoring the reaction by hplc. Sodium 2-ethylhexanoate (9.6 parts) in distilled THF (45 parts) was added slowly to the stirred solution. The mixture was diluted by the further addition of THF (585 parts) followed by THF (620 parts). The crude solid disodium salt precipitate was filtered, washed and dried.

Crude solid sodium salt was dissolved in methanol (1100 parts, hplc grade) by stirring at ambient temperature for 30 minutes, distilled water (2 parts) was added, and the solution filtered. Product was reprecipitated by the gradual addition of diethyl ether (1800 parts). After 30 minutes, the precipitate was filtered, and washed with with two portions of diethyl ether (140 parts each), and dried to give purified disodium salt (14 parts).

The above sodium salt was divided into four portions (each 3.5 parts). One portion was treated with sodium bicarbonate (1.7 parts) and rapidly dissolved in distilled water (100 parts) by sonication. The solution was filtered and the filter washed with distilled water (two portions of 25 parts). The combined filtrate and washings were applied immediately to a column of Diaion HP20SS resin (1000 parts made up in distilled water). The column was eluted with distilled water. The fractions containing pure product were combined, and freeze-dried. The second portion was dissolved in an impure intermediate fraction and columned as above on the same column. This was repeated for the third and fourth portions. The combined yield of freeze-dried product as the disodium salt trihydrate was 7 parts.

The NMR was consistent with the product of example 1.

The starting materials were prepared as follows:

Preparation of Allyl 3-allyloxy-4-aminobenzoate

3-Hydroxy-4-nitrobenzoic acid (6.5 parts), anhydrous potassium carbonate (14 parts), and allyl bromide (10.8 parts) were mixed in DMF (70 parts), and heated briefly to 60°. The mixture was then stirred for 18 hours at ambient temperature, filtered through celite, and the filter bed washed with DMF (25 parts). The solvent was removed by evaporation, the residue drowned into aqueous sodium bicarbonate (100 parts), and extracted with two portions of ethyl acetate (each of 4.5 parts). The organic solution was washed with water, brine, and dried over MgSO$_4$. After removal of the solvent, the oily residue was purified by chromatography on silica, eluting initially with dichloromethane:hexane 1:1, and then dichloromethane. Appropriate fractions were combined to give allyl 3-allyloxy-4-nitrobenzoate (8.8 parts, 94%).

Stannous chloride dihydrate (22.6 parts) was treated with industrial methylated spirits (70 parts) and heated to 60° to dissolve. The above ester (6.5 parts) was dissolved in industrial methylated spirits (2.8 parts) and run in to the hot solution of tin salt at such a rate as to maintain a gentle reflux (30 minutes). Finally the mixture was heated at reflux for 3 hours. After cooling, solvent was evaporated, and the residue treated with ethyl acetate (125 parts), and stirred in an ice bath. Ammonia (density 0.880 g/ml, 15 parts) was run in, keeping the temperature below 20°, and finally stirring at ambient temperature for 1 hour before filtering. The filtered tin salts were washed with two portions of ethyl acetate (each 45 parts), and the organic solvent evaporated. The oily residue was purified by chromatography on silica, eluting initially with dichloromethane:hexane 3:1, then 1:1, and finally with dichloromethane. Appropriate fractions were combined to give allyl 3-allyloxy-4-aminobenzoate (4.2 parts, 73%).

Preparation of the Pyrrolidin-4-ylthiol Side Chain (2S,4S)-4-Acetylthio-1-allyloxycarbonyl-2-carboxypyrrolidine (9.5 parts) and allyl 3-allyloxy-4-aminobenzoate (8.1 parts) were dissolved in toluene (85 parts) and cooled in an ice-bath. 2-Ethoxy-1-ethoxycarbonyl-1,2-dihydroquinoline (9.4 parts) was added, and the mixture stirred at ambient temperature for 18 hours. After washing with aqueous 2M hydrochloric acid, brine, and drying over $MgSO_4$, solvent was evaporated. Crude material was purified by flash chromatography on silica, eluting initially with dichloromethane, and then dichloromethane:ethyl acetate 9:1. Appropriate fractions were combined to give (2S,4S)-4-acetylthio-1-allyloxy-carbonyl-2-(4-allyloxycarbonyl-2-allyloxyphenylcarbamoyl)pyrrolidine (12.5 parts, 74%).

Preparation of Protected Carbapenem

A solution of allyl (1R,5R,6S,8R)-6-(1-hydroxyethyl)-1-methyl-2-diphenylphosphoryloxycarbapenem-3-carboxylate (15.8 parts) was dissolved in dry acetonitrile (40 parts), degassed by bubbling argon through the solution, and cooled to −19°. N,N-diisopropylethylamine (3.75 parts) was added, followed by a solution of (2S,4S)-1-allyloxycarbonyl-2-(4-allyloxycarbonyl-2-allyloxyphenylcarbamoyl)pyrrolidin-4-ylthiol (12.8 parts, prepared as in example 1) in acetonitrile (40 parts), keeping the temperature below −12°. Finally the mixture was stirred 18 hours at −19°, before solvent was removed. Crude product was purified by HPLC (15–20 μ silica, two 30×10 cm cartridges) eluting with dichloromethane: ethyl acetate 1:1. Appropriate fractions were combined to give allyl (1R,5S,6S,8R,2'S,4'S)-2-(1-allyloxycarbonyl-2-(4-allyloxycarbonyl-2-allyloxyphenylcarbamoyl)pyrrolidin-4-yl-thio)-6-(1-hydroxyethyl)-1-methylcarbapenem-3-carboxylate (12 parts, 59%).

The NMR for each of the above intermediates was consistent with the NMR for the corresponding intermediates of example 1.

EXAMPLE 28

(1R,5S,6S,8R,2'S,4'S)-2-(2-(2-Carboxy-5-nitrophenylcarbamoyl)pyrrolidin-4-ylthio)-6)-(1-hydroxyethyl-1-methylcarbapenem-3-carboxylic acid, disodium salt To a solution of allyl (1R,5S,6S,8R,2'S,4'S)-2-(1-allyloxycarbonyl-2-(2-carboxy-5-nitrophenylcarbamoyl)pyrrolidin-4-ylthio)-6-(1-hydroxyethyl-1-methylcarbapenem-3-carboxylate (262 mg, 0.40 mM) in dichloromethane (5 ml) was added tetrakis(triphenylphosphine)palladium (24 mg, 0.020 mM) and N-methylaniline (176 μl, 1.63 mM). The solution was stirred at ambient temperature for 20 minutes. The reaction mixture was extracted with water (3×5 ml) and the combined aqueous phases treated with sodium bicarbonate (102 mg, 1.2 mM). Chromatography of the aqueous phase on reversed phase silica (Nucleosil C18, 3.5×20 cm) using a gradient of acetonitrile (0–6%) in water gave the title product (34 mg, 15%) as a white amorphous powder after freeze-drying.

NMR ($D_2O$): δ 1.25 (d, 3H); 1.35 (d, 3H); 2.05 (ddd, 1H); 2.85 (ddd, 1H); 3.07 (dd, 1H); 3.3–3.5 (m, 1H); 3.47 (dd, 1H); 3.6 (dd, 1H); 3.8–3.95 (m, 1H); 4.25 (dd, 1H); 4.2–4.35 (m, 2H); 8.1 (s, 2H); 9.15 (s, 1H).

The starting material was prepared as follows:

Preparation of the side chain pyrrolidin-4-ylthioacetate:

To a solution of (2S,4S)-1-allyloxycarbonyl-2-carboxypyrrolidin-4-ylthioacetate (1.5 g, 5.5 mM) in dichloromethane (10 ml) was added $SOCl_2$ (4 ml, 0.055 M) under argon. After stirring at ambient temperature for 4 hours the solvent was evaporated. The residue was triturated in toluene (50 ml) and the mixture was evaporated and dried under vacuum. The product was dissolved in dichloromethane (10 ml) and the resulting solution added dropwise to a solution of 4-nitroanthranilic acid (1 g, 5.5 mM) and N-ethyldiisopropylamine (1.91 ml, 11 mM) in dichloromethane (25 ml) cooled to 0° C. The mixture was stirred at ambient temperature overnight. After evaporation to dryness the crude material was purified by chromatography on HP20SS resin using a gradient of acetonitrile (0–50%) in $H_2O$—AcOH 1% to give (2S,4S)-1-allyloxycarbonyl-2-(2-carboxy-5-nitrophenylcarbamoyl)pyrrolidin-4-ylthioacetate (1.4 g, 58%) as a foam after freeze drying.

NMR (DMSO-$CF_3COOD$): δ 1.85–2.35 (m, 1H); 2.20 (s, 3H); 2.6–3.0 (m, 1H); 3.2–3.6 (m, 1H); 3.8–4.2 (m, 2H); 4.3–4.7 (m, 3H); 4.8–5.5 (m, 2H); 5.5–6.2 (m, 1H); 7.87 (dd, 1H); 8.2 (d, 1H); 9.4 (dd, 1H).

Conversion to Pyrrolidin-4-ylthiol

To a solution of the above thioacetate (0.47 g, 1.07 mM) in ethanol (5 ml) was added a solution of methylamine in ethanol (1.02M) (1.26 ml, 1.29 mM). After stirring at room temperature for 30 minutes the solvent was removed by evaporation and the residue partitioned between ethyl acetate and an aqueous solution of hydrochloric acid. The organic layer was washed with water, then brine and dried ($MgSO_4$), solvent evaporated and used without further purification.

NMR ($CDCl_3$): δ 1.8 (d, 1H); 1.9–2.4 (m, 1H); 2.5–3.1 (m, 1H); 3.2–3.7 (m, 1H); 3.85–4.3 (m, 1H); 4.4–5.0 (m, 4H); 5.0–5.5 (m, 2H); 5.5–6.15 (m, 1H); 7.65–8.3 (m, 2H); 9.57 (dd, 1H).

Preparation of Protected Carbapenem

To a solution of allyl (1R,5R,6S,8R)-6-(1-hydroxyethyl)-1-methyl-2-diphenylphosphoryloxycarbapenem-3-carboxylate (534 mg, 1.07 mM) and N-ethyldiisopropylamine (558 μl, 3.2 mM) in dry DMF (10 ml) was added the above (2S,4S)-1-allyloxycarbonyl-2-(2-carboxy-5-nitrophenylcarbamoyl)pyrrolidin-4-ylthiol dissolved in DMF (3 ml), tri-n-butylphosphine (266 μl, 1.07 mM) and water (19 μl, 1.07 mM). The reaction mixture was stirred at ambient temperature for 2.5 hours and kept at 4° overnight.

The mixture was purified by chromatography on HP20SS with a gradient of acetonitrile (0–42%) in water, to give allyl (1R,5S,6S,8R,2'S,4'S) 2-(1-allyloxycarbonyl-2-(2-carboxy-5-nitrophenylcarbamoyl)pyrrolidin-4-ylthio)-6-(1-hydroxyethyl)-1-methylcarbapenem-3-carboxylate as a foam (537 mg, 78%).

NMR δ 1.14 (m, 6H); 1.75–2.35 (m, 1H); 2.6–4.8(m, 13H); 4.9–5.6 (m, 4H); 5.5–6.25 (m, 2H); 7.85 (dd, 1H); 8.2 (d, 1H); 9.37 (d, 1H).

Ms (+ve FAB): 645 $(MH)^+$; 667 $(M+Na)^+$.

EXAMPLE 29

(1R,5S,6S,8R,2'S,4'S)-2-(2-Carboxy-4-nitrophenylcarbamoyl)pyrrolidin-4-ylthio)-6-(1-hydroxyethyl)-1-methylcarbapenem-3-carboxylic acid, disodium salt To a solution of allyl (1R,5S,6S,8R,2'S,4'S)-2-(1-allyloxycarbonyl-2-(2-carboxy-4-nitrophenylcarbamoyl)pyrrolidin-4-ylthio)-6-(1-hydroxyethyl)- 1-methylcarbapenem-3-carboxylate (540 mg, 0.84 mM) in dichloromethane was added a solution of sodium bicarbonate (176 mg, 2.1 mM) in water (5 ml). To this stirred mixture was added N-methylaniline (545 μl, 5 mM) and tetrakis(triphenylphosphine) palladium (141 mg, 0.12 mM). After stirring at ambient temperature for 45 minutes, the aqueous layer was concentrated under vacuum and adjusted to pH 8. Chromatography on HP20SS resin using a gradient of acetonitrile (0–6%) in water gave the title product (182 mg, 38%) as a white foam after freeze drying.

NMR δ 1.15 (d, 3H); 1.17 (d, 3H); 1.75–1.85 (m, 1H); 2.6–2.75 (m, 2H); 3.19 (dd, 1H); 3.35–3.55 (m, 2H); 3.55–3.67 (m, 1H); 3.9–4.07 (m, 2H); 4.16 (dd, 1H), 8.2 (dd, 1H); 8.75 (d, 1H); 8.81 (d, 1H).

Ms (+ve FAB): 543 (MH)$^+$ (Na salt)$^+$; 565 (Na$_2$ salt)$^+$.

The starting material was prepared as follows:

(2S,4S)-1-Allyloxycarbonyl-2-(2-carboxy-4 -nitrophenylcarbamoyl)pyrrolidine-4-ylthioacetate was prepared as described in example 28, except using 2-amino-5-nitrobenzoic acid in place of 4-nitroanthranilic acid (yield: 58%).

NMR δ 1.85–2.4 (m, 1H); 2.27 (s, 3H), 2.65–3.1 (m, 1H); 3.25–3.65 (m, 1H); 3.85–4.3 (m, 2H); 4.4–4.7 (m, 3H); 5.0–5.4 (m, 2H); 5.65–6.15 (m, 1H); 8.38 (dd, 1H); 8.77 (2d, 2H).

The resulting thioacetate was converted to the thiol and coupled with allyl (1R,5R,6S,8R)-6-(1-hydroxyethyl)-1-methyl-2 -diphenylphosphoryloxycarbapenem-3-carboxylate as described in example 28, to give allyl (1R,5S,6S,8R,2'S,4'S)-2-(2-(1-allyloxycarbonyl)-2-(2-carboxy-4-nitrophenylcarbamoyl)pyrrolidin-4-ylthio)-6-(1-hydroxyethyl)-1 -methylcarbapenem-3-carboxylate (yield: 88%).

NMR δ 1.15–1.25 (m, 6H); 1.9–2.1 (m, 1H); 2.75–2.95 (m, 1H); 3.0–3.2 (m, 1H); 3.23 (dd, 1H); 3.35–3.55 (m, 2H); 3.9–4.1 (m, 2H); 4.12 (dd, 1H); 4.22 (dd, 1H); 4.4–4.7 (m, 4H); 5.14 (d, 2H); 5.33 (d, 2H); 5.7–6.0 (m, 2H); 8.24 (dd, 1H); 8.7 (d, 1H); 8.8 (d, 1H).

Ms (+ve FAB): 667 (MH)$^+$; (Na salt)$^+$.

EXAMPLE 30

(1R,5S,6S,8R,2'S,4'S)-2-(2-(2-Carboxy-5 -methoxycarbonylphenylcarbamoyl) pyrrolidin-4-ylthio)-6-(1-hydroxyethyl)-1 -methylcarbapenem-3-carboxylic acid, dipotassium salt To a solution of allyl (1R,5S,6S,8R,2'S,4'S)-2-(2-(2-carboxy-5 -methoxycarbonylphenylcarbamoyl)-1-(4 -nitrobenzyloxycarbonyl)pyrrolidin-4-ylthio)-6-(1-hydroxyethyl)-1-methylcarbapenem-3-carboxylate (500 mg, 0.665 mM) in a mixture of ethyl acetate (12 ml) and dichloromethane (12 ml) was added triphenylphosphine (87 mg, 0.33 mM), a 0.825M solution of potassium 2-ethylhexanoate in ethyl acetate (1.77 ml, 1.46 mM) and tetrakis(triphenylphosphine) palladium (77 mg 0.065 mM). The mixture was stirred at ambient temperature for 1 hour. After centrifugation the precipitate was treated with ethyl acetate and dried under vacuum. After dissolution of the resulting solid in a mixture of water (10 ml) and ethyl acetate (10 ml), 10% palladium-carbon (350 mg) was added. The mixture was hydrogenated at ambient temperature and atmospheric pressure for 2 hours. After filtration of the catalyst, the compound was purified by reverse phase chromatography (Nucleosil C18, 3.5×20 cm) using a gradient of acetonitrile (0–4%) in water to give the title compound as a foam after freeze drying (90 mg, 22%).

NMR δ 1.15 (d, 6H); 1.75–1.9 (m, 1H), 2.65–2.8 (m, 1H); 2.82 (dd, 1H); 3.2 (dd, 1H); 3.35–3.45 (m, 1H); 3.5–3.6 (m, 1H); 3.65–3.75 (m, 1H); 3.85 (s, 3H); 3.95 (m, 1H); 4.15 (m, 2H); 7.63 (dd, 1H); 8.08 (d, 1H); 9.15 (d, 1H).

The starting material was prepared as follows:

Methyl 3-amino-4-carboxybenzoate

A solution of methyl 4-carboxy-3-nitrobenzoate (3 g, 13.3 mM) in ethanol (20 ml) was hydrogenated at atmospheric pressure in the presence of 10% palladium-carbon (1 g) for 40 minutes. After filtration of the catalyst, the solid was recrystallised from ethanol to give methyl 3-amino-4-carboxybenzoate (1.7 g, 65%).

NMR δ 3.83 (s, 3H); 7.05 (dd, 1H); 7.45 (d, 1H); 7.8 (d, 1H).

The above benzoate was reacted with (2S,4S)-1-(4 -nitrobenzyloxycarbonyl)-2-carboxypyrrolidinethioacetate as described in example 28 for the corresponding allyl protected thioacetate, to give (2S,4S)-2-(2-carboxy-5-methoxycarbonylphenylcarbamoyl)-1-(4 -nitrobenzyloxycarbonyl)pyrrolidin-4-ylthioacetate.

NMR δ 1.75–2.35 (m, 1H); 2.26 (s, 3H); 2.6–3.1 (m, 1H); 3.2–3.65 (m, 1H); 3.9 (s, 3H); 3.7–4.3 (m, 2H); 4.5 (dd, 1H); 4.95–5.45 (m, 2H); 7.15 (s, 1H); 7.35–8.25 (m, 6H); 9.05 (br s, 1H).

Preparation of protected carbapenem:

Allyl (1R,5S,6S,8R,2'S,4'S)-2-(2-(2-carboxy-5 -methoxycarbonylphenylcarbamoyl)-1-(4-nitrobenzyloxycarbonyl)pyrrolidin-4-ylthio)-6-(1 -hydroxyethyl)-1-methylcarbapenem-5-carboxylate was prepared from the above pyrrolidin-4-ylthioacetate by the method described in example 28 (yield: 82%).

NMR δ 1.16 (d, 6H); 2.0–2.1 (m, 1H); 2.8–3.0 (m, 1H); 3.25 (dd, 1H); 3.4–3.6 (m, 2H); 3.9 (s, 3H); 3.9–4.1 (m, 2H); 4.1–4.3 (m, 2H); 4.4–4.6 (m, 3H); 5.0–5.4 (m, 4H); 5.7–5.9 (m, 1H); 7.1–8.3 (m, 6H); 9.05–9.25 (m, 1H).

EXAMPLE 31

(1R,5S,6S,8R,2'S,4'S)-2-(2-(2-Carboxy-4 -methoxyphenylcarbamoylpyrrolidin-4-ylthiol)-6- (1-hydroxyethyl)-1-methylcarbapenem-3-carboxylic acid, dipotassium salt The title compound was prepared from the corresponding allyl protected compound by the method described in example 30 (yield: 34%).

NMR δ 1.15 (m, 6H); 1.7–1.85 (m, 1H); 2.6–2.75 (m, 1H); 2.75 (dd, 1H); 3.19 (dd, 1H); 3.3–3.4 (m 1H); 3.45–3.5 (m, 1H); 3.6–3.7 (m, 1H); 3.75 (s, 3H); 3.9–4.1 (m, 2H); 4.15 (dd, 1H); 7.03 (dd, 1H); 7.51 (d, 1H); 8.44 (d, 1H).

Ms (+ve FAB): 544 MH$^+$ (K salt)$^+$; 582 (K$_2$ salt)$^+$.

The starting material was prepared as follows:

(2S,4S)-2-(2-Carboxy-4-methoxyphenylcarbamoyl)-1-(4 -nitrobenzyloxycarbonyl)pyrrolidin-4-ylthioacetate was prepared by the method described in example 30 except using 2-amino-4-methoxybenzoic acid in place of methyl 3-amino-4-carboxybenzoate.

NMR δ 1.18–2.35 (m, 1H); 2.27 (s, 3H); 2.7–3.1 (m, 1H); 3.2–3.65 (m, 1H); 3.77 (s, 3H); 3.85–4.3 (m, 2H); 4.25–4.65 (m, 1H); 4.85–5.5 (m, 2H); 7.15 (dd, 1H); 7.2–8.4 (m, 5H); 8.4 (d, 1H).

Preparation of protected carbapenem:

Allyl (1R,5S,6S,8R,2'S,4'S)-2-(2-(2-carboxy-4-methoxyphenylcarbamoyl)- 1-(4-nitrobenzyloxycarbonyl)pyrrolidin-4-ylthio)-6-(1-hydroxyethyl)-1-methylcarbapenem-3-carboxylate was prepared from the above pyrrolidin-4-ylthioacetate by the method described in example 28.

NMR δ 1.1–1.2 (m, 6H); 1.95–2.1 (m, 1H); 2.8–2.95 (m, 1H); 3.25 (dd, 1H); 3.35–3.55 (m, 2H); 3.75 (s, 3H); 3.9–4.0 (m, 2H); 4.1–4.3 (m, 2H); 4.3–4.6 (m, 3H); 5.0–5.4 (m, 4H); 5.7–5.9; (m, 1H); 7.1 (dd, 1H); 7.3–8.3 (m, 5H); 8.45 (m, 1H).

Ms (+ve FAB): 725 (MH)+.

EXAMPLE 32

(1R,5S,6S,8R,2'S,4'S)-2-(2-(4-Acetamido-2 -carboxyphenylcarbamoyl)pyrrolidin- 4-ylthio)-6-(1-hydroxyethyl)-1-methylcarbapenem-3 -carboxylic acid, disodium salt To a solution of allyl (1R,5S,6S,8R,2'S,4'S)-2-(2-(4-acetamido-2 -carboxyphenylcarbamoyl)pyrrolidin-4-ylthio)-6-(1-hydroxyethyl)-1 -methylcarbapenem-3-carboxylate (250 mg, 036 mM) in dichloromethane (4 ml) was added a solution of sodium bicarbonate (90 mg, 1 mM) in water (4 ml), followed by N-methylaniline (230 mg, 2.16 mM) and tetrakis(triphenylphosphine)palladium (41 mg, 0.036 mM). After stirring at ambient temperature for 15 minutes, the aqueous layer was purified on reversed phase chromatography (Nucleosil C18, 3.5×20 cm) using a gradient of acetonitrile (4%) in water to give the title carbapenem as a foam after freeze drying (59 mg, 27%).

NMR (DMSO d$_6$): δ 1.1–1.2 (2d, 6H); 1.65–1.8 (m, 1H); 2.0 (s, 3H); 2.6–2.7 (m, 2H); 3.15 (dd, 1H); 3.4 (m, 1H); 3.5–3.7 (m, 2H); 3.9 (m, 1H); 4.0 (m, 1H); 4.15 (dd, 1H); 7.75 (dd, 1H); 8.15 (d, 1H); 8.45 (d, 1H).

The starting material was prepared as follows:

Allyl 5-amino-2-nitrobenzoate:

5-Amino-2-nitrobenzoic acid (4 g, 22 mM) was dissolved in DMF (40 ml) and anhydrous potassium carbonate (3.64 g, 26.4 mM) added while stirring. Allyl bromide (3.86 g, 26.4 mM) was added and the mixture stirred at ambient temperature overnight. The solvent was removed by evaporation and the residue taken up in acetonitrile. The organic layer was washed with water, dried (MgSO$_4$) evaporated and purified by silica chromatography with acetonitrile/petroleum ether (40/60) to give allyl 5-amino-2-nitrobenzoate as a yellow solid (3.46 g, 71%).

NMR (CDCl$_3$) δ 4.4 (s, 2H); 4.7–4.9 (m, 2H); 5.1–5.55 (m, 2H): 5.75–6.25 (m, 1H); 6.5–6.76 (m, 2H); 7.9 (d, 1H);

Allyl 5-acetamido-2-nitrobenzoate

A solution of acetyl chloride (3.18 g, 40.5 mM) in dichloromethane (10 ml) under an argon atmosphere was added at 0° to a solution of allyl 5-amino-2-nitrobenzoate (3.0 g, 13.5 mM) in dichloromethane (30 ml). After addition of a solution of triethylamine (1.88 ml, 13.5 mM) in dichloromethane (10 ml) the mixture was stirred at ambient temperature overnight. The solvent was evaporated and the residue purified by chromatography on silica. Elution with ethyl acetate/petroleum ether (50/50) gave allyl 5-acetamido-2-nitrobenzoate (3.36 g, 94%).

NMR (CDCl$_3$) δ: 2.3 (s, 3H); 4.75–5.0 (m, 2H); 5.2–5.6 (m, 2H); 5.8–6.3 (m, 2H); 7.5–8.2 (m, 3H).

Allyl 2-amino-5-acetamidobenzoate:

A suspension of allyl 5-acetamido-2-nitrobenzoate (3.2 g, 12.1 mM) and SnCl$_2$.2H$_2$O (13.7 g, 60.6 mM) in methanol was heated at 60° C. for 30 minutes. The solvent was evaporated and the residue taken up in ethyl acetate. The organic solution was washed with diluted ammonia, brine, dried (MgSO$_4$) and evaporated. Chromatography on silica using ethyl acetate/petroleum ether (60/40) gave 2-amino-5-acetamidobenzoate (2.36 g, 83%).

NMR (CDCl$_3$): δ 2.1 (s, 3H); 4.7–4.9 (m, 2H); 5.1–5.55 (m, 2H); 5.55–5.75 (s, 2H); 5.75–6.3 (m, 1H); 6.6 (d, 1H); 7.25 (s, 1H); 7.5 (dd, 1H); 7.85 (d, 1H).

(2S,4S)-1-Allyloxycarbonyl-2-(5-acetamido-2 -carboxyphenylcarbamoyl)pyrrolidin-4-ylthioacetate was prepared as described in example 28 except using allyl 2-amino-5-acetamidobenzoate in place of 4-nitroanthranilic acid (yield: 70%).

NMR (CDCl$_3$): δ 2.1 (s, 3H); 2.3 (s, 3H); 2.26 (m, 1H); 2.6–3.0 (m, 1H); 3.5 (m, 1H); 3.85–4.8 (m, 7H); 5.55 (m, 4H); 5.75–6.5 (m, 2H); 7.5 (s, 1H); 7.7 (dd, 1H); 7.85 (s, 1H); 8.3 (d, 1H); 8.6 (d, 1H).

Preparation of the protected carbapenem

Allyl (1R,5S,6S,8R,2'S,4'S)-2-(1-allyloxycarbonyl-2-(4-acetamido-2 -carboxyphenylcarbamoyl)pyrrolidin-4-ylthio)-6-(1-hydroxyethyl)-1 -methylcarbapenem-3-carboxylate was prepared from the above pyrrolidin-4-ylthioacetate by the method described in example 28 (yield: 67%).

NMR (CDCl$_3$): δ 1.2 (d, 3H); 1.35 (d, 3H); 2.15 (s, 3H); 2.2 (m, 1H); 2.8 (m, 1H); 3.25 (dd, 1H); 3.3 (s, 1H); 3.6 (dd, 1H); 3.8 (m, 1H); 4.1 (q, 1H); 4.25 (m, 2H); 4.4–4.85 (m, 8H); 5.0–5.55 (m, 6H); 5.7–6.1 (m, 3H); 7.4–7.8 (m, 3H); 8.3 (s, 1H); 8.6 (s, 1H).

EXAMPLE 33

(1R,5R,6S,8R,2'S,4'S)-2-(2-(2-carboxy-4 -sulphophenylcarbamoyl)pyrrolidin-4-yl-thio)-6 -(1-hydroxyethyl)-1-methylcarbapenem-3-carboxylic acid tripotassium salt To a solution of 4-nitrobenzyl (1R,5S,6S,8R,2'S,4'S)-2-(2-(2-carboxy- 4-sulphocarbamoyl)-1-(4-nitrobenzyloxycarbonyl)pyrrolidin-4-ylthio)-6-( 1-hydroxyethyl)-1-methylcarbapenem-3-carboxylate (500 mg, 0.575 mM) in water (20 ml) was added 10% palladium-carbon (350 mg) and potassium bicarbonate (173 mg, 1.73 mM). Catalytic hydrogenation was performed at ambient temperature and atmospheric pressure for 1.5 hours. After filtration of the catalyst, the compound was purified by reverse phase chromatography (Nucleosil C18, 3.5×20 cm using water as eluant to give the title compound as a foam after freeze drying (150 mg, 40%).

NMR δ 1.16 (m, 6H); 1.77 (m, 1H); 2.7 (m, 2H) 3.19 (dd, 1H); 3,4 (m, 1H); 3.5 (m, 1H); 3.65 (m, 1H); 3.97 (m, 2H); 4.15 (dd, 1H); 7.69 (dd, 1H); 8.28 (d, 1H); 8.52 (d, 1H).

The starting material was prepared as follows:

2-Amino-5-sulphobenzoic acid:

A solution of 2-aminobenzoic acid (2g, 15 mM) in oleum (30 ml) was heated at 80°, under argon atmosphere for 2 hours. The mixture was poured into diethyl ether (400 ml) and the resulting precipitate was filtered, washed with diethyl ether and dried under vacuum to give 2-amino-5-sulphobenzoic acid (1.8 g, 57%).

NMR δ 6.8 (d, 1H); 7.55 (dd, 1H); 8.07 (d, 1H).

(2S,4S)-2-(2-Carboxy-4-sulphophenylcarbamoyl)-1-(4 -nitrobenzyloxycarbonyl)pyrrolidin-4-ylthioacetate was prepared by reacting the above acid with (2S,4S)-1-(4-nitrobenzyloxycarbonyl)-2-carboxypyrrolidinethioacetate, as described in example 28 for the allyl protected thioacetate (yield: 61%).

NMR δ 2.1 (m, 1H); 2.27 (s, 3H); 2.85 (m, 1H); 3.45 (m, 1H); 4.05 (m, 1H); 4.15 (m, 1H); 4.5 (m, 1H); 5.25 (m, 2H); 7.55 (m, 2H); 7.8 (d, 1H); 8.1 (m, 2H); 8.3 (s, 1H); 8.5 (d, 1H).

The above thioacetate was converted to the corresponding thiol and coupled with 4-nitrobenzyl (1R,5R,6S,8R)-6-(1-hydroxyethyl)-1-methyl- 2-diphenylphosphoryloxycarbapenem-3-carboxylate, both steps as described in example 28, the latter step as for the coupling with the allyl protected carbapenem, to give 4-nitrobenzyl (1R,5S,6S,8R,2'S,4'S)-2-(2-(2-carboxy-4-sulphocarbamoyl)-1-(4 -nitrobenzyloxycarbonyl)pyrrolidin-4-ylthio)-6-(1-hydroxyethyl)-1 -methylcarbapenem-3-carboxylate (yield: 60%).

NMR δ 1.07 (d, 6H); 2.1 (m, 1H); 2.9 (m, 1H); 3.29 (dd, 1H); 3.5 (m, 2H); 4.0 (m, 2H); 4.05–4.30 (m, 2H); 4.5 (m, 1H); 5.05–5.45 (m, 4H); 7.4–8.6 (m, 11H).

EXAMPLE 34

(1R,5S,6S,8R,2'S,4'S)-2-(2-(2-Carboxy-5 -aminocarbonylphenylcarbamoyl)pyrrolidin-4-ylthio)- 6-(1-hydroxyethyl)-1-methylcarbapenem-3-carboxylic acid.

To a solution of 4-nitrobenzyl (1R,5S,6S,8R,2'S,4'S)-2-(2-(2 -allyloxycarbonyl-5-aminocarbonylphenylcarbamoyl)-1-(4 -nitrobenzyloxycarbonyl)pyrrolidin-4-ylthio)-6-(1-hydroxyethyl)-1-methylcarbapenem-3-carboxylate (440 mg, 0.51 mM) and Meldrum's acid (220 mg, 1.53 mM) in DMF (1 ml), under an atmosphere of argon, was added tetrakis(triphenylphosphine)palladium (60 mg, 0.052 mM). The mixture was stirred at ambient temperature for 30 minutes. The mixture was diluted with diethyl ether and a pale brown solid precipitated. The solid was washed three times with diethyl ether and filtered. To this solid (300 mg) dissolved in a mixture of THF (15 ml) and water (10 ml) was added 10% palladium-carbon (150 mg) and the mixture hydrogenated for 3 hours. The catalyst was filtered, the filtrate was extracted with ethyl acetate (30 ml) and diethyl ether (30 ml), and the aqueous layer was freeze-dried to give the title product (107 mg).

NMR δ 1.16 (s, 6H); 1.98–2.02 (m, 1H); 2.64–2.91 (m, 1H); 3.08 (dd, 1H); 3.26 (dd, 1H); 3.43 (quintet, 1H); 3.71 (dd, 1H); 3.89 (t, 1H); 4.03 (t, 1H); 4.21 (dd, 1H); 4.40 (t, 1H); 8.04 (dd, 1H); 8.57 (d, 1H); 8.60 (d, 1H).

The starting material was prepared as follows:

4-Aminocarbonyl-2-nitrobenzoic acid was allylated using the method described in example 1, except using 4-aminocarbonyl-2-nitrobenzoic acid in place of 3-hydroxy-4-nitrobenzoic acid to give allyl 4-aminocarbonyl-2-nitrobenzoate.

NMR δ 4.81–4.90 (m, 2H); 5.29–5.49 (m, 2H); 5.90–6.17 (m, 1H); 8.18 (d, 1H); 8.36 (d, 1H); 8.38 (s, 1H).

Allyl 4-aminocarbonyl-2-nitrobenzoate was reduced to allyl 4-aminocarbonyl-2-aminobenzoate using stannous chloride as described in example 6.

NMR δ 4.75–4.79 (m, 2H); 5.24–5.44 (m, 2H); 5.96–6.13 (m, 1H); 6.76 (d, 1H); 7.76 (dd, 1H); 8.34 (d, 1H).

Preparation of the Pyrrolidin-4-ylthiol Side Chain.

The above allyl 4-aminocarbonyl-2-aminobenzoate was condensed with 4-acetylthio-1-(4-nitrobenzyloxycarbonyl)- 2-carboxypyrrolidine using the method described in example 1, except that purification was by flash chromatography with ethyl acetate as eluant, giving (2S,4S)-1-(4 -nitrobenzyloxycarbonyl)-2-(2-allyloxycarbonyl-5 -aminocarbonylphenylcarbamoyl)pyrrolidin-4-ylthioacetate.

NMR δ 2.06 (quintet, 1H); 2.85 (m, 1H); 3.40 (dd, 1H); 4.02 (quintet, 1H); 4.15 (dd, 1H); 4.53 (dd, 1H); 4.77 (m, 2H); 5.22 (dd, 2H); 5.25–5.42 (m, 2H); 5.95–6.10 (m, 1H); 7.30 (br, 2H); 7.54 (d, 2H); 8.02–8.10 (m, 3H); 8.42–8.48 (m, 2H), 11.05 (br, 1H).

Preparation of Protected Carbapenem

A solution of 4-nitrobenzyl (1R,5R,6S,8R)-6-(1-hydroxyethyl)-1-methyl- 2-diphenylphosphoryloxycarbapenem-3-carboxylate (530 mg, 0.89 mM) and 1-(4-nitrobenzyloxycarbonyl)-2-(2-allyloxycarbonyl-5 -aminocarbonylphenylcarbamoyl)pyrrolidin-4-ylthiol (450 mg, 0.85 mM) in acetonitrile (20 ml) was purged with argon and cooled in an ice bath, then N-ethyldiisopropylamine (0.45 ml, 0.47 mM) was added. The mixture was stirred at 5° for 20 hours, the solvent removed and the yellow gum purified by flash chromatography on silica eluting with ethyl acetate, then 5% methanol in ethyl acetate, giving 4-nitrobenzyl (1R,5R,6S,8R,2'S,4'S)-2-(2-(2-allyloxycarbonyl-5 -aminocarbonylphenylcarbamoyl)-1-(4-nitrobenzyloxycarbonyl)pyrrolidin-4-ylthio)-6-(1 -hydroxyethyl)-1-methylcarbapenem-3-carboxylate as a white solid (440 mg).

NMR δ 1.17 (d, 6H); 2.02–2.12 (m, 1H); 2.81–2.96 (m, 1H); 3.40–3.60 (m, 2H); 3.95–4.31 (m, 4H); 4.46–4.80 (br, 3H); 5.01–5.43 (m, 6H); 5.89–6.06 (m, 1H); 7.37- 8.58 (complex pattern of doublets and double doublets, 11H).

The thiol for the above reaction was generated from its thioacetate by the method described in example 28.

We claim:

1. A carbapenem compound of the formula (I)

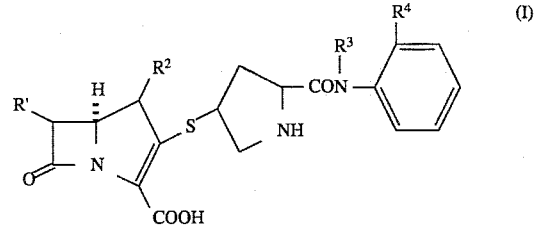

wherein:

R¹ is 1-hydroxyethyl, 1-fluoroethyl or hydroxymethyl;

R² is hydrogen or $C_{1-4}$alkyl;

R³ is hydrogen or $C_{1-4}$alkyl;

R⁴ is hydroxy or carboxy; and the phenyl ring is optionally further substituted by one or two substitutents selected from halo, cyano, $C_{1-4}$alkyl, nitro, hydroxy, carboxy, $C_{1-4}$alkoxy, trifluoromethyl, $C_{1-4}$alkoxycarbonyl, carbamoyl, $C_{1-4}$alkylcarbamoyl, di-$C_{1-4}$alkylcarbamoyl, amino, $C_{1-4}$alkylamino, di-$C_{1-4}$alkylamino, sulphonic acid, $C_{1-4}$alkylS(O)n— (wherein n is 0–2), N-$C_{1-4}$alkanesulphonamido, $C_{1-4}$alkanoylamino and $C_{1-4}$alkanoyl (N-C $_{1-4}$alkyl)amino:

provided that the phenyl ring is substituted by at least one carboxy; or a pharmaceutically acceptable salt or in vivo hydrolysable ester thereof.

2. A compound according to claim 1 wherein R¹ is 1-hydroxyethyl.

3. A compound according to claim 1 wherein R² is hydrogen or methyl.

4. A compound according to claim 1 wherein R³ is hydrogen or methyl.

5. A compound according to claim 1 wherein R³ is hydrogen.

6. A compound according to claim 1 of the formula (IV):

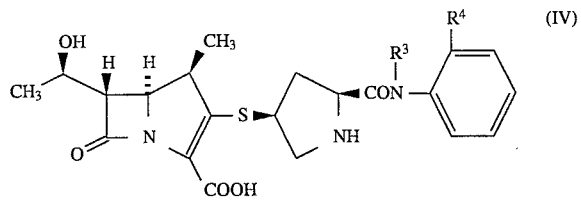

wherein $R^3$ and $R^4$ are as defined in claim 1 and wherein the phenyl ring is optionally substituted as defined in claim 1;

or a pharmaceutically acceptable salt or in vivo hydrolysable ester thereof.

7. A compound according to claim 6 wherein the phenyl ring is optionally further substituted by one or two substituents selected from methyl, ethyl, hydroxy, carboxy, cyano, chloro, bromo, nitro, methoxy and ethoxy.

8. A compound according to claim 6 wherein the phenyl ring is optionally further substituted by one or two substitutents selected from methyl, hydroxy, chloro and carboxy.

9. A compound according to claim 1 selected from (1R,5S,6S,8R,2'S,4'S)-2-(2-(4-carboxy-2 -hydroxyphenylcarbamoyl)pyrrolidin- 4-ylthio)-6-(1-hydroxyethyl)-1-methylcarbapenem-3-carboxylic acid;

(1R,5S,6S,8R,2'S,4'S)-2-(2-(5-carboxy-2 -hydroxyphenylcarbamoyl)pyrrolidin-4-ylthio)-6-(1-hydroxyethyl)-1-methylcarbapenem-3 -carboxylic acid;

(1R,5S,6S,8R,2'S,4'S)-2-(2-(2,5 -dicarboxyphenylcarbamoyl)pyrrolidin-4-ylthio)-6-(1-hydroxyethyl)-1-methylcarbapenem-3 -carboxylic acid;

(1R,5S,6S,8R,2'S,4'S)-2-(2-(2,3 -dicarboxyphenylcarbamoyl)pyrrolidin-4-ylthio)-6-(1-hydroxyethyl)-1-methylcarbapenem-3 -carboxylic acid;

(1R,5S,6S,8R,2'S,4'S)-2-(2-(2 -carboxyphenylcarbamoyl)pyrrolidin-4 -ylthio)-6-(1-hydroxyethyl)-1-methylcarbapenem-3-carboxylic acid;

(1R,5S,6S,8R,2'S,4'S)-2-(2-(2-carboxy-3 -methylphenylcarbamoyl)pyrrolidin-4-ylthio)-6-(1-hydroxyethyl)-1-methylcarbapenem-3 -carboxylic acid;

(1R,5S,6S,8R,2'S,4'S)-2-(2-(2-carboxy-4 -methylphenylcarbamoyl)pyrrolidin-4-ylthio)-6-(1-hydroxyethyl)-1-methylcarbapenem-3 -carboxylic acid;

(1R,5S,6S,8R,2'S,4'S)-2-(2-(2-carboxy-4 -chlorophenylcarbamoyl)pyrrolidin-4-ylthio)-6-(1-hydroxyethyl)-1-methylcarbapenem-3 -carboxylic acid;

(1R,5S,6S,8R,2'S,4'S)-2-(2-(2-carboxy-6 -hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-6 -chlorophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5 -chlorophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-6 -methylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2,4 -dicarboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2,6 -dicarboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-6 -methoxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5 -trifluoromethylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5 -methylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4 -fluorophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5 -fluorophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-hydroxy-3-chloro-6 -carboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5 -carbamoylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4 -methylthiophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4 -methylsulphinylphenylcarbamoyl)pyrrolidin-4-ylthio)-6-(1-hydroxyethyl)-1-methylcarbapenem-3 -carboxylic acid;

(1R,5S,6S,8R,2'S,4'S)-2-(2-(2-carboxy-4 -methylsulphonylphenylcarbamoyl)pyrrolidin-4-ylthio)-6-(1-hydroxyethyl)-1-methylcarbapenem-3 -carboxylic acid;

(1R,5S,6S,8R,2'S,4'S)-2-(2-(2-carboxy-4 -hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4,5 -dimethoxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-3 -hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-3 -methoxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-hydroxy-4-carboxy-5 -chlorophenylcarbamoyl)pyrrolidin-4-ylthio)-6-(1-hydroxyethyl)-1-methylcarbapenem-3 -carboxylic acid;

(1R,5S,6S,8R,2'S,4'S)-2-(2-(2-carboxy-5 -nitrophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5 -methoxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4 -methoxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4 -nitrophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4 -(N-methylacetamido)phenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4 -sulphophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(3-carboxy-2-hydroxy-5 -chlorophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(3-carboxy-2 -hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(4-carboxy-2 -hydroxyphenyl-N-methylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-3 -methoxycarbonylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-3 -nitrophenylcarbamoyl)pyrrolidin-4-yl thio)-6-(1-hydroxyethyl)-1-methylcarbapenem-3-carboxylic acid;

(1R,5S,6S,8R,2'S,4'S)-2-(2-(2-carboxy-4 -carbamoylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-3 -carbamoylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4 -cyanophenylcarbamoyl)pyrrolidin-4-ylthio)-6-(1-hydroxyethyl)-1-methylcarbapenem-3 -carboxylic acid;

(1R,5S,6S,8R,2'S,4'S)-2-(2-(2-carboxy-5 -cyanophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-5 -hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-6 -(N-methylacetamido)phenylcarbamoyl)pyrrolidin-4-ylthio)-6-(1-hydroxyethyl)-1-methylcarbapenem-3-carboxylic acid; and (1R,5S,6S,8R,2'S,4'S)-2-(2-(2,5-di-carboxy-4 -aminophenylcarbamoyl)pyrrolidin-4-ylthio)-6-(1-hydroxyethyl)-1-methylcarbapenem-3-carboxylic acid;

or a pharmaceutically acceptable salt or in vivo hydrolysable ester thereof.

10. A compound according to claim 1 selected from (1R,5S,6S,8R,2'S,4'S)-2-(2-(4-carboxy-2 -hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(5-carboxy-2 -hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2,5 -dicarboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2,3 -dicarboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxyphenylcarbamoyl)pyrrolidin-4 -ylthio)-6-(1-hydroxyethyl)-1-methylcarbapenem-3-carboxylic acid;

(1R,5S,6S,8R,2'S,4'S)-2-(2-(2-carboxy-3 -methylphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2-carboxy-4 -methylphenylcarbamoyl)-pyrrolidin-4-ylthio)-6-(1-hydroxyethyl)-1-methylcarbapenem-3-carboxylic acid;

(1R,5S,6S,8R,2'S,4'S)-2-(2-(6-carboxy-2 -hydroxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(5-carboxy-2-hydroxy-3 -chlorophenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2,4 -dicarboxyphenylcarbamoyl)pyrrolidin-4-ylthio)-6-(1-hydroxyethyl)-1-methylcarbapenem-3-carboxylic acid;

(1R,5S,6S,8R,2'S,4'S)-2-(2-(2,6 -dicarboxyphenylcarbamoyl)pyrrolidin-4-ylthio)-6-(1-hydroxyethyl)-1-methylcarbapenem-3-carboxylic acid; and (1R,5S,6S,8R,2'S,4'S)-2-(2-(2-carboxy-4 -chlorophenylcarbamoyl)pyrrolidin-4-ylthio)-6-(1-hydroxyethyl)-1-methylcarbapenem-3-carboxylic acid;

or a pharmaceutically acceptable salt or in vivo hydrolysable ester thereof.

11. A pharmaceutical composition which comprises a compound according to claim 1 and a pharmaceutically acceptable carrier.

12. A carbapenem compound of formula (I):

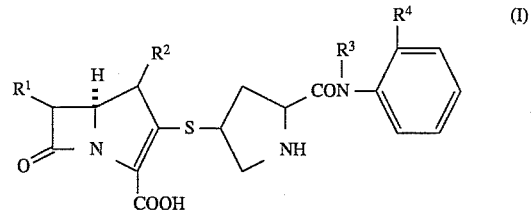

wherein:

$R^1$ is 1-hydroxyethyl, 1-fluoroethyl or hydroxymethyl;

$R^2$ is hydrogen or $C_{1-4}$alkyl;

$R^3$ is hydrogen or $C_{1-4}$alkyl;

$R^4$ is hydroxy or carboxy; and the phenyl ring is optionally further substituted by one or two substituents selected from halo, cyano, $C_{1-4}$alkyl, nitro, hydroxy, carboxy, $C_{1-4}$alkoxy, trifluoromethyl, $C_{1-4}$alkoxycarbonyl, carbamoyl, $C_{1-4}$alkycarbamoyl, di-$C_{1-4}$alkylcarbamoyl, amino, $C_{1-4}$alkylamino, di-$C_{1-4}$alkylamino, sulphonic acid, $C_{1-4}$alkylS(O)$_n$— (wherein n is 0–2), N-$C_{1-4}$alkanesulphonamido, $C_{1-4}$alkanoylamino and $C_{1-4}$alkanoyl (N-$C_{1-4}$alkyl)amino:

provided that the phenyl ring is substituted by at least one carboxy; or a non pharmaceutically acceptable salt thereof.

13. A compound of the formula (V):

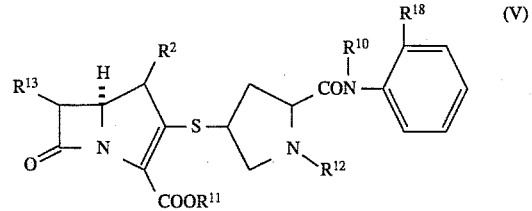

wherein:

$R^2$ is hydrogen or $C_{1-4}$alkyl;

$R^{10}$ is hydrogen or $C_{1-4}$alkyl, or an amino protecting group;

$R^{13}$ is 1-hydroxyethyl, 1-fluoroethyl or hydroxymethyl, protected hydroxymethyl or 1-(protected hydroxy) ethyl;

$R^{11}$ is hydrogen or a carboxy protecting group;

$R^{12}$ is hydrogen or an amino protecting group;

$R^{18}$ is carboxy, hydroxy, a protected carboxy group or a protected hydroxy group;

and the phenyl ring is optionally further substituted by one or two substituents selected from halo, cyano, $C_{1-4}$alkyl, nitro, hydroxy, carboxy, $C_{1-4}$alkoxy, trifluoromethyl, $C_{1-4}$alkoxycarbonyl, carbamoyl, $C_{1-4}$alkycarbamoyl, di-$C_{1-4}$alkylcarbamoyl, amino, $C_{1-4}$alkylamino, di-$C_{1-4}$alkylamino, sulphonic acid, $C_{1-4}$alkylS(O)$_n$—, wherein n is 0–2, N-$C_{1-4}$alkanesulphonamido, $C_{1-4}$alkanoylamino and $C_{1-4}$alkanoyl (N-$C_{1-4}$alkyl)amino:

provided that at least one protecting group is present, and the phenyl ring is substituted by at least one carboxy.

14. A method of treatment of a bacterial infection by administering to a patient in need thereof an antibacterially effective amount of a carbapenem compound of formula (I):

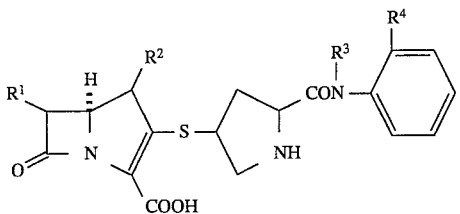

wherein:

$R^1$ is 1-hydroxyethyl, 1-fluoroethyl or hydroxymethyl;

$R^2$ is hydrogen or $C_{1-4}$alkyl;

$R^3$ is hydrogen or $C_{1-4}$alkyl;

$R^4$ is hydroxy or carboxy; and the phenyl ring is optionally further substituted by one or two substituents selected from halo, cyano, $C_{1-4}$alkyl, nitro, hydroxy, carboxy, $C_{1-4}$alkoxy, trifluoromethyl, $C_{1-4}$alkoxycarbonyl, carbomoyl, $C_{1-4}$alkycarbamoyl, di-$C_{1-4}$alkylcarbamoyl, amino, $C_{1-4}$alkylamino, di-$C_{1-4}$alkylamino, sulphonic acid, $C_{1-4}$alkylS(O)$_n$—, wherein n is 0–2, N-$C_{1-4}$alkanesulphonamido, $C_{1-4}$alkanoylamino and $C_{1-4}$alkanoyl (N-$C_{1-4}$alkyl) amino:

provided that the phenyl ring is substituted by at least one carboxy; or a pharmaceutically acceptable salt or in vivo hydrolysable ester thereof.

* * * * *